(12) United States Patent
Berk et al.

(10) Patent No.: US 7,544,695 B2
(45) Date of Patent: Jun. 9, 2009

(54) SPIROCYCLIC COMPOUNDS

(75) Inventors: Scott C. Berk, Cambridge, MA (US); Joshua Close, Franklin, MA (US); Christopher Hamblett, Boston, MA (US); Richard W. Heidebrecht, Brookline, MA (US); Solomon D. Kattar, Medford, MA (US); Laura T. Kliman, Cambridge, MA (US); Dawn M. Mampreian, Brookline, MA (US); Joey L. Methot, Westwood, MA (US); Thomas Miller, Brookline, MA (US); David L. Sloman, Boston, MA (US); Matthew G. Stanton, Medfield, MA (US); Paul Tempest, Brookline, MA (US); Anna A. Zabierek, East Kingston, NH (US)

(73) Assignee: Merck & Co., Inc., Rahway, NJ (US)

( * ) Notice: Subject to any disclaimer, the term of this patent is extended or adjusted under 35 U.S.C. 154(b) by 85 days.

(21) Appl. No.: 11/600,426

(22) Filed: Nov. 16, 2006

(65) Prior Publication Data

US 2007/0117824 A1    May 24, 2007

Related U.S. Application Data

(60) Provisional application No. 60/739,324, filed on Nov. 23, 2005.

(51) Int. Cl.
*A61K 31/438* (2006.01)
*C07D 498/10* (2006.01)
(52) U.S. Cl. .................................. 514/278; 546/19
(58) Field of Classification Search ............... 514/278; 546/19
See application file for complete search history.

(56) References Cited

U.S. PATENT DOCUMENTS

| 5,369,108 | A | 11/1994 | Breslow et al. |
| 5,700,811 | A | 12/1997 | Breslow et al. |
| 5,932,616 | A | 8/1999 | Breslow et al. |
| 6,087,367 | A | 7/2000 | Breslow et al. |
| 6,511,990 | B1 | 1/2003 | Breslow et al. |
| 2004/0142953 | A1 | 7/2004 | Delorme et al. |
| 2005/0288282 | A1 | 12/2005 | Delorme et al. |

FOREIGN PATENT DOCUMENTS

| EP | 1 378 510 | 1/2004 |
| EP | 1 541 574 | 6/2005 |
| WO | WO 01/30780 | 5/2001 |
| WO | WO 01/38322 | 5/2001 |
| WO | WO 03/024448 | 3/2003 |
| WO | WO 03/075929 | 9/2003 |
| WO | WO 03/076395 | 9/2003 |
| WO | WO 03/076422 | 9/2003 |
| WO | WO 03/087057 | 10/2003 |
| WO | WO 03/092686 | 11/2003 |
| WO | WO 2004/058234 | 7/2004 |
| WO | WO 2004/069823 | 8/2004 |
| WO | WO 2005/030704 | 4/2005 |
| WO | WO 2005/030705 | 4/2005 |
| WO | WO 2005/092899 | 10/2005 |
| WO | WO 2007/061880 | 5/2007 |

*Primary Examiner*—Charanjit S Aulakh
(74) *Attorney, Agent, or Firm*—Nicole M. Beeler; David A. Muthard; Li Su

(57) ABSTRACT

The present invention relates to a novel class of substituted spirocyclic compounds. These compounds can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the compounds of the instant invention and safe dosing regimens of these pharmaceutical compositions, which are easy to follow, and which result in a therapeutically effective amount of these compounds in vivo.

14 Claims, No Drawings

SPIROCYCLIC COMPOUNDS

PRIORITY CLAIM

This application claims priority from the U.S. Provisional Application No. 60/739,324, that was filed on Nov. 23, 2005 and is now abandoned.

FIELD OF THE INVENTION

The present invention relates to a novel class of substituted spirocyclic compounds. These compounds can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

BACKGROUND OF THE INVENTION

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349-52 (1997)). These effects are thought to occur through changes in the structure of chromatin by altering the affinity of histone proteins for coiled DNA in the nucleosome. There are five types of histones that have been identified. Histones H2A, H2B, H3 and H4 are found in the nucleosome, and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, the contents of which are hereby incorporated by reference, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003, the entire content of which is hereby incorporated by reference). Further, these hydroxamic acid derivatives have been identified as useful for treating diseases of the central nervous system (CNS) such as neurodegenerative diseases and for treating brain cancer (See, U.S. application Ser. No. 10/273,401, filed Oct. 16, 2002, the entire content of which is hereby incorporated by reference).

In view of the wide variety of applications for compounds containing hydroxamic acid moieties, the development of new inhibitors having improved properties, for example, increased potency or increased bioavailability is highly desirable.

SUMMARY OF THE INVENTION

The present invention relates to a novel class of substituted spirocyclic compounds. These compounds, which can be used to treat cancer, inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating a patient having a tumor characterized by proliferation of neoplastic cells. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the compounds of the instant invention, and safe, dosing regimens of these pharmaceutical compositions, which are easy to follow, and which result in a therapeutically effective amount of these compounds in vivo.

The present invention relates to compounds represented by Formula I and pharmaceutically acceptable salts, solvates and hydrates thereof, as detailed herein.

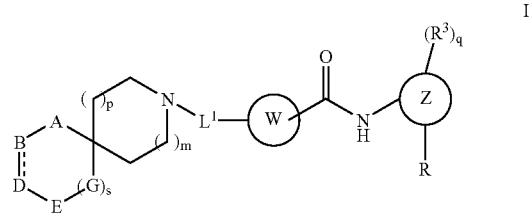

The foregoing and other objects, features and advantages of the invention will be apparent from the following more particular description of embodiments of the invention.

DETAILED DESCRIPTION OF THE INVENTION

The present invention relates to a novel class of substituted spirocyclic compounds. The compounds of the instant invention can inhibit histone deacetylase and are suitable for use in selectively inducing terminal differentiation, and arresting cell growth and/or apoptosis of neoplastic cells, thereby inhibiting proliferation of such cells. Thus, the compounds of the present invention are useful in treating cancer in a subject. The compounds of the invention may also be useful in the prevention and treatment of TRX-mediated diseases, such as autoimmune, allergic and inflammatory diseases, and in the prevention and/or treatment of diseases of the central nervous system (CNS), such as neurodegenerative diseases.

The present invention relates to compounds represented by Formula I:

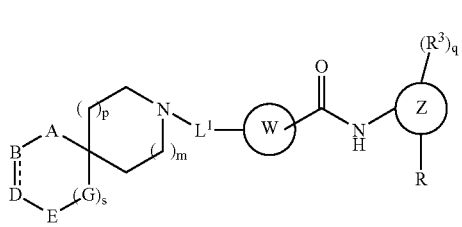

I wherein
A, B and D are independently selected from $CR^1{}_2$, $NR^{1a}$, C(O) and O;
E is selected from a bond, $CR^1{}_2$, $NR^{1a}$, C(O) and O;
   wherein at least one of A, B, D or E is $CR^1{}_2$; and provided that when A is O, then E is not O;
G is $CR^1{}_2$;
R is selected from $NH_2$ and OH;
---- is an optional double bond;

is an aryl or heteroaryl, optionally substituted with from 1 to 3 substituents selected from $R^7$;

is an aryl or heteroaryl;
$R^1$ is independently selected from
  1) hydrogen,
  2) $C_1$-$C_6$ alkyl,
  3) $(CR^6{}_2)_n R^{10}$,
  4) $(CR^6{}_2)_n C(O)R^4$,
  5) $(CR^6{}_2)_n C(O)OR^4$,
  6) $(CR^6{}_2)_n C(O)NR^5{}_2$,
  7) $(CR^6{}_2)_n S(O)_2 R^4$,
  8) $(CR^6{}_2)_n OH$, and
  9) halo;

$R^{1a}$ is independently selected from
  1) hydrogen,
  2) $C_1$-$C_6$ alkyl,
  3) $(CR^6{}_2)_n R^{10}$,
  4) $(CR^6{}_2)_n C(O)R^4$,
  5) $(CR^6{}_2)_n C(O)OR^4$,
  6) $(CR^6{}_2)_n C(O)NR^5{}_2$, and
  7) $(CR^6{}_2)_n S(O)_2 R^4$;
$L^1$ is selected from a bond, $-(CR^{11})_r-$, $-C(O)NR^5-$, $-NR^5 C(O)-$, and $-C(O)-$;
  wherein r is 1, 2 or 3;
$R^3$ is selected from
  1) H,
  2) unsubstituted or substituted $C_1$-$C_6$ alkyl,
  3) unsubstituted or substituted aryl,
  4) unsubstituted or substituted heteroaryl
  5) halo,
  6) CN,
  7) amide,
  8) carboxyl,
  9) $C_1$-$C_7$ alkoxy,
  10) $C_1$-$C_7$ haloalkyl,
  11) $C_1$-$C_7$ haloalkyloxy,
  12) $C_1$-$C_7$ hydroxyalkyl,
  13) $C_1$-$C_7$ alkenyl,
  14) $C_1$-$C_7$ alkynyl,
  15) $C_1$-$C_7$ alkyl-C(=O)O—,
  16) $C_1$-$C_7$ alkyl-C(=O)—,
  17) hydroxyalkoxy,
  18) —$NHSO_2$,
  19) —$SO_2 NH$,
  20) $C_1$-$C_7$ alkyl-$NHSO_2$—,
  21) $C_1$-$C_7$ alkyl-$SO_2 NH$—,
  22) $C_1$-$C_7$ alkylsulfonyl,
  23) $C_1$-$C_7$ alkylamino,
  24) di($C_1$-$C_7$)alkylamino, and
  25) $L^2$-$R^{12}$;
$R^4$ is independently selected from
  1) H,
  2) $C_1$-$C_6$ alkyl,
  3) aryl, and
  3) heterocyclyl,
  wherein alkyl, aryl or heterocyclyl may be optionally substituted;
$R^5$ is independently selected from
  1) hydrogen,
  2) $C_1$-$C_6$ alkyl, and
  3) aryl,
  which may be optionally substituted with 1 to 3 substituents selected from $C_1$-$C_6$ alkyl, aryl, heteroaryl or halo;
$R^6$ is independently selected from
  1) hydrogen,
  2) $C_1$-$C_6$ alkyl,
  3) aryl,
  4) $OR^{11}$,
  5) halo, and
  6) $NR^{11}$;
  wherein the alkyl or aryl may be optionally substituted with 1 to 3 substituents selected from $C_1$-$C_6$ alkyl, aryl, heteroaryl or halo;
$R^7$ is independently selected from hydrogen, OH, $NR^{11}{}_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo group, amide, hydroxyalkoxy, —$NR^{11}SO_2$, —$SO_2 NR^{11}$, $C_1$-$C_7$ alkyl- $NR^{11}SO_2$—, $C_1$-$C_7$ alkyl-$SO_2NR^{11}$—, $C_1$-$C_7$alkylsulfonyl, $C_1$-$C_7$ alkylamino and di($C_1$-$C_7$)alkylamino;

$R^{10}$ is independently selected from
1) aryl, and
2) heterocyclyl,
which may be optionally substituted;

$R^{11}$ is independently selected from hydrogen, unsubstituted or substituted $C_1$-$C_6$ alkyl, and unsubstituted or substituted aryl;

$L^2$ is selected from
1) a bond,
2) $C_1$-$C_4$ alkylene,
3) $C_1$-$C_4$ alkynyl,
4) $C_1$-$C_4$ alkenyl,
5) —O—,
6) —S—,
7) —NH—,
8) —C(=O)NH—,
9) —NHC(=O)—,
10) —NHC(=O)NH—,
11) —$SO_2NH$—,
12) —$NHSO_2$—,
13) —$SO_2$—,
14) —C(=O)— and
15) —C(=O)O—;

$R^{12}$ is selected from:
1) substituted or unsubstituted heteroaryl,
2) substituted or unsubstituted heterocyclyl,
3) substituted or unsubstituted aryl, and
4) substituted or unsubstituted $C_3$-$C_8$ cycloalkyl;

m is 0, 1 or 2;
n is independently selected from 0, 1, 2, 3 and 4;
p is 0, 1 or 2, provided the sum of variables m and p is not greater than 2;
q is 1, 2, 3, or 4;
s is 0 or 1;

or a stereoisomer or a pharmaceutically acceptable salt thereof.

In another embodiment, the present invention relates to compounds represented by Formula II:

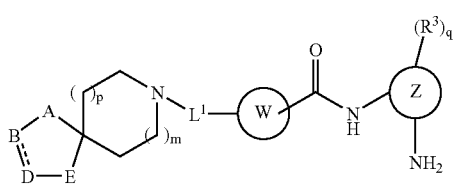

wherein
A, B and D are independently selected from $CR^1_2$, $NR^{1a}$, C(O) and O;
E is selected from a bond, $CR^1_2$, $NR^{1a}$, C(O) and O;
wherein at least one of A, B, D or E is $CR^1_2$; and provided that when A is O, then E is not O;
---- is an optional double bond;

is an aryl or heteroaryl, optionally substituted with from 1 to 3 substituents selected from $R^7$;

is an aryl or heteroaryl;

$R^1$ is independently selected from
1) hydrogen,
2) $C_1$-$C_6$ alkyl,
3) $(CR^6_2)_nR^{10}$,
4) $(CR^6_2)_nC(O)R^4$,
5) $(CR^6_2)_nC(O)OR^4$,
6) $(CR^6_2)_nC(O)NR^5_2$,
7) $(CR^6_2)_nS(O)_2R^4$,
8) $(CR^6_2)_nOH$, and
9) halo;

$R^{1a}$ is independently selected from
1) hydrogen,
2) $C_1$-$C_6$ alkyl,
3) $(CR^6_2)_nR^{10}$,
4) $(CR^6_2)_nC(O)R^4$,
5) $(CR^6_2)_nC(O)OR^4$,
6) $(CR^6_2)_nC(O)NR^5_2$, or
7) $(CR^6_2)_nS(O)_2R^4$;

$L^1$ is selected from a bond, —$CR^{11}_2$—, —C(O)$NR^5$—, —$NR^5C(O)$—, and —C(O)—;

$R^3$ is selected from
1) H,
2) unsubstituted or substituted $C_1$-$C_6$ alkyl,
3) unsubstituted or substituted aryl,
4) unsubstituted or substituted heteroaryl
5) halo,
6) CN,
7) amide,
8) carboxyl,
9) $C_1$-$C_7$alkoxy,
10) $C_1$-$C_7$ haloalkyl,
11) $C_1$-$C_7$ haloalkyloxy,
12) $C_1$-$C_7$ hydroxyalkyl,
13) $C_1$-$C_7$ alkenyl,
14) $C_1$-$C_7$ alkynyl,
15) $C_1$-$C_7$alkyl-C(=O)—,
16) $C_1$-$C_7$ alkyl-C(=O)—,
17) hydroxyalkoxy,
18) —$NHSO_2$,
19) —$SO_2NH$,
20) $C_1$-$C_7$ alkyl-$NHSO_2$—,
21) $C_1$-$C_7$ alkyl-$SO_2NH$—,
22) $C_1$-$C_7$ alkylsulfonyl,
23) $C_1$-$C_7$ alkylamino,
24) di($C_1$-$C_7$)alkylamino, and
25) $L^2$-$R^{12}$, $R^4$ is independently selected from
1) H,
2) $C_1$-$C_6$ alkyl,
3) aryl, and
3) heterocyclyl,
wherein alkyl, aryl or heterocyclyl may be optionally substituted;

$R^5$ is independently selected from
1) hydrogen,
2) $C_1$-$C_6$ alkyl, and
3) aryl, which may be optionally substituted with 1 to 3 substituents selected from $C_1$-$C_6$ alkyl, aryl, heteroaryl or halo;

$R^6$ is independently selected from
1) hydrogen,
2) $C_1$-$C_6$ alkyl,
3) aryl,
4) $OR^{11}$,
5) halo, and
6) $NR^{11}$;
wherein the alkyl or aryl may be optionally substituted with 1 to 3 substituents selected from $C_1$-$C_6$ alkyl, aryl, heteroaryl or halo;

$R^7$ is independently selected from hydrogen, OH, $NR^{11}_2$, nitro, CN, amide, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo group, amide, hydroxyalkoxy, —$NR^{11}SO_2$, —$SO_2NR^{11}$, $C_1$-$C_7$ alkyl-$NR^{11}SO_2$—, $C_1$-$C_7$ alkyl-$SO_2NR^{11}$—, $C_1$-$C_7$ alkylsulfonyl, $C_1$-$C_7$ alkylamino and di($C_1$-$C_7$)alkylamino;

$R^{10}$ is independently selected from
1) aryl, and
2) heterocyclyl,
which may be optionally substituted;

$R^{11}$ is independently selected from hydrogen, unsubstituted or substituted $C_1$-$C_6$ alkyl, and unsubstituted or substituted aryl;

$L^2$ is selected from
1) a bond,
2) $C_1$-$C_4$ alkylene,
3) $C_1$-$C_4$ alkynyl,
4) $C_1$-$C_4$ alkenyl,
5) —O—,
6) —S—,
7) —NH—,
8) —C(=O)NH—,
9) —NHC(=O)—,
10) —NHC(=O)NH—,
11) —$SO_2NH$—,
12) —$NHSO_2$—,
13) —$SO_2$—,
14) —C(=O)— and
15) —C(=O)O—;

$R^{12}$ is selected from:
1) substituted or unsubstituted heteroaryl,
2) substituted or unsubstituted heterocyclyl,
3) substituted or unsubstituted aryl, and
4) substituted or unsubstituted $C_3$-$C_8$ cycloalkyl;

m is 0, 1 or 2;
n is independently selected from 0, 1, 2, 3 and 4;
p is 0, 1 or 2, provided the sum of variables m and p is not greater than 2;
q is 1, 2, 3, or 4;

or a stereoisomer or a pharmaceutically acceptable salt thereof.

A futher embodiment relates to compounds represented by Formula III:

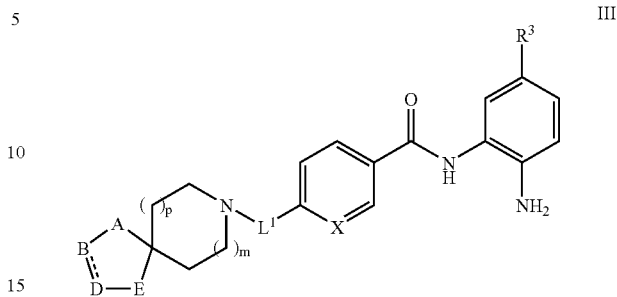

wherein
X is CH or N;
and all other substituents and variables are as defined above in Formula II, or a stereoisomer or a pharmaceutically acceptable salt thereof.

A further embodiment of the invention is a compound of Formula III, wherein
A is $CR^1_2$, C(O), $NR^{1a}$ or O;
B is $CR^1_2$, $NR^{1a}$, or C(O);
D is $CR^1_2$, or $NR^{1a}$;
E is a bond, $CR^1_2$, or C(O);
and all other substituents and variables are as defined above in Formula III, or a stereoisomer or a pharmaceutically acceptable salt thereof.

Specific embodiments depicting non-limiting Examples of the compounds of the instant invention are provided in the Experimental Section herein below.

Specific examples of the compounds of the instant invention include:

N-(2-Aminophenyl)-6-(4-oxo-1-phenyl-1,3,8-triazaspiro[4.5]dec-8-yl)nicotinamide;

N-(2-aminophenyl)-6-(7-benzyl-2,7-diazaspiro[4.4]non-2-yl)nicotinamide;

N-(2-aminophenyl)-6-(7-phenyl-2,7-diazaspiro[4.4]non-2-yl)nicotinamide;

N-(2-aminophenyl)-6-[7-(2-chlorophenyl)-2,7-diazaspiro[4.4]non-2-yl]nicotinamide;

N-(2-aminophenyl)-6-[7-(3-chlorophenyl)-2,7-diazaspiro[4.4]non-2-yl]nicotinamide;

N-(2-aminophenyl)-6-[7-(4-chlorophenyl)-2,7-diazaspiro[4.4]non-2-yl]nicotinamide;

7-(5-{[(2-aminophenyl)amino]carbonyl}pyridin-2-yl)-N-phenyl-1-oxa-2,7-diazaspiro[4.4]non-2-ene-3-carboxamide;

N-(2-aminophenyl)-6-[1-(3-methylphenyl)-2-oxo-1,3,8-triazaspiro[4.5]dec-8-yl]nicotinamide;

N-(2-aminophenyl)-6-{3-[2-(4-fluorophenyl)ethyl]-1-oxa-8-azaspiro[4.5]dec-8-yl}nicotinamide;

N-(2-aminophenyl)-6-[3-(4-fluorobenzyl)-2-oxo-1-oxa-8-azaspiro[4.5]dec-8-yl]nicotinamide;

N-(4-Aminobiphenyl-3-yl)-6-(4-oxo-1-phenyl-1,3,8-triazaspiro[4.5]dec-8-yl)nicotinamide;

7-(5-{[(4-aminobiphenyl-3-yl)amino]carbonyl}pyridin-2-yl)-N-(2-phenylethyl)-1-oxa-2,7-diazaspiro[4.4]non-2-ene-3-carboxamide;

N-(4-aminobiphenyl-3-yl)-6-(7-benzyl-2,7-diazaspiro[4.4]non-2-yl)nicotinamide;
N-(4-aminobiphenyl-3-yl)-6-(7-phenyl-2,7-diazaspiro[4.4]non-2-yl)nicotinamide;
6-(7-acetyl-2,7-diazaspiro[4.4]non-2-yl)-N-(4-aminobiphenyl-3-yl)nicotinamide;
N-[2-Amino-5-(2-thienyl)phenyl]-6-(2,8-diazaspiro[4.5]dec-8-yl)nicotinamide;
N-(2-aminophenyl)-6-(2,8-diazaspiro[4.5]dec-8-yl)nicotinamide;
N-[2-amino-5-(3-thienyl)phenyl]-6-(2,8-diazaspiro[4.5]dec-8-yl)nicotinamide;
6-(2-Acetyl-2,7-diazaspiro[4.5]dec-7-yl)-N-[2-amino-5-(2-thienyl)phenyl]-nicotinamide;
benzyl 7-(5-{[(2-aminophenyl)amino]carbonyl}pyridin-2-yl)-2,7-diazaspiro[4.5]decane-2-carboxylate;
benzyl 7-(5-{[(4-aminobiphenyl-3-yl)amino]carbonyl}pyridin-2-yl)-2,7-diazaspiro[4.5]decane-2-carboxylate;
N-(4-aminobiphenyl-3-yl)-6-(2-benzoyl-2,7-diazaspiro[4.5]dec-7-yl)nicotinamide;
N-(4-aminobiphenyl-3-yl)-6-(2-pyrimidin-2-yl-2,7-diazaspiro[4.5]dec-7-yl)nicotinamide;
6-(2-acetyl-2,7-diazaspiro[4.5]dec-7-yl)-N-(4-aminobiphenyl-3-yl)nicotinamide;
ethyl 7-(5-{[(4-aminobiphenyl-3-yl)amino]carbonyl}pyridin-2-yl)-2,7-diazaspiro[4.5]decane-2-carboxylate;
7-(5-{[(4-aminobiphenyl-3-yl)amino]carbonyl}pyridin-2-yl)-N-ethyl-2,7-diazaspiro[4.5]decane-2-carboxamide;
N-[2-amino-5-(2-thienyl)phenyl]-6-(2-pyrimidin-2-yl-2,7-diazaspiro[4.5]dec-7-yl)nicotinamide;
ethyl 7-[5-({[2-amino-5-(2-thienyl)phenyl]amino}carbonyl)pyridin-2-yl]-2,7-diazaspiro[4.5]decane-2-carboxylate;
7-[5-({[2-amino-5-(2-thienyl)phenyl]amino}carbonyl)pyridin-2-yl]-N-ethyl-2,7-diazaspiro[4.5]decane-2-carboxamide;
N-[2-Amino-5-(2-thienyl)phenyl]-6-(4-oxo-1-phenyl-1,3,8-triazaspiro[4.5]dec-8-yl)nicotinamide;
6-(7-acetyl-2,7-diazaspiro[4.4]non-2-yl)-N-[2-amino-5-(2-thienyl)phenyl]nicotinamide;
6-(7-acetyl-2,7-diazaspiro[4.4]non-2-yl)-N-[2-amino-5-(3-thienyl)phenyl]nicotinamide;
N-[2-amino-5-(2-thienyl)phenyl]-6-(4-oxo-1-phenyl-1,3,8-triazaspiro[4.5]dec-8-yl)nicotinamide;
N-[2-Amino-5-(2-thienyl)phenyl]-6-(2-oxo-1-oxa-3,8-diazaspiro[4.5]dec-8-yl)nicotinamide;
N-[2-amino-5-(3-thienyl)phenyl]-6-(2-oxo-1-oxa-3,8-diazaspiro[4.5]dec-8-yl)nicotinamide;
N-[2-amino-5-(2-thienyl)phenyl]-6-(3-methyl-2-oxo-1-oxa-3,8-diazaspiro[4.5]dec-8-yl)nicotinamide;
N-(4-aminobiphenyl-3-yl)-6-(3-methyl-2-oxo-1-oxa-3,8-diazaspiro[4.5]dec-8-yl)nicotinamide;
N-(4-aminobiphenyl-3-yl)-6-(2-oxo-1-oxa-3,8-diazaspiro[4.5]dec-8-yl)nicotinamide;
N-[2-Amino-5-(2-thienyl)phenyl]-6-(1,8-diazaspiro[4.5]dec-8-yl)nicotinamide;
N-[2-amino-5-(3-thienyl)phenyl]-6-(1,8-diazaspiro[4.5]dec-8-yl)nicotinamide;
N-(4-aminobiphenyl-3-yl)-6-(1,8-diazaspiro[4.5]dec-8-yl)nicotinamide;
N-(4-Amino-1-phenyl-1-1H-pyrazol-3-yl)-6-(4-oxo-1-phenyl-1,3,8-triazaspiro-[4.5]dec-8-yl)nicotinamide;
6-(7-acetyl-2,7-diazaspiro[4.4]non-2-yl)-N-(4-amino-1-phenyl-1H-pyrazol-3-yl)nicotinamide;
N-[4-amino-1-(3-chlorophenyl)-1H-pyrazol-3-yl]-6-(2,8-diazaspiro[4.5]dec-8-yl)nicotinamide;
8-(5-{[(4-Aminobiphenyl-3-yl)amino]carbonyl}pyridin-2-yl)-N$^3$-phenyl-N$^2$-(2-phenylethyl)-2,8-diazaspiro[4.5]decane-2,3-dicarboxamide;
8-(5-{[(4-Aminobiphenyl-3-yl)amino]carbonyl}pyridin-2-yl)-N-(2-phenylethyl)-1-oxa-2,8-diazaspiro[4.5]dec-2-ene-3-carboxamide;
6-(2-acetyl-2,8-diazaspiro[4.5]dec-8-yl)-N-[2-amino-5-(2-thienyl)phenyl]-nicotinamide;
N-(4-aminobiphenyl-3-yl)-6-(2-benzyl-2,8-diazaspiro[4.5]dec-8-yl)nicotinamide;
N-(4-aminobiphenyl-3-yl)-6-{2-[(2,4-dimethyl-1,3-thiazol-5-yl)sulfonyl]-2,8-diazaspiro[4.5]dec-8-yl}nicotinamide;
8-[5-({[2-amino-5-(2-thienyl)phenyl]amino}carbonyl)pyridin-2-yl]-N-(2-phenylethyl)-2,8-diazaspiro[4.5]decane-2-carboxamide;
8-[5-({[2-amino-5-(2-thienyl)phenyl]amino}carbonyl)pyridin-2-yl]-N-ethyl-2,8-diazaspiro[4.5]decane-2-carboxamide;
8-5-{[(4-aminobiphenyl-3-yl)amino]carbonyl}pyridin-2-yl)-N-ethyl-2,8-diazaspiro[4.5]decane-2-carboxamide;
6-(2-acetyl-2,8-diazaspiro[4.5]dec-8-yl)-N-(4-aminobiphenyl-3-yl)nicotinamide;
6-(2-acetyl-2,8-diazaspiro[4.5]dec-8-yl)-N-[2-amino-5-(2-thienyl)phenyl]nicotinamide;
8-(5-{[(4-aminobiphenyl-3-yl)amino]carbonyl}pyridin-2-yl)-N-ethyl-2,8-diazaspiro[4.5]decane-2-carboxamide;
6-(2-acetyl-2,8-diazaspiro[4.5]dec-8-yl)-N-(4-aminobiphenyl-3-yl)nicotinamide;
6-(2-acetyl-2,8-diazaspiro[4.5]dec-8-yl)-N-[2-amino-5-(2-thienyl)phenyl]nicotinamide;
6-(2-acetyl-2,8-diazaspiro[4.5]dec-8-yl)-N-[2-amino-5-(3-thienyl)phenyl]nicotinamide;
8-[5-({[2-amino-5-(3-thienyl)phenyl]amino}carbonyl)pyridin-2-yl]-N-ethyl-2,8-diazaspiro[4.5]decane-2-carboxamide;
N-(2-aminophenyl)-6-{3-[3,5-bis(trifluoromethyl)benzyl]-4-oxo-1-phenyl-1,3,8-triazaspiro[4.5]dec-8-yl}nicotinamide;
N-(2-aminophenyl)-6-{3-[2-(methylamino)-2-oxoethyl]-4-oxo-1-phenyl-1,3,8-triazaspiro[4.5]dec-8-yl}nicotinamide;
N-(2-aminophenyl)-6-[3-(2-anilino-2-oxoethyl)-4-oxo-1-phenyl-1,3,8-triazaspiro[4.5]dec-8-yl]nicotinamide;
N-(2-aminophenyl)-6-[3-(1H-benzimidazol-2-ylmethyl)-4-oxo-1-phenyl-1,3,8-triazaspiro[4.5]dec-8-yl]nicotinamide;
N-(2-aminophenyl)-6-(3-methyl-4-oxo-1-phenyl-1,3,8-triazaspiro[4.5]dec-8-yl)nicotinamide;
8-[5-({[2-Amino-5-(2-thienyl)phenyl]amino}carbonyl)pyridin-2-yl]-N-ethyl-1,8-diazaspiro[4.5]decane-1-carboxamide;
8-[5-({[2-amino-5-(2-thienyl)phenyl]amino}carbonyl)pyridin-2-yl]-N-ethyl-1,8-diazaspiro[4.5]decane-1-carboxamide;
6-(1-acetyl-1,8-diazaspiro[4.5]dec-8-yl)-N-(4-aminobiphenyl-3-yl)nicotinamide;
6-(1-acetyl-1,8-diazaspiro[4.5]dec-8-yl)-N-[2-amino-5-(2-thienyl)phenyl]nicotinamide;
N-(4-Aminobiphenyl-3-yl)-6-(7-pyrimidin-2-yl-2,7-diazaspiro[4.4]non-2-yl)nicotinamide;
N-(4-aminobiphenyl-3-yl)-6-[7-(phenylsulfonyl)-2,7-diazaspiro[4.4]non-2-yl]nicotinamide;
N-(4-aminobiphenyl-3-yl)-6-(7-benzoyl-2,7-diazaspiro[4.4]non-2-yl)nicotinamide;
7-(5-{[(4-aminobiphenyl-3-yl)amino]carbonyl}pyridin-2-yl)-N-[(1S)-1-phenylethyl]-2,7-diazaspiro[4.4]nonane-2-carboxamide;

7-(5-{[(4-aminobiphenyl-3-yl)amino]carbonyl}pyridin-2-yl)-N-[(1R)-1-phenylethyl]-2,7-diazaspiro[4.4]nonane-2-carboxamide;

7-(5-{[(4-aminobiphenyl-3-yl)amino]carbonyl}pyridin-2-yl)-N-ethyl-2,7-diazaspiro[4.4]nonane-2-carboxamide;

7-(5-{[(4-aminobiphenyl-3-yl)amino]carbonyl}pyridin-2-yl)-N-2-phenylethyl)-2,7-diazaspiro[4.4]nonane-2-carboxamide;

ethyl 7-(5-{[(4-aminobiphenyl-3-yl)amino]carbonyl}pyridin-2-yl)-2,7-diazaspiro[4.4]nonane-2-carboxylate;

N-(4-aminobiphenyl-3-yl)-6-(2,7-diazaspiro[4.5]dec-7-yl)nicotinamide;

Pyridin-3-ylmethyl 7-(5-{[(2-Aminophenyl)amino]carbonyl}pyridin-2-yl)-2,7-diazaspiro[4.4]nonane-2-carboxylate;

benzyl 7-(5-{[(2-aminophenyl)amino]carbonyl}pyridin-2-yl)-2,7-diazaspiro[4.4]nonane-2-carboxylate;

N-(2-aminophenyl)-6-(7-benzoyl-2,7-diazaspiro[4.4]non-2-yl)nicotinamide;

N-(2-aminophenyl)-6-(7-(2-phenylethanoyl)-2,7-diazaspiro[4.4]non-2-yl)nicotinamide;

N-(2-aminophenyl)-6-[7-(3-phenylpropanoyl)-2,7-diazaspiro[4.4]non-2-yl]nicotinamide;

N-(2-aminophenyl)-6-[7-(phenylsulfonyl)-2,7-diazaspiro[4.4]non-2-yl]nicotinamide;

N-(2-aminophenyl)-6-[7-(4-methoxybenzyl)-2,7-diazaspiro[4.4]non-2-yl]nicotinamide;

tert-butyl 7-(5-{[(2-aminophenyl)amino]carbonyl}pyridin-2-yl)-2,7-diazaspiro[4.4]nonane-2-carboxylate;

tert-butyl 8-(5-{[(2-aminophenyl)amino]carbonyl}pyridin-2-yl)-2,8-diazaspiro[4.5]decane-2-carboxylate;

tert-butyl 8-(5-{[(2-aminophenyl)amino]carbonyl}pyridin-2-yl)-1,8-diazaspiro[4.5]decane-1-carboxylate;

benzyl 8-(5-{[(2-aminophenyl)amino]carbonyl}pyridin-2-yl)-1,8-diazaspiro[4.5]decane-1-carboxylate;

N-(2-aminophenyl)-6-(2-benzyl-2,8-diazaspiro[4.5]dec-8-yl)nicotinamide;

benzyl 8-(5-{[(2-aminophenyl)amino]carbonyl}pyridin-2-yl)-2,8-diazaspiro[4.5]decane-2-carboxylate;

N-(2-aminophenyl)-6-[2-(3-phenylpropanoyl)-2,8-diazaspiro[4.5]dec-8-yl]nicotinamide;

pyridin-3-ylmethyl 8-(5-{[(2-aminophenyl)amino]carbonyl}pyridin-2-yl)-2,8-diazaspiro[4.5]decane-2-carboxylate;

8-(5-{[(2-aminophenyl)amino]carbonyl}pyridin-2-yl)-N-[(1R)-1-phenylethyl]-2,8-diazaspiro[4.5]decane-2-carboxamide;

8-(5-{[(2-aminophenyl)amino]carbonyl}pyridin-2-yl)-N-[(1S)-1-phenylethyl]-2,8-diazaspiro[4.5]decane-2-carboxamide;

8-(5-{[(2-aminophenyl)amino]carbonyl}pyridin-2-yl)-N-(4-fluorophenyl)-2,8-diazaspiro[4.5]decane-2-carboxamide;

8-(5-{[(4-Aminobiphenyl-3-yl)amino]carbonyl}pyridin-2-yl)-N-(2-phenylethyl)-2,8-diazaspiro[4.5]decane-2-carboxamide;

N-(4-aminobiphenyl-3-yl)-6-[2-(2-phenylethyl)-2,8-diazaspiro[4.5]dec-8-yl]nicotinamide;

N-(4-Aminobiphenyl-3-yl)-4-(1,8-diazaspiro[4.5]dec-8-yl-methyl)benzamide;

N-(4-{[(4-aminobiphenyl-3-yl)amino]carbonyl}phenyl)-7-benzyl-2,7-diazaspiro[4.4]nonane-2-carboxamide;

N-(4-aminobiphenyl-3-yl)-6-(2,8-diazaspiro[4.5]dec-8-yl)-1-benzothiophene-2-carboxamide;

N-(4-Aminobiphenyl-3-yl)-4-(1,8-diazaspiro[4.5]dec-8-yl)benzamide;

N-(2-Amino-5-thien-2-ylphenyl)-2-(4-oxo-1-phenyl-1,3,8-triazaspiro[4.5]dec-8-yl)-1,3-thiazole-5-carboxamide;

N-(2-aminophenyl)-6-[7-quinolin-8-ylsulfonyl)-2,7-diazaspiro[4.4]non-2-yl]nicotinamide;

N-(2-aminophenyl)-6-{7-[(2,4-dimethyl-1,3-thiazol-5-yl)sulfonyl]-2,7-diazaspiro[4.4]non-2-yl}nicotinamide;

N-(2-aminophenyl)-6-[7-(benzylsulfonyl)-2,7-diazaspiro[4.4]non-2-yl]nicotinamide;

N-(2-aminophenyl)-6-[7-(1-naphthylsulfonyl)-2,7-diazaspiro[4.4]non-2-yl]nicotinamide;

N-(2-aminophenyl)-6-[7-(2-naphthylsulfonyl)-2,7-diazaspiro[4.4]non-2-yl]nicotinamide;

benzyl 7-(5-{[(4-aminobiphenyl-3-yl)amino]carbonyl}pyridin-2-yl)-2,7-diazaspiro[4.4]nonane-2-carboxylate;

N-(4-aminobiphenyl-3-yl)-6-(2,8-diazaspiro[4.5]dec-8-yl)nicotinamide;

N-(4-amino-1-phenyl-1H-pyrazol-3-yl)-6-(2,8-diazaspiro[4.5]dec-8-yl)nicotinamide;

N-(4-aminobiphenyl-3-yl)-4-(2,8-diazaspiro[4.5]dec-8-yl)benzamide;

N-[2-amino-5-(2-thienyl)phenyl]-4-(1,8-diazaspiro[4.5]dec-8-yl)benzamide;

N-(4-amino-1-phenyl-1H-pyrazol-3-yl)-2-(4-oxo-1-phenyl-1,3,8-triazaspiro[4.5]dec-8-yl)-1,3-thiazole-5-carboxamide;

N-(4-aminobiphenyl-3-yl)-4-(2,8-diazaspiro[4.5]dec-8-ylmethyl)benzamide;

N-(4-aminobiphenyl-3-yl)-4-[(4-oxo-1-phenyl-1,3,8-triazaspiro[4.5]dec-8-yl)methyl]benzamide;

N-(4-aminobiphenyl-3-yl)-4-(1,8-diazaspiro[4.5]dec-8-ylmethyl)benzamide;

N-[2-amino-5-(2-thienyl)phenyl]-4-(1,8-diazaspiro[4.5]dec-8-ylmethyl)benzamide;

N-[2-amino-5-(3-thienyl)phenyl]-4-(1,8-diazaspiro[4.5]dec-8-ylmethyl)benzamide;

N-(4-aminobiphenyl-3-yl)-4-(1,8-diazaspiro[4.5]dec-8-ylcarbonyl)benzamide;

tert-butyl 7-(5-{[(2-aminophenyl)amino]carbonyl}pyridin-2-yl)-2,7-diazaspiro[3.5]nonane-2-carboxylate;

N-(2-aminophenyl)-6-(2,7-diazaspiro[3.5]non-7-yl)nicotinamide;

benzyl 7-(5-{[(2-aminophenyl)amino]carbonyl}pyridin-2-yl)-2,7-diazaspiro[3.5]nonane-2-carboxylate;

N-[2-amino-5-(3-thienyl)phenyl]-6-(2,7-diazaspiro[3.5]non-7-yl)nicotinamide;

N-[2-amino-5-(2-thienyl)phenyl]-6-(2,7-diazaspiro[3.5]non-7-yl)nicotinamide;

N-(4-aminobiphenyl-3-yl)-6-(2,7-diazaspiro[3.5]non-7-yl)nicotinamide;

N-(4-aminobiphenyl-3-yl)-4-(2,7-diazaspiro[3.5]non-7-ylcarbonyl)benzamide;

N-(4-{[(4-aminobiphenyl-3-yl)amino]carbonyl}phenyl)-2,7-diazaspiro[3.5]nonane-7-carboxamide;

tert-butyl 2-(5-{[(2-aminophenyl)amino]carbonyl}pyridin-2-yl)-2,7-diazaspiro[3.5]nonane-7-carboxylate;

N-(2-aminophenyl)-6-(2,7-diazaspiro[3.5]non-2-yl)nicotinamide;

benzyl 2-(5-{[(2-aminophenyl)amino]carbonyl}pyridin-2-yl)-2,7-diazaspiro[3.5]nonane-7-carboxylate;

N-(2-aminophenyl)-6-(2,8-diazaspiro[4.5]dec-2-yl)nicotinamide;

tert-butyl 2-(5-{[(2-aminophenyl)amino]carbonyl}pyridin-2-yl)-2,8-diazaspiro[4.5]decane-8-carboxylate;

tert-butyl 2-(5-{[(2-aminophenyl)amino]carbonyl}pyridin-2-yl)-2,7-diazaspiro[4.5]decane-7-carboxylate;

benzyl 2-(5-{[(2-aminophenyl)amino]carbonyl}pyridin-2-yl)-2,7-diazaspiro[4.5]decane-7-carboxylate;

benzyl 2-(5-{[(2-aminophenyl)amino]carbonyl}pyridin-2-yl)-2,8-diazaspiro[4.5]decane-8-carboxylate;

N-(2-aminophenyl)-6-[8-(3-phenylpropanoyl)-2,8-diazaspiro[4.5]dec-2-yl]nicotinamide;

tert-butyl 9-(5-{[(2-aminophenyl)amino]carbonyl}pyridin-2-yl)3,9-diazaspiro[5.5]undecane-3-carboxylate;

N-(2-aminophenyl)-6-(3,9-diazaspiro[5.5]undec-3-yl)nicotinamide;

benzyl 9-(5-{[(2-aminophenyl)amino]carbonyl}pyridin-2-yl)-3,9-diazaspiro[5.5]undecane-3-carboxylate;

N-(2-aminophenyl)-6-(8-benzyl-2,8-diazaspiro[5.5]undec-2-yl)nicotinamide;

N-(4-aminobiphenyl-3-yl)-4-(2,8-diazaspiro[4.5]dec-2-ylcarbonyl)benzamide;

N-(4-{[(4-aminobiphenyl-3-yl)amino]carbonyl}phenyl)-2,8-diazaspiro[4.5]decane-2-carboxamide;

N-(4-aminobiphenyl-3-yl)-4-(2,7-diazaspiro[4.5]dec-2-ylmethyl)benzamide;

N-(4-aminobiphenyl-3-yl)-4-(3,9-diazaspiro[5.5]undec-3-ylmethyl)benzamide;

N-(4-aminobiphenyl-3-yl)-4-(2,7-diazaspiro[4.5]dec-2-ylcarbonyl)benzamide;

N-(4-aminobiphenyl-3-yl)-4-[(9-benzyl-2,9-diazaspiro[5.5]undec-2-yl)carbonyl]benzamide;

N-(4-{[(4-aminobiphenyl-3-yl)amino]carbonyl}phenyl)-9-benzyl-2,9-diazaspiro[5.5]undecane-2-carboxamide;

N-(4-{[(4-aminobiphenyl-3-yl)amino]carbonyl}phenyl)-2,7-diazaspiro[4.5]decane-2-carboxamide;

or a stereoisomer or a pharmaceutically acceptable salt thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. The cycloalkyl is optionally bridged (i.e., forming a bicyclic moiety), for example with a methylene, ethylene or propylene bridge. The bridge may be optionally substituted or branched. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on. In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

When used in the phrases "alkylaryl", "alkylcycloalkyl" and "alkylheterocyclyl" the term "alkyl" refers to the alkyl portion of the moiety and does not describe the number of atoms in the aryl and heteroaryl portion of the moiety. In an embodiment, if the number of carbon atoms is not specified, "alkyl" of "alkylaryl", "alkylcycloalkyl" and "alkylheterocyclyl" refers to $C_1$-$C_{12}$ alkyl and in a further embodiment, the term refers to $C_1$-$C_6$ alkyl.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylenearyl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

In one embodiment, as used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In another embodiment, "aryl" is an aromatic ring of 5 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g., 1-naphthyl and 2-naphthyl; anthracenyl, e.g., 1-anthracenyl, 2-anthracenyl; phenanthrenyl; fluorenonyl, e.g., 9-fluorenonyl, indanyl and the like. A carbocyclic aromatic group is optionally substituted with a designated number of substituents, described below.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

In another embodiment, "heteroaryl" is a monocyclic, bicyclic or tricyclic aromatic ring of 5- to 14-ring atoms of carbon and from one to four heteroatoms selected from O, N, or S. Examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazolyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g., 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g., 2-benzofuranyl and 3-benzofuranyl; dibenzofuranyl, e.g., 2,3-dihydrobenzofuranyl; dibenzothiophenyl; benzothienyl, e.g., 2-benzothienyl and 3-benzothienyl; indolyl, e.g., 2-indolyl and 3-indolyl; benzothiazolyl, e.g., 2-benzothiazolyl; benzooxazolyl, e.g., 2-benzooxazolyl; benzimidazolyl, e.g., 2-benzoimidazolyl; isoindolyl, e.g., 1-isoindolyl and 3-isoindolyl; benzotriazolyl; purinyl; thianaphthenyl, pyrazinyl and the like. Fused polycyclic aromatic ring systems may optionally be substituted with a designated number of substituents, as described herein.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. A nonaromatic heterocycle may be fused with an aromatic aryl group such as phenyl or aromatic heterocycle.

"Heterocyclyl" therefore includes the above mentioned heteroaryls, as well as dihydro and tetrathydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

In an embodiment, "heterocycle" (also referred to herein as "heterocyclyl"), is a monocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydrodropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl and the like.

An "alkylaryl group" (arylalkyl) is an alkyl group substituted with an aromatic group, preferably a phenyl group. A preferred alkylaryl group is a benzyl group. Suitable aromatic groups are described herein and suitable alkyl groups are described herein. Suitable substituents for an alkylaryl group are described herein.

An "alkylheterocyclyl" group" is an alkyl group substituted with a heterocyclyl group. Suitable heterocyclyl groups are described herein and suitable alkyl groups are described herein. Suitable substituents for an alkyheterocyclyl group are described herein.

An "alkylcycloalkyl group" is an alkyl group substituted with a cycloalkyl group. Suitable cycloalkyl groups are described herein and suitable alkyl groups are described herein. Suitable substituents for an alkycycloalkyl group are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

As used herein, many moieties or groups are referred to as being either "substituted or unsubstituted". When a moiety is referred to as substituted, it denotes that any portion of the moiety that is known to one skilled in the art as being available for substitution can be substituted. The phrase "optionally substituted with one or more substituents" means one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—N, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

In an embodiment, A is $CR^1_2$, $NR^{1a}$ or O. In an embodiment, B is $CR^1_2$, $NR^{1a}$, or C(O). In an embodiment, D is $CR^1_2$ or $NR^{1a}$. In an embodiment, E is a bond, $CR^1_2$, or C(O). In a further embodiment, E is $CR^1_2$, or C(O).

In one embodiment of Formula I or II, one of A, B and D is $NR^1$, and the other two are both $CR^1_2$; E is $CR1_2$ or a bond.

In an embodiment of the instant invention,

is pyridyl, phenyl, benzothiophene or thiazolyl.

In an embodiment of the instant invention,

is phenyl or pyrazolyl.

In an embodiment, R is $NH_2$.

In an embodiment, X is CH. In an embodiment, X is N.

In an embodiment, $L^1$ is a bond, $C_1$-$C_6$ alkyl, —C(O)—, —$NR^5$C(O)—, or —C(O)$NR^5$—. In another embodiment, $L^1$ is a bond or $C_1$-$C_6$ alkyl. In another embodiment, $L^1$ is a bond.

In an embodiment, $R^3$ is H, unsubstituted or substituted $C_1$-$C_6$ alkyl, unsubstituted or substituted aryl, or unsubstituted or substituted heteroaryl. In an embodiment, $R^3$ is H, unsubstituted or substituted phenyl or unsubstituted or substituted thienyl. In an embodiment, $R^3$ is phenyl or thienyl, optionally substituted with halo.

In an embodiment, $R^4$ is independently selected from H, $C_1$-$C_6$ alkyl, aryl, and heterocyclyl, wherein alkyl, aryl or heterocyclyl may be optionally substituted with one or more of $R^{10}$.

In an embodiment, $R^{10}$ is independently selected from aryl, and heterocyclyl, which may be optionally substituted with $C_1$-$C_6$ alkyl, $CF_3$, halo or $OR^{11}$. In another embodiment, $R^{10}$ is phenyl, pyridyl, pyrimidinyl, quinolinyl, thiazolyl, naphthyl or benzimidazolyl, wherein said phenyl, pyridyl, pyrimidinyl, quinolinyl, thiazolyl, naphthyl or benzimidazolyl is optionally substituted with $C_1$-$C_6$ alkyl, $CF_3$, halo or $OR^{11}$.

In an embodiment, variable q is 1.

In an embodiment of Formula I, A is $CR^1_2$, $NR^{1a}$ or O; B is $CR^1_2$, $NR^{1a}$, or C(O); D is $CR^1_2$ or $NR^{1a}$; E is a bond, $CR^1_2$, or C(O);

is pyridyl, phenyl, benzothiophene or thiazolyl;

is phenyl or pyrazolyl; and variable s is 0.

In an embodiment of Formula I, A is $CR^1_2$, $NR^{1a}$ or O; B is $CR^1_2$, $NR^{1a}$, or C(O); D is $CR^1_2$ or $NR^{1a}$; E is a bond, $CR^1_2$, or C(O);

is pyridyl, phenyl, benzothiophene or thiazolyl;

is phenyl or pyrazolyl; and variable s is 1.

In an embodiment of Formula I, A is $CR^1_2$, $NR^{1a}$ or O; B is $CR^1_2$, $NR^{1a}$, or C(O); D is $CR^1_2$ or $NR^{1a}$; E is a bond;

is pyridyl, phenyl, benzothiophene or thiazolyl;

is phenyl or pyrazolyl; and variable s is 0.

In an embodiment of Formula I, A is $CR^1_2$, $NR^{1a}$ or O; B is $CR^1_2$, $NR^{1a}$, or C(O); D is $CR^1_2$ or $NR^{1a}$; E is $CR^1_2$, or C(O);

is pyridyl, phenyl, benzothiophene or thiazolyl;

is phenyl or pyrazolyl; and variable s is 1.

In an embodiment of Formula II, A is $CR^1_2$, $NR^{1a}$ or O; B is $CR^1_2$, $NR^{1a}$, or C(O); D is $CR^1_2$ or $NR^{1a}$; E is a bond, $CR^1_2$, or C(O);

is pyridyl, phenyl, benzothiophene or thiazolyl; and

is phenyl or pyrazolyl.

In an embodiment of Formula II, A is $NR^{1a}_2$ or O, B is C(O) or $CR^1_2$, D is $NR^{1a}_2$ or $CR^1_2$, and E is $CR^1_2$.

In another embodiment of Formula II, A is $NR^{1a}_2$, B is C(O), D is $NR^1_2$ and E is $CR^1_2$.

In an embodiment of Formula II, A is O, B is $NR^{1a}_2$, D is $CR^1_2$, there is a double bond between B and D, and E is $CR^1_2$.

In yet another embodiment of Formula II, A is O, B is C(O) or $CR^1_2$, D is $CR^1_2$ and E is $CR^1_2$.

In a further embodiment, A is O, B is C(O), D is $NR^{1a}_2$ and E is $CR^1_2$.

In one embodiment of Formula I or II, p=0 and m=1.
In one embodiment of Formula I or II, p=1 and m=1.
In one embodiment of Formula I or II, p=0 and m=2.
In one embodiment of Formula I or II, E is a bond.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the compounds of the instant invention disclosed herein. A prodrug of any of the compounds can be made using well-known pharmacological techniques.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The compounds of the instant invention described herein can, as noted above, be prepared in the form of their pharmaceutically acceptable salts. Pharmaceutically acceptable salts are salts that retain the desired biological activity of the parent compound and do not impart undesired toxicological effects. Examples of such salts are acid addition salts, organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, trifluoroacetic acid, formic acid, phosphoric acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also salts formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the compounds of the instant invention. As demonstrated herein, the compounds of the present invention are useful for the treatment of cancer. In addition, there is a wide range of other diseases for which substituted nicotinamides may be useful. Non-limiting examples are thioredoxin (TRX)-mediated diseases as described herein, and diseases of the central nervous system (CNS) as described herein.

1. Treatment of Cancer

As demonstrated herein, the compounds of the present invention are useful for the treatment of cancer. Accordingly, in one embodiment, the invention relates to a method of treating cancer in a subject in need of treatment comprising administering to said subject a therapeutically effective amount of the compounds of the instant invention.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non- Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In an embodiment, the instant compounds are useful in the treatment of cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

2. Treatment of Thioredoxin (TRX)-Mediated Diseases

In another embodiment, the compounds of the instant invention are used in a method of treating a thioredoxin (TRX)-mediated disease or disorder in a subject in need thereof, comprising administering to the subject a therapeutically effective amount of one or more of the compounds of the instant invention.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the compounds of the instant invention are used in a method of treating a disease of the central nervous system in a subject in need thereof comprising administering to the subject a therapeutically effective amount of any one or more of the compounds of the instant invention.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

DEFINITIONS

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneously with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the compounds are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the compounds are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/ or inhibition (partial or complete) of progression of the disease or disease.

Furthermore, in the present invention, when the compounds are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the compounds of the present invention show improved activity as histone deacetylase (HDAC) inhibitors. Accordingly, in one embodiment, the invention relates to a method of inhibiting the activity of histone deacetylase comprising contacting the histone deacetylase with an effective amount of one or more of the compounds of the instant invention.

Histone deacetylases (HDACs), as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

Histone deacetylase inhibitors or HDAC inhibitors, as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes. It is also to be understood that the compounds of the present invention are capable of inhibiting any of the histone deacetylases set forth above, or any other histone deacetylases.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assays which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 μL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIOMOL Research Laboratories, Inc., Plymouth Meeting, PA.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 μg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the p21$^{WAF1}$ gene. The p21$^{WAF1}$ protein is induced within 2 hours of culture with HDAC inhibitors in a variety of transformed cells using standard methods. The induction of the p21$^{WAF1}$ gene is associated with accumulation of acetylated histones in the chromatin region of this gene. Induction of p21$^{WAF1}$ can therefore be recognized as involved in the G1 cell cycle arrest caused by HDAC inhibitors in transformed cells.

Combination Therapy

The compounds of the present invention can be administered alone or in combination with other therapies suitable for the disease or disorder being treated. Where separate dosage formulations are used, the compounds of the instant invention and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the compounds of the instant invention and the other therapeutic agent are realized by the patient at substantially the same time. In an embodiment, such beneficial effect is achieved when the target blood level concentrations of each active drug are maintained at substantially the same time.

The instant compounds may also be useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds may also be useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, Ifulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethyl-ornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos. US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo4,6,7,8-tetrahydro-3H-pyrimidino[5,4-b][1,4]thiazin-6-yl-(S)-ethyl]-2,5-thienoyl-L-glutamic acid, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, erythropoietin (epoietin-$\alpha$), granulocyte-CSF (filgrastin), granulocyte, macrophage-CSF (sargramostim), pentosan polysulfate, cyclooxygenase inhibitors, including nonsteroidal anti-inflammatories ((NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of P13K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]-methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al. (*Am J Hum Genet* 61:785-789, 1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (vaispodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references, the contents of which are incorporated by reference herein.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39:

943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The use of all of these approaches in combination with the compounds of Formula I and II, as described herein, are within the scope of the present invention.

Dosages and Dosing Schedules

The dosage regimen utilizing the compounds of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 5-4000 mg/m$^2$ administered orally once-daily, twice-daily or three times-daily, continuous (every day) or intermittently (e.g., 3-5 days a week). For example, when used to treat the desired disease, the dose of the compounds of the instant invention can range between about 2 mg to about 2000 mg per day.

The compound of the instant invention may be administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the compounds of the instant invention of between about 1.0 mg/mL to about 10 mg/mL. In one example, a sufficient volume of intravenous formulation can be administered to a patient in a day such that the total dose for the day is between about 10 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations and combinations of the dosages and dosing schedules are included within the scope of the present invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

Pharmaceutical Compositions

The compounds of the invention, and derivatives, fragments, analogs, homologs pharmaceutically acceptable salts or hydrate thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. In one embodiment, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to a compound of the instant invention and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The compounds of the present invention may be administered intravenously on the first day of treatment, with oral administration on the second day and all consecutive days thereafter.

The compounds of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound. In one embodiment, the concentration of the compound in the patient's plasma is maintained at about 10 nM. In another embodiment, the concentration of the compound in the patient's plasma is maintained at about 25 nM. In another embodiment, the concentration of the compound in the patient's plasma is maintained at about 50 nM. In another embodiment, the concentration of the compound in the patient's plasma is maintained at about 100 nM. In another embodiment, the concentration of the compound in the patient's plasma is maintained at about 500 nM. In another embodiment, the concentration of the compound in the patient's plasma is maintained at about 1000 nM. In another embodiment, the concentration of the compound in the patient's plasma is maintained at about 2500 nM. In another embodiment, the concentration of the compound in the patient's plasma is maintained at about 5000 nM. The optimal amount of the compound that should be administered to the patient in the practice of the present invention will depend on the particular compound used and the type of cancer being treated.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

In Vitro Methods:

The present invention also provides methods of using the compounds of the present invention for inducing terminal differentiation, cell growth arrest and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the compounds of the instant invention described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the compounds of the instant invention described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the compounds of the instant invention described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the compounds of the instant invention described herein.

In another embodiment, the invention relates to an in vitro method of inducing terminal differentiation of tumor cells in a tumor comprising contacting the cells with an effective amount of any one or more of the compounds of the instant invention described herein.

In one embodiment, the methods of selectively inducing terminal differentiation, cell growth arrest and/or apoptosis of neoplastic cells, and of inhibiting HDAC will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the compounds of the instant invention described herein.

In a particular embodiment, the present invention relates to a method of selectively inducing terminal differentiation of neoplastic cells and thereby inhibiting proliferation of such cells in a subject. The method comprises administering to the subject an effective amount of one or more of the compounds of the instant invention described herein.

In another embodiment, the invention relates to a method of selectively inducing cell growth arrest of neoplastic cells and thereby inhibiting proliferation of such cells in a subject. The method comprises administering to the subject an effective amount of one or more of the compounds of the instant invention described herein.

In another embodiment, the invention relates to a method of selectively inducing apoptosis of neoplastic cells and thereby inhibiting proliferation of such cells in a subject. The method comprises administering to the subject an effective amount of one or more of the compounds of the instant invention described herein.

In another embodiment, the invention relates to a method of treating a patient having a tumor characterized by proliferation of neoplastic cells. The method comprises administering to the patient one or more of the compounds of the instant invention described herein. The amount of compound is effective to selectively induce terminal differentiation, induce cell growth arrest and/or induce apoptosis of such neoplastic cells and thereby inhibit their proliferation.

The invention is illustrated in the following generic schemes and the examples in the Experimental Details Section that follows. This section is set forth to aid in an understanding of the invention but is not intended to, and should not be construed to limit in any way the invention as set forth in the claims which follow thereafter.

SCHEME 1
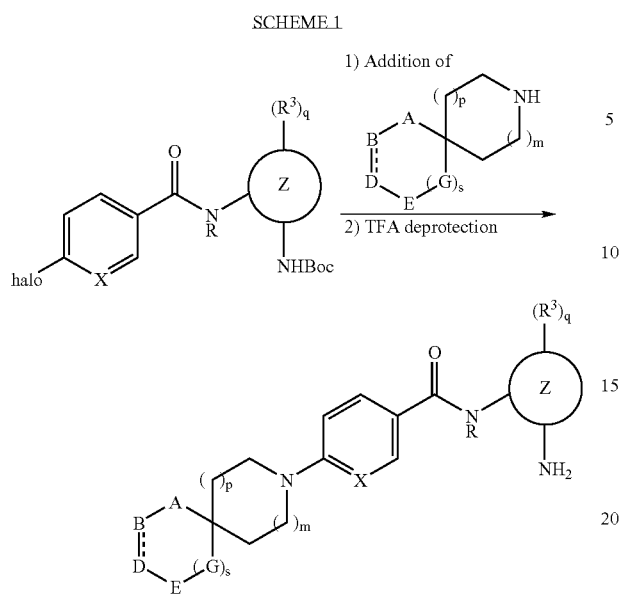
R is resin or H
SCHEME 2
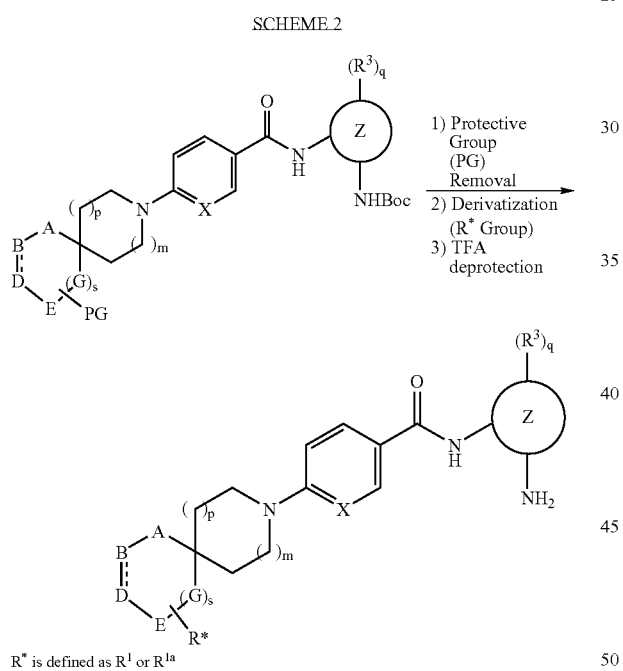
R* is defined as R¹ or R¹ᵃ
SCHEME 3
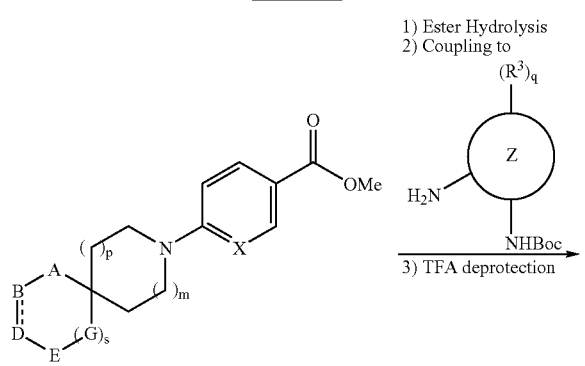
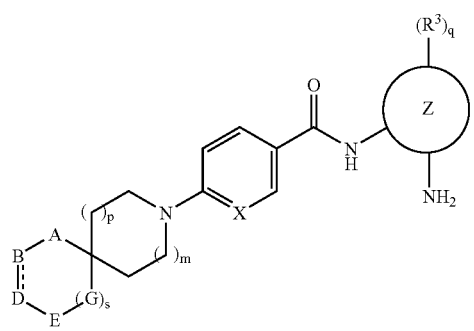
SCHEME 4
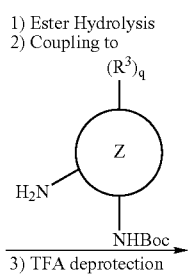
SCHEME 5
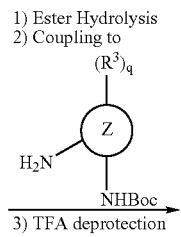

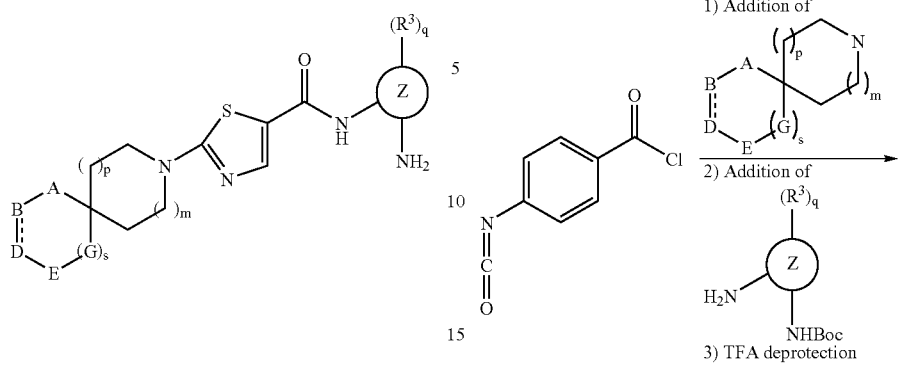

SCHEME 6

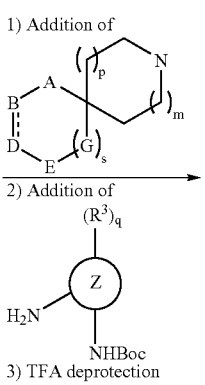

SCHEME 7

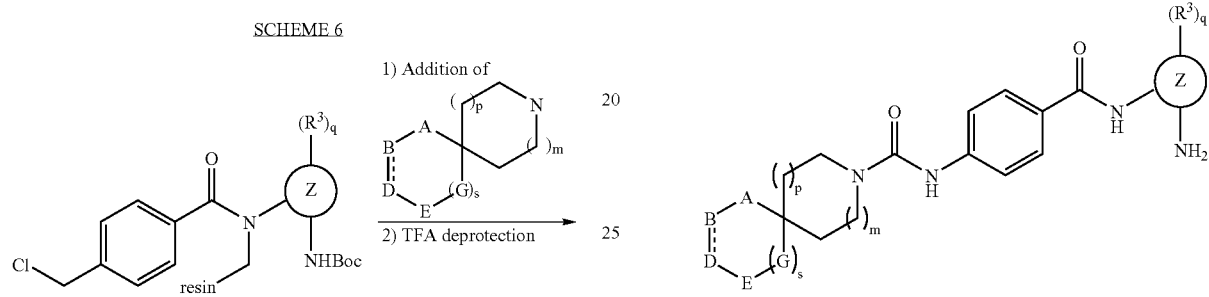

SCHEME 8

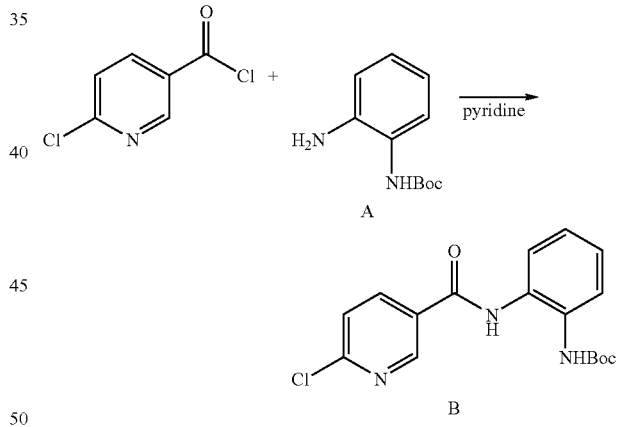

Experimental Section

Synthesis of Intermediates

Preparation of tert-Butyl (2-Aminophenyl)carbamate (A)

Intermediate A was prepared by the method described by Seto, C. T., et al., *Molecular self-assembly through hydrogen bonding: aggregation of five molecules to form a discrete supramolecular structure*, J. Am. Chem. Soc., 1993, vol. 115, 1321.

Prepration of tert-Butyl (2-{[(6-Chloropyridin-3-yl)carbonyl]amino}phenyl)carbamate (B)

To a solution of t-butyl (2-aminophenyl)carbamate A (10 g, 48.0 mmol) in $CH_2Cl_2$ (200 mL) was added 6-chloronicotinoyl chloride (8.5 g, 48.0 mmol). The reaction mixture was concentrated after 2 hours of stirring at room temperature and purified by flash chromatography (10-75% EtOAc/hexanes) to give the Boc-protected nicotinamide B confirmed by MS (ESI+): cal'd [M+Na]+ 370.1, obs'd 370.1.

NMR (600 MHz, CDCl3) δ 7.51 (d, J=3.2 Hz, 2H), 7.38 (t, J=5.6 Hz, 2H), 7.31 (m, 2H), 7.22 (s, 1H), 7.12 (dd, J=8.2, 2.1 Hz, 1H), 6.45 (br s, 1H), 1.51 (s, 9H); MS (EI) [M+Na]+ cal'd 285.1, obs'd 285.1.

Preparation of tert-Butyl (3-{[(6-Chloropyridin-3-yl)carbonyl]amino}biphenyl-4-yl)carbamate (D)

To a solution of t-butyl (3-aminobiphenyl-4-yl)carbamate C (2.06 g, 7.25 mmol) in pyridine (10 mL) was added 6-chloronicotinyl chloride (1.30 g, 7.39 mmol). After 4 hours of stirring at room temperature, the reaction mixture was filtered and the solvent concentrated. Formation of tert-butyl(3-{[(6-chloropyridin-3-yl)carbonyl]amino}biphenyl-4-yl)carbamate (D) was confirmed by $^1$H NMR (600 MHz, CD$_3$OD): δ 10.84 (s, 1H), 9.79 (s, 1H), 9.60 (s, 1H), 9.19-9.16 (m, 1H,) 8.59 (s, 1H), 8.57-8.55 (m, 2H), 8.43-8.40 (m, 2H), 8.34-8.30 (m, 1H), 8.25-8.21 (m, 2H), 8.12 (m, 1H), 2,22 (s, 9H).

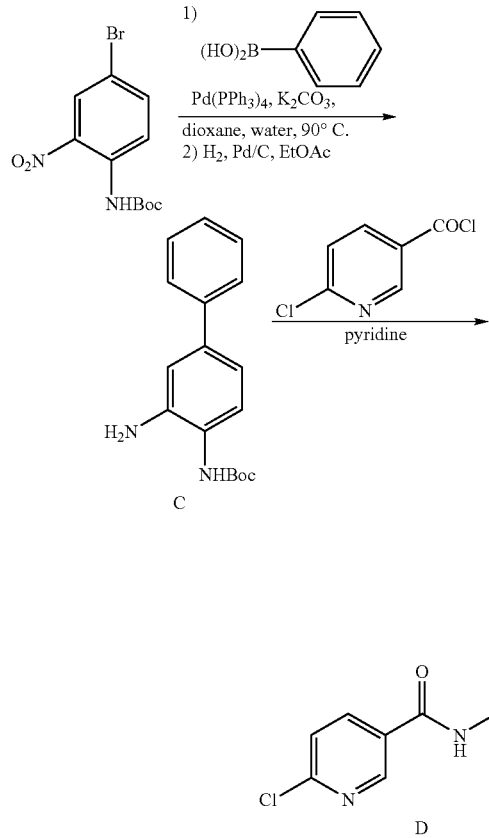

C

D

Preparation of tert-Butyl (3-Aminobiphenyl-4-yl)carbamate (C)

A mixture of N-Boc 4-bromo-2-nitroaniline (39.0 g, 123 mmol), phenylboronic acid (16.5 g, 135 mmol) and K$_2$CO$_3$ (34.1 g, 247 mmol) in 350 mL of dioxane and 150 mL of water was degassed by bubbling nitrogen through the mixture for 30 min. Next, Pd(PPh$_3$)$_4$ was added (4.32 g, 3.7 mmol) and the orange mixture was warmed to 78° C. for 18 h. Cooled and partitioned between ether (1500 mL) and water (400 mL). Filtered mixture through a pad of Celite (w/ether washes). Organic layer was separated, washed with brine, dried (MgSO$_4$) and concentrated to afford 44.1 g of reddish-orange solid. Recrystallization from EtOAc-hexanes (ca. 50 mL+1100 mL, respectively) afforded the bright orange solid N-Boc 4-phenyl-2-nitroaniline: MS (EI) [M+Na]+ cal'd 337.2, obs'd 337.2.

A solution of nitro compound (16.5 g, 52.5 mmol) in 400 mL of EtOAc evacuated and refilled with nitrogen (2×). Added 10% Pd/C (1.60 g), then evacuated and refilled with hydrogen (3×). Stirred under atmosphere of hydrogen overnight. Mixture was filtered through a pad of Celite (w/EtOAc, then CH$_2$Cl$_2$ washes) and concentrated to a pale orange solid. Stirred and warmed with ca. 800 mL of hexanes, then cooled and collected product (w/cold hexane washes). Dissolved resulting solid in CH$_2$Cl$_2$ and concentrated to provide the off-white solid N-BOC (3-aminobiphenyl-4-yl)amine C: $^1$H

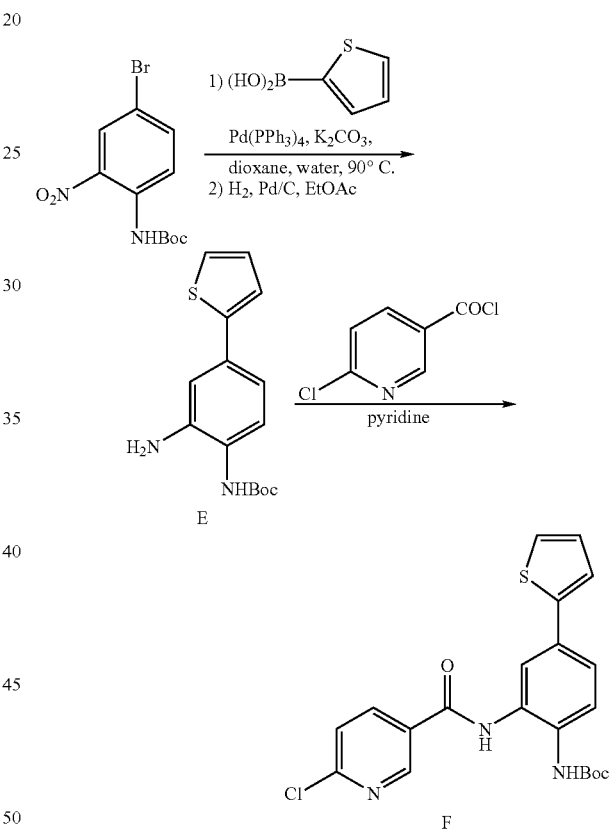

E

F

Preparation of tert-Butyl [2-Amino-4-(2-thienyl)phenyl]carbamate (E)

A mixture of tert-butyl (4-bromo-2-nitrophenyl)carbamate (19.4 g, 61.2 mmol), thiophene-2-boronic acid (9.94 g, 77.7 mmol) and K$_2$CO$_3$ (22.2 g, 160 mmol) in 60 mL of dioxane and 60 mL of water was degassed by bubbling nitrogen through the mixture for 30 min. Next, Pd[PPh$_3$]$_4$ (5.25 g, 4.53 mmol) was added and the heterogeneous mixture was warmed to reflux for 20 h. The mixture was cooled and diluted with ethyl acetate, washed with water and brine, dried (MgSO$_4$), and concentrated. The resulting solid was dissolved in diethylether (500 mL) and filtered through a pad of silica. The solvents were removed under reduced pressure to yield the yellow-brown solid: ¹H NMR (600 MHz, CDCl₃): δ 9.65 (s, 9H), 8.58 (d, J=8.8 Hz, 1H), 8.39 (d, J=2.1 Hz, 1H), 7.81 (dd, J=8.8, 1.8 Hz, 1 H), 7.32 (m, 2H), 7.09 (dd, J=5.3, 3.8 Hz, 1H), 1.54 (s, 9H); MS (ESI+): cal'd [M+Na]⁺ 343.1, obs'd 343.1.

A solution of N-BOC 2-nitro-4-(2-thienyl)aniline (18.0 g) in 350 mL of EtOAc was evacuated and refilled with nitrogen (2×). To the solution was added 10% Pd/C (4.46 g), and the reaction mixture was evacuated and refilled with hydrogen (2×). The black reaction mixture was stirred under an atmosphere of hydrogen overnight. The mixture was filtered through a pad of celite (with EtOAc then CH₂Cl₂ washes) and concentrated to provide a brownish-white solid. The solid was triturated with ether and filtered to provide the off-white tert-butyl [2-amino-4-(2-thienyl)phenyl]carbamate (E): ¹H NMR (600 MHz, DMSO-d₆) δ 8.31 (br, 1H), 7.41 (dd, J=5.0, 0.9 Hz, 1H), 7.26 (dd, J=3.5, 1.2 Hz, 1H), 7.23 (br d, J=8.5 Hz, 1H), 7.05 (dd, J=5.0, 3.5 Hz, 1H), 6.94 (d, J=2.1 Hz, 1H), 6.81 (dd, J=8.2, 2.1 Hz, 1H), 4.98 (s, 2H), 1.43 (s, 9H); MS (ESI+): cal'd [M+Na]⁺ 291.1, obs'd 291.1.

Preparation of tert-Butyl [2-{[(6-Chloropyridin-3-yl)carbonyl]amino}-4-(2-thienyl)phenyl]-carbamate (F)

A mixture of tert-butyl [2-amino-4-(2-thienyl)phenyl]carbamate (E) (600 mg, 2.07 mmol) and 6-chloronicotinyl chloride (380 mg, 2.16 mmol) in 5 mL of pyridine was stirred overnight, poured into EtOAc and washed with saturated NaHCO₃, dried (Na₂SO₄) and concentrated giving the BOC-protected chloronicotinamide (F): ¹H NMR (600 MHz, CD₃OD): δ 8.95 (d, J=2.3 Hz, 1H), 8.35 (dd, J=8.2 Hz, 2.3 Hz, 1H), 7.85 (br s, 1H), 7.62 (d, J=8.5 Hz, 1H), 7.55-7.51 (m, 2H), 7.37-7.35 (m, 2H), 7.07 (dd, J=5.0 Hz, 3.5 Hz, 1H), 4.59 (s, 1H), 1.49 (s, 9H); MS (ESI+): cal'd [M+Na]⁺ 452.1, obs'd 452.1.

Preparation of tert-Butyl [2-Amino-4-(3-thienyl)phenyl]carbamate (G) and tert-Butyl [2-{[(6-Chloropyridin-3-yl)carbonyl]amino}-4-(3-thienyl)phenyl]-carbamate (H)

Intermediates G and H were prepared from tert-butyl (4-bromo-2-nitrophenyl)carbamate using the methods employed for the preparation of intermediates E and F. Intermediate G: MS (ESI+): cal'd [M+Na]⁺ 291.1, obs'd 291.1. Intermediate H: MS (ESI+): cal'd [M+Na]⁺ 452.1, obs'd 452.1.

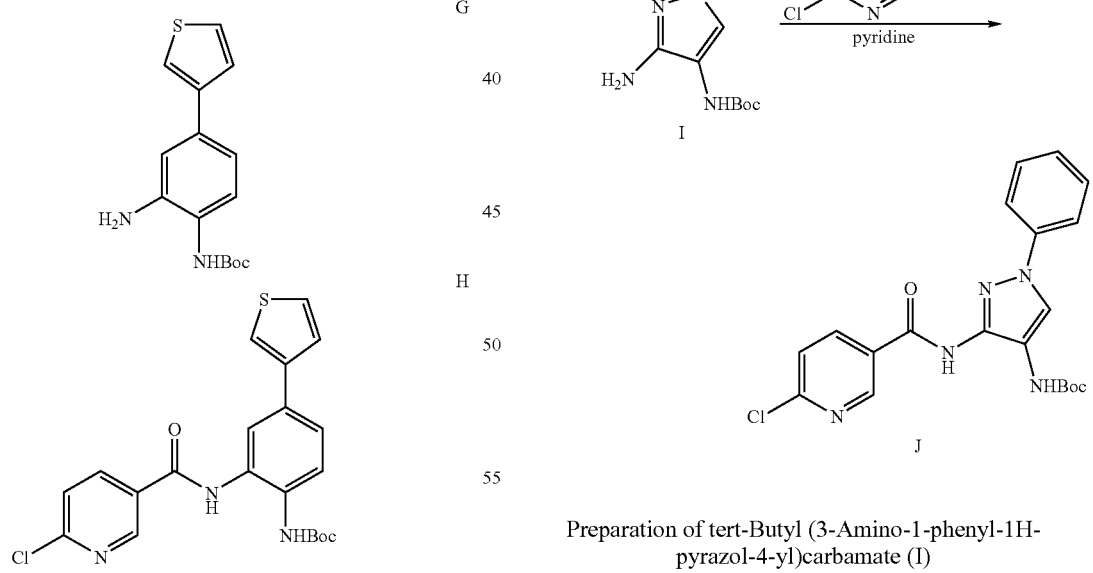

Preparation of tert-Butyl (3-Amino-1-phenyl-1H-pyrazol-4-yl)carbamate (I)

A solution of methyl 4-nitro-1H-pyrazole-3-carboxylate (54.0 g, 315.6 mmol), phenylboronic acid (77.0 g, 631.2 mmol), copper(II) acetate (86.0 g, 473.4 mmol) and pyridine (49.9 g, 631.2 mmol) in methylene chloride (600 mL) was stirred at ambient temperature open to air for 48 hours. The reaction was evaporated in vacuo, diluted with 1000 mL methylene chloride and filtered through a large plug of silica (washing with 2 liters methylene chloride). The solvent was evaporated in vacuo. ¹H NMR (CDCl₃) δ 8.61 (s, 1H), 7.73 (m, 2H), 7.50 (m, 3H), 4.02 (s, 3H).

A solution of methyl 4-nitro-1-phenyl-1H-pyrazole-3-carboxylate (78.1 g, 315.9 mmol) in THF (600 mL) was treated with 4M potassium hydroxide (79 mL, 316 mmol) dropwise and the solution was stirred at ambient temperature for 16 hours. The reaction was evaporated in vacuo and acidified with 6M HCl. After addition of water (500 mL) the solids were filtered off and dried to give the desired compound as a grayish solid. ¹H NMR (CD₃OD) δ 9.37 (bs, 1H), 7.88 (m, 2H), 7.59 (m, 2H), 7.44 (m, 1H).

A solution of 4-nitro-1-phenyl-1H-pyrazole-3-carboxylic acid (20.0 g, 85.8 mmol), triethylamine (36.0 mL, 257.3 mmol), and diphenylphosphoryl azide (37.8 g, 137.2 mmol) in dioxane (400 mL) and tert-butanol (200 mL) was heated to reflux for 16 hours. The reaction was evaporated to dryness in vacuo, diluted with methylene chloride (400 mL) and treated with trifluoroacetic acid (128 g, 857.7 mmol). The solution was stirred at ambient temperature for 16 hours. The reaction was evaporated in vacuo and the resulting oil diluted with hexanes (750 mL), ethyl acetate (150 mL) and methylene chloride (100 mL). The solids were filtered, washed with above solvent system (hexanes:ethyl acetate:methylene chloride 75:15:10), and dried to give the desired product as yellow solid. ¹H NMR (CDCl₃) δ 8.43 (s, 1H), 7.62 (m, 2H), 7.48 (m, 2H), 7.37 (m, 1H).

A solution of 4-nitro-1-phenyl-1H-pyrazol-3-amine (0.15 g, 0.74 mmol), di-tertbutyl dicarbonate (0.16 g, 0.74 mmol), triethylamine (0.19 g, 1.84 mmol) in methanol 20 mL was degassed with nitrogen and treated with platinum oxide (17 mg, 10 mol %). The solution was placed under a hydrogen atmosphere and stirred at ambient temperature for 2 hours. The reaction was then degassed with nitrogen, filtered through celite, washed with methanol and evaporated in vacuo. Flash chromatography (20-35% ethyl acetate/hexanes) gave the title compound as a purplish solid. ¹H NMR (CDCl₃) δ 7.85 (s, 1H), 7.51 (m, 2H), 7.37 (m, 2H), 7.18 (m, 1H), 6.40 (bs, 1H).

Prepartion of tert-Butyl (3-{[(6-Chloropyridin-3-yl)carbonyl]amino}-1-phenyl-1H-pyrazol-4-yl)-carbamate (J)

To a solution of t-butyl(3-amino-1-phenyl-1H-pyrazol-4-yl)carbamate (100 mg, 0.364 mmol) in pyridine (500 μL) was added 6-chloronicotinoyl chloride (53 mg, 0.304 mmol) in CH₂Cl₂ (2 mL). After 6 hours of stirring at room temperature, the reaction mixture was filtered and the solvent concentrated. Formation of t-butyl(3-{[(6-chloropyridin-3-yl)carbonyl]amino}-1-phenyl-1H-pyrazol-4-yl)carbamate (J) was confirmed by MS (ESI+): cal'd [M+H]⁺ 414.1, obs'd 414.1.

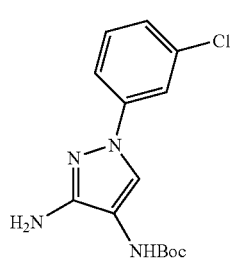

K

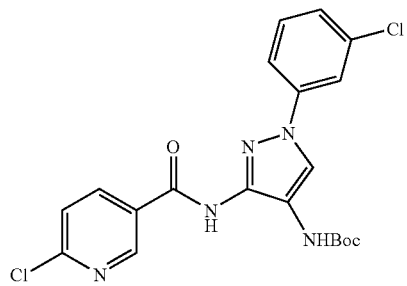

L

Preparation of tert-Butyl [3-Amino-1-(3-chlorophenyl)-1H-pyrazol-4-yl]carbamate (K) and tert-Butyl (1-(3-Chlorophenyl)-3-{[(6-chloropyridin-3-yl)carbonyl]amino}-1H-pyrazol-4-yl)-carbamate (L)

Intermediates K and L were prepared from 3-chlorophenylboronic acid in a manner analogous to steps used to prepare intermediates I and J. Intermediate K: MS (EI) calcd 309.1 (M⁺+H), found 309.1 (M⁺+H). Intermediate L: MS (EI) calcd 448.1 (M⁺+H), found 448.1 (M⁺+H).

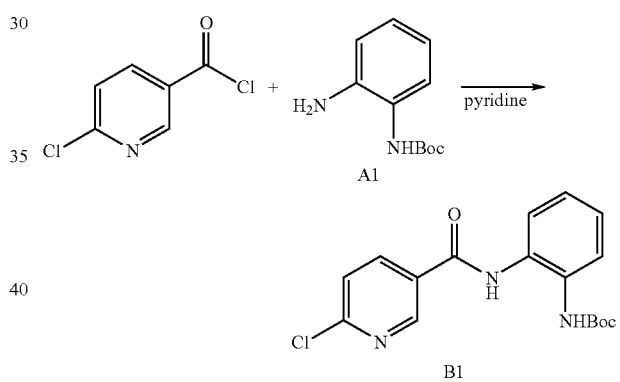

A1

B1

Preparation of tert-Butyl (2-Aminophenyl)carbamate (A1)

Intermediate A1 was prepared by the method described by Seto, C. T.; Mathias, J. P.; Whitesides, G. M. Molecular self-assembly through hydrogen bonding: aggregation of five molecules to form a discrete supramolecular structure. J. Am. Chem. Soc. 1993, 115, 1321.

Preparation of tert-Butyl (2-{[(6-Chloropyridin-3-yl)carbonyl]amino}phenyl)carbamate (B1)

To a solution of t-butyl (2-aminophenyl)carbamate A1 (10 g, 48.0 mmol) in CH₂Cl₂ (200 mL) was added 6-chloronicotinoyl chloride (8.5 g, 48.0 mmol). The reaction mixture was concentrated after 2 hours of stirring at room temperature and purified by flash chromatography (10-75% EtOAc/hexanes) to give the Boc-protected nicotinamide B1 confirmed by MS (ESI+): cal'd [M+Na]+370.1, obs'd 370.1.

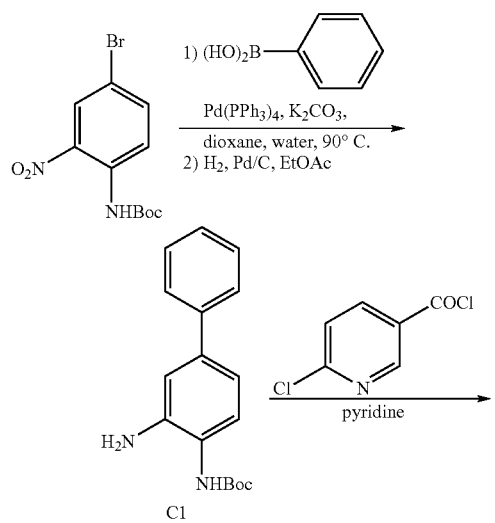

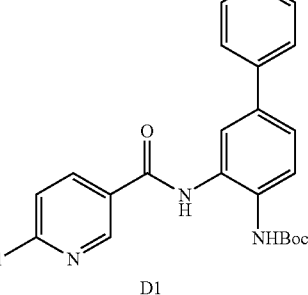

tert-Butyl (3-Aminobiphenyl-4-yl)carbamate (C1)

A mixture of N-Boc 4-bromo-2-nitroaniline (39.0 g, 123 mmol), phenylboronic acid (16.5 g, 135 mmol) and $K_2CO_3$ (34.1 g, 247 mmol) in 350 mL of dioxane and 150 mL of water was degassed by bubbling nitrogen through the mixture for 30 min. Next, $Pd(PPh_3)_4$ was added (4.32 g, 3.7 mmol) and the orange mixture was warmed to 78° C. for 18 h. Cooled and partitioned between ether (1500 mL) and water (400 mL). Filtered mixture through a pad of Celite (w/ether washes). Organic layer was separated, washed with brine, dried ($MgSO_4$) and concentrated to afford 44.1 g of reddish-orange solid. Recrystallization from EtOAc-hexanes (ca. 50 mL+1100 mL, respectively) afforded the bright orange solid N-Boc 4-phenyl-2-nitroaniline: MS (EI) $[M+Na]^+$ cal'd 337.2, obs'd 337.2.

A solution of nitro compound (16.5 g, 52.5 mmol) in 400 mL of EtOAc evacuated and refilled with nitrogen (2×). Added 10% Pd/C (1.60 g), then evacuated and refilled with hydrogen (3×). Stirred under atmosphere of hydrogen overnight. Mixture was filtered through a pad of Celite (w/EtOAc, then $CH_2Cl_2$ washes) and concentrated to a pale orange solid. Stirred and warmed with ca. 800 mL of hexanes, then cooled and collected product (w/cold hexane washes). Dissolved resulting solid in $CH_2Cl_2$ and concentrated to provide the off-white solid N-BOC (3-aminobiphenyl-4-yl)amine C1: $^1$H NMR (600 MHz, $CDCl_3$) δ 7.51 (d, J=3.2 Hz, 2H), 7.38 (t, J=5.6 Hz, 2H), 7.31 (m, 2H), 7.22 (s, 1H), 7.12 (dd, J=8.2, 2.1 Hz, 1H), 6.45 (br s, 1H), 1.51 (s, 9H); MS (EI) $[M+Na]^+$ cal'd 285.1, obs'd 285.1.

tert-Butyl (3-{[(6-Chloropyridin-3-yl)carbonyl]amino}biphenyl-4-yl)carbamate (D1)

To a solution of t-butyl (3-aminobiphenyl-4-yl)carbamate C1 (2.06 g, 7.25 mmol) in pyridine (10 mL) was added 6-chloronicotinyl chloride (1.30 g, 7.39 mmol). After 4 hours of stirring at room temperature, the reaction mixture was filtered and the solvent concentrated. Formation of tert-butyl (3-{[(6-chloropyridin-3-yl)carbonyl]amino}biphenyl-4-yl) carbamate (D1) was confirmed by $^1$H NMR (600 MHz, $CD_3OD$): δ 10.84 (s, 1H), 9.79 (s, 1H), 9.60 (s, 1H), 9.19-9.16 (m, 1H), 8.59 (s, 1H), 8.57-8.55 (m, 2H), 8.43-8.40 (m, 2H), 8.34-8.30 (m, 1H), 8.25-8.21 (m, 2H), 8.16-8.12 (m, 1H), 2.22 (s, 9H).

General Methods

EXAMPLE 1

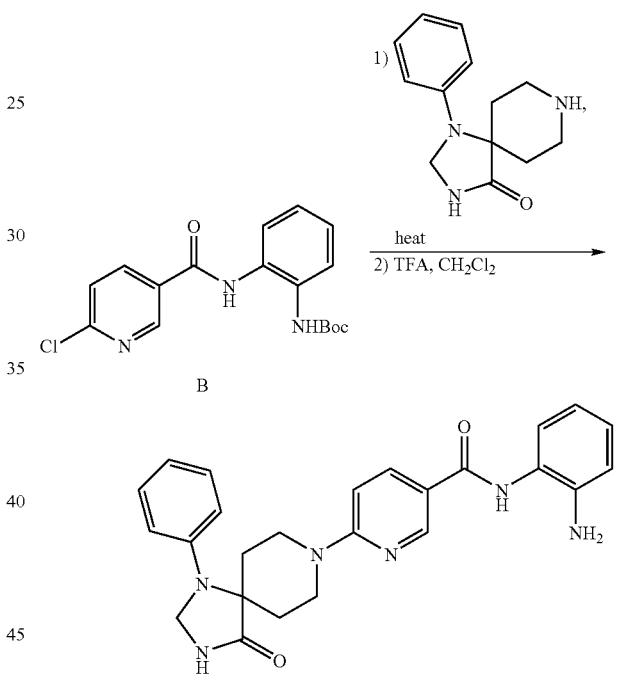

N-(2-Aminophenyl)-6-(4-oxo-1-phenyl-1,3,8-triazaspiro[4.5]dec-8-yl)nicotinamide A mixture of the Boc-protected chloronicotinamide B (125 mg, 0.359 mmol) and 1-phenyl-1,3,8-triazaspiro[4.5]decan-4-one (Acros Chemical Co.) (249 mg, 1.08 mmol) was heated at 85° C. for 4 hours in DMSO/PhMe (2 mL of a 1:1 solution). The reaction mixture was then diluted with EtOAc (25 mL) and washed with sat.'d aq. $NaHCO_3$ (1×5 mL) and brine (1×5 mL). The crude oil was purified by reverse phase flash chromatography (25% $MeCN/H_2O$ with 0.05% TFA to 100% MeCN with 0.05% TFA) and formation of the desired Boc-protected spiro-nicotinamide was confirmed by MS (ESI+): cal'd $[M+H]^+$ 543.3, exp. 543.2. The Boc-protected spiro-nicotinamide was treated with TFA (1.5 mL) in $CH_2Cl_2$ (3 mL) and after 20 minutes of stirring at room temperature, the reaction mixture was concentrated and purified by reverse-phase chromatography (15%-75% $MeCN/H_2O$ with 0.05% TFA). The appropriate fractions were combined, diluted with EtOAc (50 mL) and washed with sat.'d aq. NaHCO$_3$ (1×10 mL) and brine (1×5 mL). The organic layer was dried over Na$_2$SO$_4$, filtered, and concentrated to give the desired nicotinamide: $^1$H NMR (600 MHz, CD$_3$OD) δ 8.79, (s, 1H), 8.12 (d, J=7.0 Hz, 1H), 7.17 (d, J=7.6 Hz, 1H), 7.09-7.04 (m, 3H), 6.93-6.87 (m, 2H), 6.78-6.70 (m, 2H), 6.58 (d, J=7.9 Hz, 2H), 4.68 (s, 2H), 4.40-4.34 (br m, 2H), 3.80 (dt, J=12.9 Hz, 3.2 Hz, 2H), 2.63-2.56 (m, 2H), 1.75 (d, J=14.1 Hz, 2H); MS (ESI+): cal'd [M+H]$^+$ 443.2, obs'd 443.2.

The compounds described in the following table were prepared by methods analogous to those synthetic methods described above, but using the appropriate starting materials.

TABLE 1

| Compound | Forms Prepared | Chemical Name | MS Data |
|---|---|---|---|
|  | TFA | N-(2-aminophenyl)-6-(7-benzyl-2,7-diazaspiro[4.4]non-2-yl)nicotinamide | Cal'd [M$^+$ + 1] 428.2, Obs'd 428.3 |
|  | neutral | N-(2-aminophenyl)-6-(7-phenyl-2,7-diazaspiro[4.4]non-2-yl)nicotinamide | Cal'd [M$^+$ + 1] 414.2, Obs'd 414.2 |
|  | neutral | N-(2-aminophenyl)-6-[7-(2-chloro phenyl)-2,7-diazaspiro[4.4]non-2-yl]nicotinamide | Cal'd [M$^+$ + 1] 448.2, Obs'd 448.2 |
|  | neutral | N-(2-aminophenyl)-6-[7-(3-chloro phenyl)-2,7-diazaspiro[4.4]non-2-yl]nicotinamide | Cal'd [M$^+$ + 1] 448.2, Obs'd 448.2 |
|  | neutral | N-(2-aminophenyl)-6-[7-(4-chloro phenyl)-2,7-diazaspiro[4.4]non-2-yl]nicotinamide | Cal'd [M$^+$ + 1] 448.2, Obs'd 448.2 |

TABLE 1-continued

| Compound | Forms Prepared | Chemical Name | MS Data |
|---|---|---|---|
| | neutral | 7-(5-{[(2-aminophenyl)amino]carbonyl}pyridin-2-yl)-N-phenyl-1-oxa-2,7-diazaspiro[4.4]non-2-ene-3-carboxamide | Cal'd [M⁺ + 1] 457.2, Obs'd 457.2 |
| | neutral | N-(2-aminophenyl)-6-[1-(3-methylphenyl)-2-oxo-1,3,8-triazaspiro[4.5]dec-8-yl]nicotinamide | Cal'd [M⁺ + 1] 457.2, Obs'd 457.1 |
| | neutral | N-(2-aminophenyl)-6-{3-[2-(4-fluorophenyl)ethyl]-1-oxa-8-azaspiro[4.5]dec-8-yl}nicotinamide | Cal'd [M⁺ + 1] 475.2, Obs'd 475.2 |
| | neutral | N-(2-aminophenyl)-6-[3-(4-fluorobenzyl)-2-oxo-1-oxa-8-azaspiro[4.5]dec-8-yl]nicotinamide | Cal'd [M⁺ + 1] 475.2, Obs'd 475.2 |

EXAMPLE 2

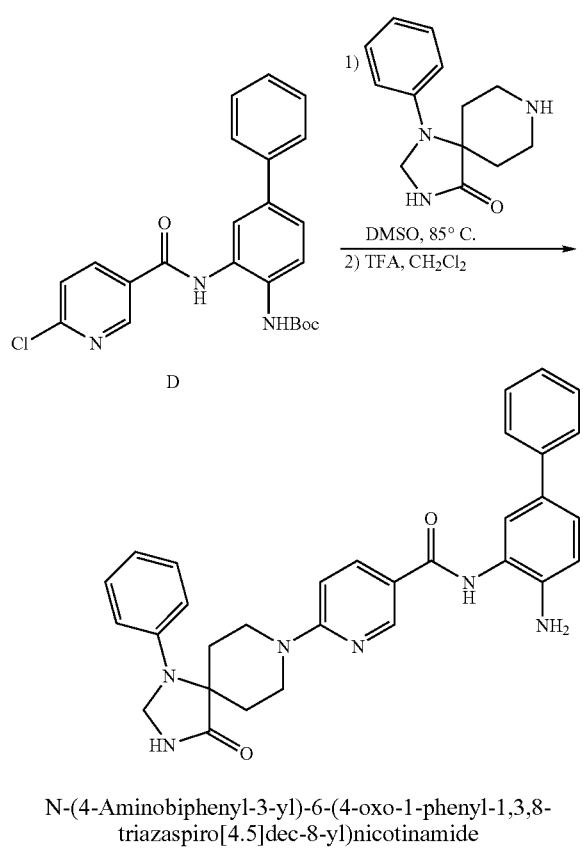

N-(4-Aminobiphenyl-3-yl)-6-(4-oxo-1-phenyl-1,3,8-triazaspiro[4.5]dec-8-yl)nicotinamide To a solution of 1-phenyl-1,3,8-triazaspiro[4.5]decan-4-one (Acros Chemical Co.) (182 mg, 0.787 mmol) in DMSO (2 mL) was added t-butyl(3-{[(6-chloropyridin-3-yl)carbonyl]amino}biphenyl-4-yl)carbamate D (133 mg, 0.315 mmol). The reaction mixture was heated at 85° C. for 6 hours, cooled to room temperature, diluted with EtOAc (25 mL) and then washed with sat.'d aq. NaHCO$_3$ (1×5 mL) and brine (1×5 mL). The organic layer was dried over Na$_2$SO$_4$, filtered, concentrated, and the crude residue purified by flash chromatography (10-100% EtOAc/hexanes). Formation of the Boc-protected biphenyl spiro-nicotinamide was confirmed by MS (ESI+): cal'd [M+H]$^+$ 619.3, exp. 619.3. To a solution of the Boc-protected biphenyl spiro-nicotinamide in CH$_2$Cl$_2$ (3 mL) was added TFA (1 mL). The reaction mixture was concentrated after 20 minutes of stirring at room temperature and the crude residue was purified by reverse-phase chromatography (10-75% MeCN/H$_2$O with 0.05% TFA). The appropriate fractions were combined, diluted with EtOAc (50 mL) and washed with sat.'d aq. NaHCO$_3$ (1×10 mL) and brine (1×5 mL). The organic layer was dried over Na$_2$SO$_4$, filtered, and concentrated to give the desired biphenyl spiro-nicotinamide: $^1$H NMR (600 MHz, CD$_3$OD): δ 8.81 (d, J=2.1 Hz, 1H), 8.16 (dd, J=8.8 Hz, 2.3 Hz, 1H), 7.55 (dd, J=8.1 Hz, 1.1 Hz, 2H), 7.48 (d, J=2.1 Hz, 1H), 7.38-7.35 (m, 3H), 7.24-7.22 (m, 1H), 7.09-7.06 (m, 2H), 6.96 (dd, J=10.8 Hz, 8.8 Hz, 2H), 6.73 (t, J=7.3 Hz, 1H), 6.60 (d, J=7.92 Hz, 2H), 4.90 (s, 2H), 4.41-4.38 (br m, 2H), 3.82 (dt, J=12.8 Hz, 3.1 Hz, 2H), 2.64-2.58 (m, 2H), 1.77 (d, J=14.1 Hz, 2H); MS (ESI+): cal'd [M+H]$^+$ 519.3, obs'd 519.3.

The compounds described in the following table were prepared by methods analogous to those synthetic methods described above, but using the appropriate starting materials.

TABLE 2

| Compound | Forms Prepared | Chemical Name | MS Data |
|---|---|---|---|
|  | neutral | 7-(5-{[(4-aminobiphenyl-3-yl)amino]carbonyl}pyridin-2-yl)-N-(2-phenylethyl)-1-oxa-2,7-diazaspiro[4.4]non-2-ene-3-carboxamide | Cal'd [M$^+$ + 1] 561.3, Obs'd 561.3 |

TABLE 2-continued

| Compound | Forms Prepared | Chemical Name | MS Data |
|---|---|---|---|
| | neutral | N-(4-aminobiphenyl-3-yl)-6-(7-benzyl-2,7-diazaspiro[4.4]non-2-yl)nicotinamide | Cal'd [M⁺ + 1] 504.3, Obs'd 504.3 |
| | neutral | N-(4-aminobiphenyl-3-yl)-6-(7-phenyl-2,7-diazaspiro[4.4]non-2-yl)nicotinamide | Cal'd [M⁺ + 1] 490.3, Obs'd 490.3 |
| | neutral, HCl | 6-(7-acetyl-2,7-diazaspiro[4.4]non-2-yl)-N-(4-aminobiphenyl-3-yl)nicotinamide | Cal'd [M⁺ + 1] 456.2, Obs'd 456.2 |

EXAMPLE 3

N-[2-Amino-5-(2-thienyl)phenyl]-6-(2,8-diazaspiro[4.5]dec-8-yl)nicotinamide

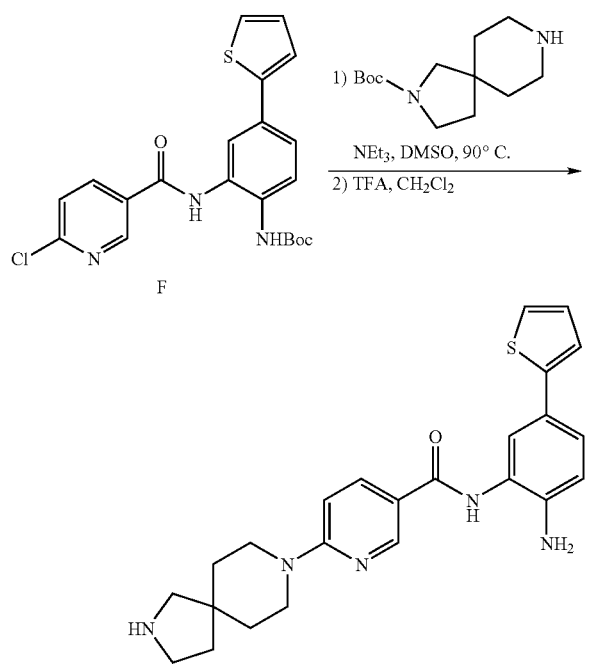

2-Thiophenyl Boc-chloronicotinamide F (60 mg, 0.14 mmol) was dissolved in 1 mL of DMSO and treated with NEt$_3$ (0.100 mL) and tert-butyl 2,8-diazaspiro[4.5]decane-2-carboxylate (50 mg, 0.21 mmol). The mixture was stirred at 90° C. for 18 h, partitioned between EtOAc and saturated NaHCO$_3$, dried (Na$_2$SO$_4$), filtered and concentrated. The residue was dissolved in 1 mL of 1:1 TFA/CH$_2$Cl$_2$, stirred for 5 h and concentrated. Reverse-phase chromatography (10-100% MeCN/water with 0.05% TFA) followed by neutralization with EtOAc/sat'd NaHCO$_3$ extraction and drying (Na$_2$SO$_4$) gave the target spirocyclic compound: $^1$H NMR (600 MHz, CD$_3$OD): δ 8.73 (s, 1H), 8.06 (dd, J=8.8, 2.1 Hz, 1H), 7.45 (s, 1H), 7.33 (dd, J=8.2, 2.1 Hz, 1H), 7.21 (dd, J=5.0, 1.2 Hz, 1H), 7.19 (dd, J=3.5, 0.9 Hz, 1H), 7.00 (dd, J=5.0, 3.5 Hz, 1H), 6.88 (d, J=8.5 Hz, 1H), 6.81 (d, J=9.1 Hz, 1H), 3.72 (m, 2H), 3.62 (m, 2H), 2.94 (t, J=7.3 Hz, 2H), 2.71 (s, 2H), 1.68 (t, J=7.0 Hz, 2H), 1.60 (m, 4H); MS (ESI+): cal'd [M+H]$^+$ 434.2, obs'd 434.2.

The compounds described in the following table were prepared by methods analogous to those synthetic methods described above, but using the appropriate starting materials.

TABLE 3

| Compound | Forms Prepared | Chemical Name | MS Data |
|---|---|---|---|
|  | neutral | N-(2-aminophenyl)-6-(2,8-diazaspiro[4.5]dec-8-yl)nicotinamide | Cal'd [M$^+$ + 1] 352.2, Obs'd 352.2 |
|  | neutral | N-[2-amino-5-(3-thienyl)phenyl]-6-(2,8-diazaspiro[4.5]dec-8-yl)nicotinamide | Cal'd [M$^+$ + 1] 434.2, Obs'd 434.2 |

TABLE 3-continued

| Compound | Forms Prepared | Chemical Name | MS Data |
|---|---|---|---|
| 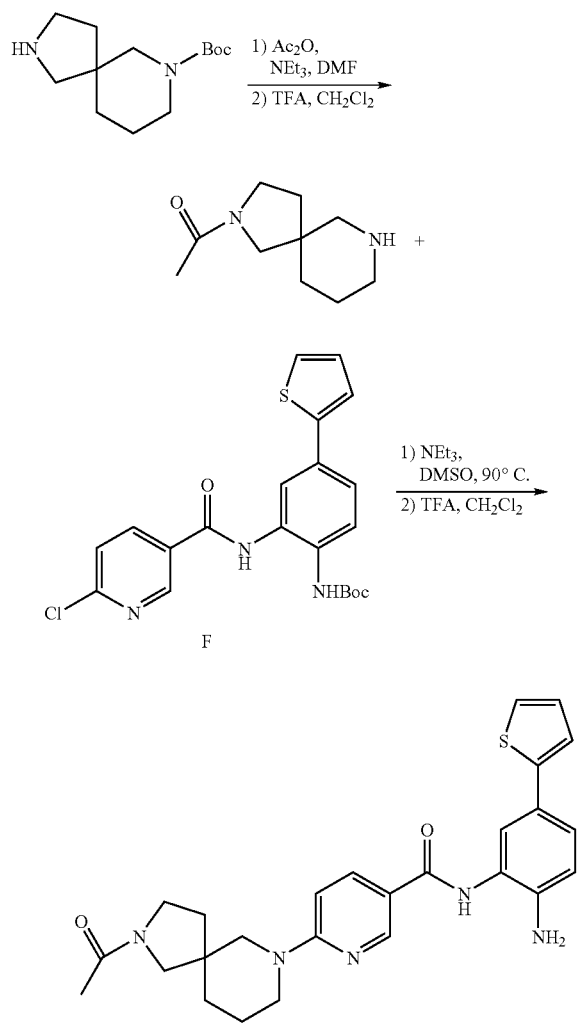 | neutral | N-(4-aminobiphenyl-3-yl)-6-(2,8-diazaspiro[4.5]dec-8-yl)nicotinamide | Cal'd [M+ + 1] 428.2, Obs'd 428.3 |

EXAMPLE 4

6-(2-Acetyl-2,7-diazaspiro[4.5]dec-7-yl)-N-[2-amino-5-(2-thienyl)phenyl]-nicotinamide A mixture of tert-butyl 2,7-diazaspiro[4.5]decane-7-carboxylate (200 mg, 0.833 mmol), NEt$_3$ (0.200 mL, 1.44 mmol) and Ac$_2$O (0.100 mL, 1.06 mmol) in 1 mL of DMF was stirred for 5 h. The reaction mixture was partitioned between EtOAc and saturated NaHCO$_3$, the organic layer was dried (Na$_2$SO$_4$), filtered and concentrated. The mixture was treated with 1:1 TFA/CH$_2$Cl$_2$, stirred for 1 h and concentrated. The oily residue was azeotroped with methanol and placed under high vacuum overnight. The resulting thick residue was then dissolved in 2 mL of DMSO containing tert-butyl [2-{[(6-chloropyridin-3-yl)carbonyl]amino}-4-(2-thienyl)phenyl]carbamate (100 mg, 0.233 mmol), treated with NEt$_3$ (0.50 mL) and stirred at 90° C. for 12 h. The reaction mixture was partitioned between EtOAc and saturated NaHCO$_3$, the organic layer was dried (Na$_2$SO$_4$), filtered and concentrated. Finally, the residue was dissolved in 1:1 TFA/CH$_2$Cl$_2$, stirred for 1 h and concentrated. Reverse-phase chromatography (10-100% MeCN/water with 0.05% TFA) followed by TFA removal by EtOAc/saturated extraction and drying (Na$_2$SO$_4$) gave the title compound: $^1$H NMR (600 MHz, CD$_3$OD): δ 8.69 and 8.71 (2s, 1H), 8.05 and 8.07 (2d, J=9.1 Hz, 1H), 7.47 (s, 1H), 7.35 (d, J=8.2 Hz, 1H), 7.23 (d, J=5.0 Hz, 1H), 7.20 (d, J=3.5 Hz, 1H), 7.01 (dd, J=5.0, 3.5 Hz, 1H), 6.91 (d, J=8.2 Hz, 1H), 6.82 (dd, J=9.1, 6.2 Hz, 1H), 3.75 (m, 2H), 3.65 (m, 1H), 3.52 (m, 3H), 3.03 and 3.19 (2d, J=12.3 Hz, 1H), 2.00 and 2.04 (2s, 3H), 1.6-1.9 (m, 6H); MS (ESI+): cal'd [M+H]+ 476.2, obs'd 476.2.

The compounds described in the following table were prepared by methods analogous to those synthetic methods described above, but using the appropriate starting materials.

TABLE 4

| Compound | Forms Prepared | Chemical Name | MS Data |
|---|---|---|---|
|  | TFA | benzyl 7-(5-{[(2-aminophenyl)amino]carbonyl}pyridin-2-yl)-2,7-diazaspiro[4.5]decane-2-carboxylate | Cal'd [M+ + 1] 486.2, Obs'd 486.3 |
|  | neutral | benzyl 7-(5-{[(4-aminobiphenyl-3-yl)amino]carbonyl}pyridin-2-yl)-2,7-diazaspiro[4.5]decane-2-carboxylate | Cal'd [M+ + 1] 562.3, Obs'd 562.3 |
|  | neutral | N-(4-aminobiphenyl-3-yl)-6-(2-benzoyl-2,7-diazaspiro[4.5]dec-7-yl)nicotinamide | Cal'd [M+ + 1] 532.3, Obs'd 532.3 |
|  | neutral | N-(4-aminobiphenyl-3-yl)-6-(2-pyrimidin-2-yl-2,7-diazaspiro[4.5]dec-7-yl)nicotinamide | Cal'd [M+ + 1] 506.3, Obs'd 506.3 |

TABLE 4-continued

| Compound | Forms Prepared | Chemical Name | MS Data |
|---|---|---|---|
| | neutral | 6-(2-acetyl-2,7-diazaspiro[4.5]dec-7-yl)-N-(4-aminobiphenyl-3-yl)nicotinamide | Cal'd [M+ + 1] 470.3, Obs'd 470.3 |
| | neutral | ethyl 7-(5-{[(4-aminobiphenyl-3-yl)amino]carbonyl}pyridin-2-yl)-2,7-diazaspiro[4.5]decane-2-carboxylate | Cal'd [M+ + 1] 500.3, Obs'd 500.3 |
| | neutral | 7-(5-{[(4-aminobiphenyl-3-yl)amino]carbonyl}pyridin-2-yl)-N-ethyl-2,7-diazaspiro[4.5]decane-2-carboxamide | Cal'd [M+ + 1] 499.3, Obs'd 499.3 |
| | neutral | N-[2-amino-5-(2-thienyl)phenyl]-6-(2-pyrimidin-2-yl-2,7-diazaspiro[4.5]dec-7-yl)nicotinamide | Cal'd [M+ + 1] 512.2, Obs'd 512.2 |

TABLE 4-continued

| Compound | Forms Prepared | Chemical Name | MS Data |
|---|---|---|---|
| (structure) | neutral | ethyl 7-[5-({[2-amino-5-(2-thienyl)phenyl]amino}carbonyl)pyridin-2-yl]-2,7-diazaspiro[4.5]decane-2-carboxylate | Cal'd [M+ + 1] 506.2, Obs'd 506.2 |
| (structure) | neutral | 7-[5-({[2-amino-5-(2-thienyl)phenyl]amino}carbonyl)pyridin-2-yl]-N-ethyl-2,7-diazaspiro[4.5]decane-2-carboxamide | Cal'd [M+ + 1] 505.2, Obs'd 505.2 |

EXAMPLE 5

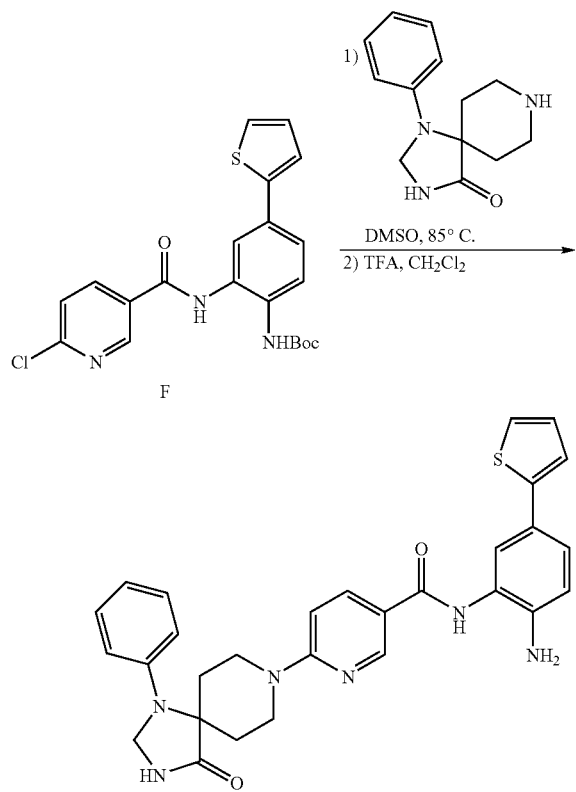

N-[2-Amino-5-(2thienyl)phenyl]-6-(4-oxo-1-phenyl-1,3,8-triazaspiro[4.5]dec-8-yl)nicotinamide To a solution of 1-phenyl-1,3,8-triazaspiro[4.5]decan-4-one (Acros Chemical Co.) (534 mg, 2.31 mmol) in DMSO (1.5 mL) was added t-butyl[2-{[(6-chloropyridin-3-yl)carbonyl]amino}-4-(2-thienyl)phenyl]carbamate (331 mg, 0.77 mmol). The reaction mixture was heated at 85° C. for 10 hours, cooled to room temperature, diluted with EtOAc (50 mL) and then washed with sat.'d aq. NaHCO$_3$ (1×10 mL) and brine (1×5 mL). The organic layer was dried over Na$_2$SO$_4$, filtered, concentrated, and the crude residue purified by flash chromatography (10-100% EtOAc/hexanes). Formation of the Boc-protected biaryl spiro-nicotinamide was confirmed by MS (ESI+): cal'd [M+H]+625.3, exp. 625.3. To a solution of the Boc-protected biaryl spiro-nicotinamide in CH$_2$Cl$_2$ (4 mL) was added TFA (2 mL). The reaction mixture was concentrated after 20 minutes of stirring at room temperature and the crude residue was purified by reverse-phase chromatography (10-75% MeCN/H$_2$O with 0.05% TFA). The appropriate fractions were combined, diluted with EtOAc (50 mL) and washed with sat.'d aq. NaHCO$_3$ (1×10 mL) and brine (1×5 mL). The organic layer was dried over Na$_2$SO$_4$, filtered, and concentrated to give the desired biaryl spiro-nicotinamide: $^1$H NMR (600 MHz, DMSO-d$_6$): δ 9.56 (s, 1H), 8.78 (d, J=2.6 Hz, 2H), 8.12 (dd, J=9.1 Hz, 2.3 Hz, 1H), 7.46 (d, J=2.1 Hz, 1H), 7.35-7.31 (m, 1H), 7.29-7.26 (m, 1H), 7.24-7.22 (m, 1H), 7.07-7.01 (m, 3H), 6.97 (d, J=9.1 Hz, 1H), 6.79 (d, J=8.2 Hz, 1H), 6.65 (t, J=7.3 Hz, 1H), 6.48 (d, J=8.2 Hz, 1H), 4.58 (s, 2H), 4.38-4.32 (br m, 2H), 3.68 (dt, J=12.9 Hz, 3.2 Hz, 2H), 2.50-2.42 (m, 2H), 1.66 (d, J=14.1 Hz, 2H); MS (ESI+): cal'd [M+H]+ 525.2, obs'd 525.2.

The compounds described in the following table were prepared by methods analogous to those synthetic methods described above, but using the appropriate starting materials.

TABLE 5

| Compound | Forms Prepared | Chemical Name | MS Data |
|---|---|---|---|
| (structure) | neutral | 6-(7-acetyl-2,7-diazaspiro[4.4]non-2-yl)-N-[2-amino-5-(2-thienyl)phenyl]nicotinamide | Cal'd [M+ + 1] 462.2, Obs'd 462.1 |
| (structure) | neutral | 6-(7-acetyl-2,7-diazaspiro[4.4]non-2-yl)-N-[2-amino-5-(3-thienyl)phenyl]nicotinamide | Cal'd [M+ + 1] 462.2, Obs'd 462.2 |

EXAMPLE 6

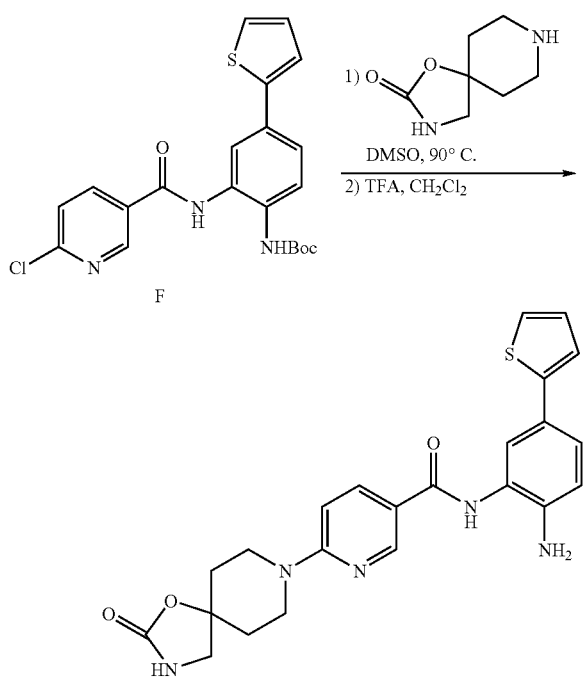

N-[2-Amino-5-(2-thienyl)phenyl]-6-(2-oxo-1-oxa-3,8-diazaspiro[4.5]dec-8-yl)nicotinamide 1-Oxa-3,8-diazaspiro[4.5]decan-2-one was prepared from Boc-piperidone as described by Smith, P. W. et al., New Spiropiperidines as Potent and Selective Non-Peptide Tachykinin NK2 Receptor Antagonists. *J. Med. Chem.* 1995, 38, 3772.

A solution of 1-oxa-3,8-diazaspiro[4.5]decan-2-one (390 mg, 1.44 mmol, mono-TFA salt), $NEt_3$ (1.00 mL, 7.19 mmol), t-butyl[2-{[(6-chloropyridin-3-yl)carbonyl]amino}-4-(2-thienyl)phenyl]carbamate (400 mg, 0.93 mmol) in 5 mL of DMSO was stirred at 90° C. for 21 hours. The crude reaction mixture was cooled and partitioned between $CH_2Cl_2$ and 2 N HCl. Next, the organic layer was washed with water, dried ($Na_2SO_4$), filtered and concentrated. The oily residue was dissolved in 3:1 $CH_2Cl_2$/TFA (4 mL) and stirred for 1 hour. The mixture was concentrated and purified by reverse-phase chromatography (30-100% MeCN/water containing 0.05% TFA). The product was neutralized by partitioning between $CHCl_3$/methanol and 2 N NaOH, the organic layer was dried ($Na_2SO_4$) and concentrated giving the target compound: $^1$H NMR (600 MHz, DMSO-$d_6$): δ 9.53 (s, 1H), 8.74 (d, J=2.3 Hz, 1H), 8.08 (dd, J=9.1, 2.6 Hz, 1H), 7.54 (s, 1H), 7.43 (d, J=2.1 Hz, 1H), 7.33 (dd, J=5.0, 1.2 Hz, 1H), 7.25 (dd, J=8.2, 2.3 Hz, 1H), 7.21 (dd, J=3.8, 1.2 Hz, 1H), 7.02 (dd, J=5.0, 3.5 Hz, 1H), 6.96 (d, J=8.8 Hz, 1H), 6.77 (d, J=8.2 Hz, 1H), 5.12 (br s, 2H), 3.92 (m, 2H), 3.53 (m, 2H), 3.27 (s, 2H), 1.71-1.83 (m, 4H); MS (ESI+): cal'd [M+H]+ 450.2, obs'd 450.1.

The compounds described in the following table were prepared by methods analogous to those synthetic methods described above, but using the appropriate starting materials.

TABLE 6

| Compound | Forms Prepared | Chemical Name | MS Data |
|---|---|---|---|
| (structure) | neutral | N-[2-amino-5-(3-thienyl)phenyl]-6-(2-oxo-1-oxa-3,8-diazaspiro[4.5]dec-8-yl)nicotinamide | Cal'd [M$^+$ + 1] 450.2, Obs'd 450.2 |
| (structure) | neutral | N-[2-amino-5-(2-thienyl)phenyl]-6-(3-methyl-2-oxo-1-oxa-3,8-diazaspiro[4.5]dec-8-yl)nicotinamide | Cal'd [M$^+$ + 1] 464.2, Obs'd 462.2 |
| (structure) | neutral, TFA | N-[2-amino-5-(2-thienyl)phenyl]-6-(2-oxo-1-oxa-3,8-diazaspiro[4.5]dec-8-yl)nicotinamide | Cal'd [M$^+$ + 1] 450.2, Obs'd 450.2 |

TABLE 6-continued

| Compound | Forms Prepared | Chemical Name | MS Data |
|---|---|---|---|
| (structure) | neutral | N-(4-aminobiphenyl-3-yl)-6-(3-methyl-2-oxo-1-oxa-3,8-diazaspiro[4.5]dec-8-yl)nicotinamide | Cal'd [M⁺ + 1] 458.2, Obs'd 458.2 |
| (structure) | HCl | N-(4-aminobiphenyl-3-yl)-6-(2-oxo-1-oxa-3,8-diazaspiro[4.5]dec-8-yl)nicotinamide | Cal'd [M⁺ + 1] 444.2, Obs'd 444.2 |

EXAMPLE 7

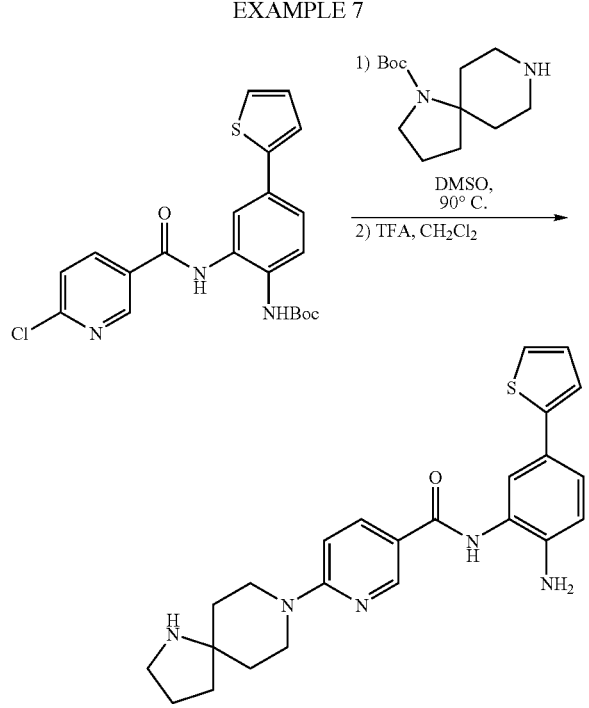

N-[2-Amino-5-(2-thienyl)phenyl]-6-(1,8-diazaspiro[4.5]dec-8-yl)nicotinamide

A mixture of tert-butyl [2-{[(6-chloropyridin-3-yl)carbonyl]amino}-4-(2-thienyl)phenyl]carbamate (200 mg, 0.47 mmol) and tert-butyl 1,8-diazaspiro[4.5]decane-1-carboxylate (200 mg, 0.83 mmol) in 5 mL of DMSO was treated with Et$_3$N (0.104 mL) and stirred at 90° C. for 12 h. The reaction mixture was partitioned between EtOAc and saturated NaHCO$_3$, the organic layer was dried (MgSO$_4$), filtered and concentrated. Finally, the residue was dissolved in 1:1 TFA/CH$_2$Cl$_2$, stirred for 1 h and concentrated. Reverse-phase chromatography (10-100% MeCN/water with 0.05% TFA) followed by neutralization with EtOAc/sat'd NaHCO$_3$ extraction and drying (MgSO$_4$) gave the target spirocyclic compound: $^1$H NMR (600 MHz, DMSO-d$_6$): δ 9.48 (s, 1H), 8.72 (d, J=1.8, Hz, 1H), 8.05 (dd, J=8.4, 1.8 Hz, 1H), 7.42 (d, J=1.8 Hz, 1H), 7.33 (d, J=5.4 Hz, 1H), 7.26 (dd, J=8.4, 2.4 Hz, 1H), 7.21 (d, J=3 Hz, 1H), 7.02 (t, J=4.2 Hz, 1H), 6.91 (d, J=9.6, 1H), 6.77 (d, J=9.0, 1H), 5.10 (s, 2H), 3.80 (br m, 2H), 3.57 (br m, 2H), 2.96 (br m, 2H), 1.79 (br m, 2H), 1.58 (br m, 4H); MS (ESI+): cal'd [M+H]⁺ 434.2, obs'd 434.2.

The compounds described in the following table were prepared by methods analogous to those synthetic methods described above, but using the appropriate starting materials.

TABLE 7
| Compound | Forms Prepared | Chemical Name | MS Data |
|---|---|---|---|
| 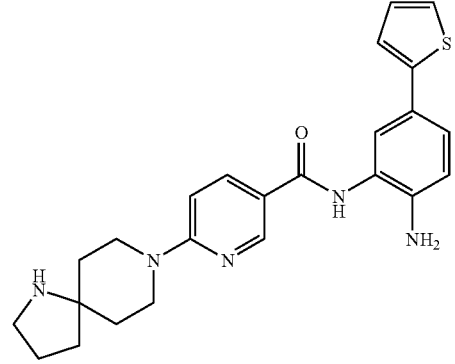 | neutral | N-[2-amino-5-(2-thienyl)phenyl]-6-(1,8-diazaspiro[4.5]dec-8-yl)nicotinamide | Cal'd [M$^+$ + 1] 434.2, Obs'd 434.2 |
| 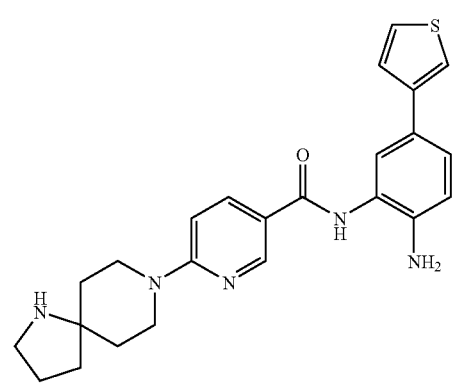 | neutral | N-[2-amino-5-(3-thienyl)phenyl]-6-(1,8-diazaspiro[4.5]dec-8-yl)nicotinamide | Cal'd [M$^+$ + 1] 434.2, Obs'd 434.1 |
| 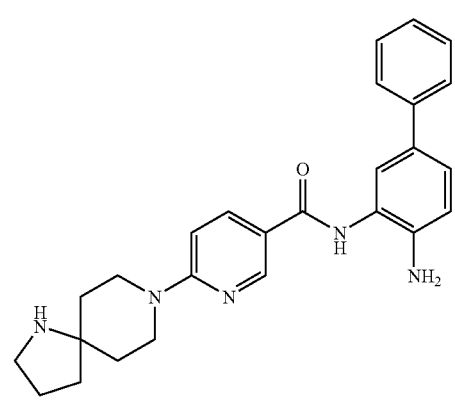 | neutral | N-(4-aminobiphenyl-3-yl)-6-(1,8-diazaspiro[4.5]dec-8-yl)nicotinamide | Cal'd [M$^+$ + 1] 428.2, Obs'd 428.2 |

EXAMPLE 8

N-(4-Amino-1-phenyl-1-1H-pyrazol-3-yl)-6-(4-oxo-1-phenyl-1,3,8-triazaspiro-[4.5]dec-8-yl)nicotinamide

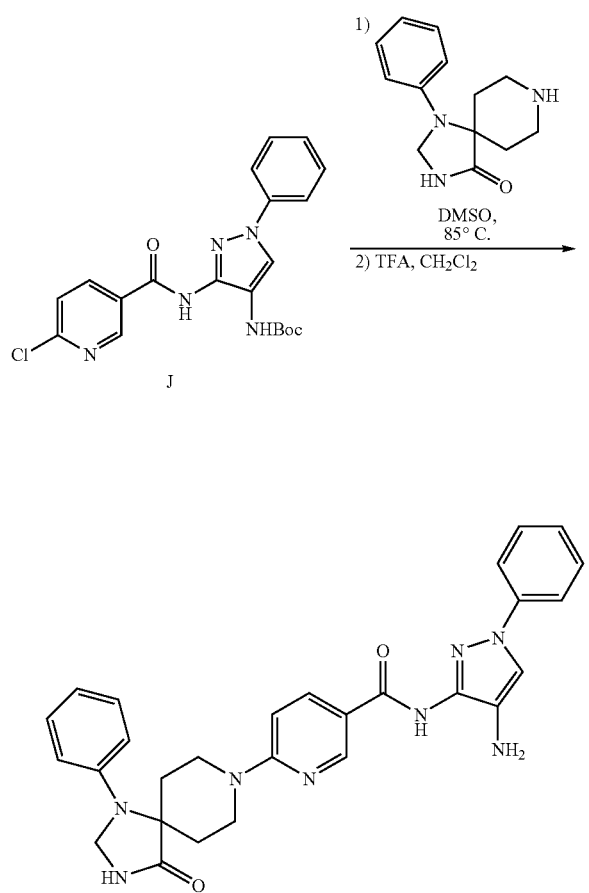

To a solution of 1-phenyl-1,3,8-triazaspiro[4.5]decan-4-one(Acros Chemical Co.) (159 mg, 0.688 mmol) in DMSO (1.2 mL) was added t-butyl(3-{[(6-chloropyridin-3-yl)carbonyl]amino}-1-phenyl-1H-pyrazol-4-yl)carbamate (114 mg, 0.275 mmol). The reaction mixture was heated at 85° C. for 12 hours, cooled to room temperature, diluted with EtOAc (25 mL) and then washed with sat.'d aq. NaHCO$_3$ (1×5 mL) and brine (1×5 mL). The organic layer was dried over Na$_2$SO$_4$, filtered, concentrated, and the crude residue purified by flash chromatography (10-100% EtOAc/hexanes). Formation of the Boc-protected pyrazolyl spiro-nicotinamide was confirmed by MS (ESI+): cal'd [N+H]$^+$609.3, exp. 609.3. To a solution of the Boc-protected N-phenyl pyrazolyl spiro-nicotinamide in CH$_2$Cl$_2$ (4 mL) was added TFA (2 mL). The reaction mixture was concentrated after 20 minutes of stirring at room temperature and the crude residue was purified by reverse-phase chromatography (10-75% MeCN/H$_2$O with 0.05% TFA). The appropriate fractions were combined, diluted with EtOAc (50 mL) and washed with sat.'d aq. NaHCO$_3$ (1×10 mL) and brine (1×5 mL). The organic layer was dried over Na$_2$SO$_4$, filtered, and concentrated to gave the desired N-phenyl pyrazolyl spiro-nicotinamide: $^1$H NMR (600 MHz, DMSO-d$_6$) δ 10.52 (s, 1H), 8.83-8.78 (m, 2H), 8.16 (dd, J=8.9 Hz, 2.5 Hz, 1H), 7.77 (s, 1H), 7.65 (d, J=7.6 Hz, 2H), 7.41 (t, 7.9 Hz, 2H), 7.16 (t, J=7.3 Hz, 1H), 7.02 (t, J=7.9 Hz, 2H), 6.96 (d, J=9.1 Hz, 1H), 6.64 (t, J=7.3 Hz, 1H), 6.48 (d, J=8.2 Hz, 2H), 4.58 (s, 2H), 4.39-4.33 (br m, 2H), 3.67 (dt, J=12.9 Hz, 3.2 Hz, 2H), 2.48-2.41 (m, 2H), 1.66 (d, J=14.1 Hz, 2H); MS (ESI+): cal'd [M+H]$^+$ 509.2, obs'd 509.2.

The compounds described in the following table were prepared by methods analogous to those synthetic methods described above, but using the appropriate starting materials.

TABLE 8

| Compound | Forms Prepared | Chemical Name | MS Data |
|---|---|---|---|
|  | HCl | 6-(7-acetyl-2,7-diazaspiro[4.4]non-2-yl)-N-(4-amino-1-phenyl-1H-pyrazol-3-yl)nicotinamide | Cal'd [M$^+$ + 1] 446.2, Obs'd 462.2 |

TABLE 8-continued

| Compound | Forms Prepared | Chemical Name | MS Data |
|---|---|---|---|
| 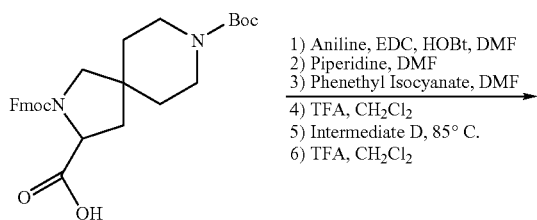 | TFA | N-[4-amino-1-(3-chlorophenyl)-1H-pyrazol-3-yl]-6-(2,8-diazaspiro[4.5]dec-8-yl)nicotinamide | Cal'd $[M^+ + 1]$ 452.2, Obs'd 452.2 |
| 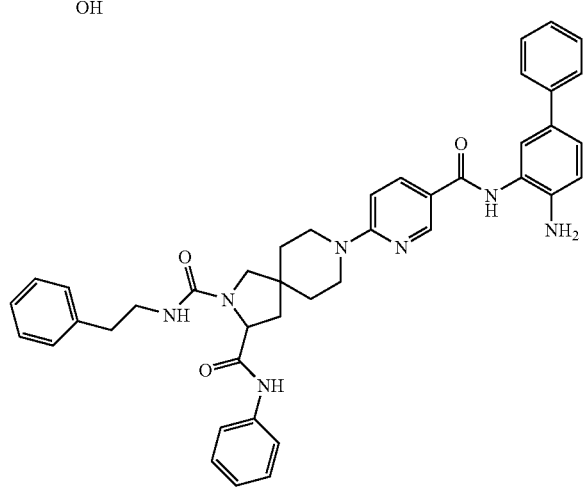 | HCl | N-(4-amino-1-phenyl-1H-pyrazol-3-yl)-6-(2,8-diazaspiro[4.5]dec-8-yl)nicotinamide | Cal'd $[M^+ + 1]$ 418.2, Obs'd 418.2 |

EXAMPLE 9

8-(5-{[(4-Aminobiphenyl-3-yl)amino]carbonyl}pyridin-2-yl)-$N^3$-phenyl-$N^2$-(2-phenylethyl)-2,8-diazaspiro[4.5]decane-2,3-dicarboxamide To a stirring solution of 8-tert-butyl 2-(9H-fluoren-9-ylmethyl) 3-(anilinocarbonyl)-2,8-diazaspiro[4.5]decane-2,8-dicarboxylate (1500 mg, 2.961 mmol), EDCI (681.2 mg, 3.553 mmol), HOBt (480.0 mg, 3.553 mmol), and DMF (4.0 mL) was added aniline (413.6 mg, 4.441 mmol). After stirring at rt for 21 h, the reaction was diluted with EtOAc (30 mL), washed with H$_2$O (1×10 mL), and brine (1×10 mL). The organic layer was then dried over Na$_2$SO$_4$, filtered, concentrated, and the crude residue was purified by column chromatography (7-60% Hexanes:EtOAc). Formation of the amide was confirmed by MS (ESI+): cal'd [M+H]$^+$ 582.3, exp. 582.3.

To a solution of amide dissolved in DMF (4.0 mL) was added piperidine (504.2 mg, 5.922 mmol). The reaction was placed under N$_2$ atmosphere and stirred at rt for 1 h. The crude reaction mixture was then concentrated, taken up in EtOAc, and washed with H$_2$O (1×10 mL). The organic layer was then dried over Na$_2$SO$_4$, filtered, concentrated, and purified by reverse phase chromatography (15-85% MeCN/H$_2$O with 0.05% TFA). The formation of the free amine was confirmed by MS (ESI+): cal'd [M+H]$^+$ 360.2, exp. 360.2. To a solution of free amine (100 mg, 0.2782 mmol) in DMF (1.5 mL) was added phenethyl isocyanate (122.84 mg, 0.8346 mmol). The reaction was stirred at rt for 18 h. The crude mixture was then diluted with EtOAc (10 mL), washed with aq. sat. NaHCO$_3$ (1×3 mL) and brine (3 mL). The organic layer was then dried over Na$_2$SO$_4$, filtered, concentrated, and purified by reverse phase chromatography (15-85% MeCN/H₂O with 0.05% TFA). The formation of the urea was confirmed by MS (ESI+): cal'd [M+H]⁺ 507.3, exp. 507.3.

The purified urea was dissolved in CH₂Cl₂ (2.0 mL), and was treated with TFA (1.0 mL) under N₂ atmosphere. After the reaction mixture was stirred at rt for 30 min, it was concentrated and purified by reverse phase chromatography (15-85% MeCN/H₂O with 0.05% TFA). The formation of the free amine was confirmed by MS (ESI+): cal'd [M+H]⁺ 407.2, exp. 407.3.

To a solution of the free amine in DMSO (0.5 mL) and toluene (0.25 mL) was added the tert-butyl (3-{[(6-chloropyridin-3-yl)carbonyl]amino}biphenyl-4-yl)carbamate (47.2 mg, 0.111 mmol). The reaction was heated in an oil bath to 85° C. After being stirred at 85° C. for 48 h the crude reaction mixture was cooled to rt, diluted with EtOAc (20 mL) and washed with aq. sat. NaHCO₃ (1×5 mL) and brine (1×3 mL). The organic layer was then dried over Na₂SO₄, filtered, concentrated, and purified by reverse phase chromatography (15-85% MeCN/H₂O with 0.05% TFA). The formation of the spiro-nicotinamide was confirmed by MS (ESI+): cal'd [M+H]⁺ 794.4, exp. 794.3.

A solution of spiro-nicotinamide in CH₂Cl₂ (2.0 mL) was then treated with TFA (1.0 mL) under N₂ atmosphere and was stirred at rt for 30 min. The crude reaction mixture was then concentrated and purified by reverse phase chromatography (10-100% MeCN/H₂O with 0.05% TFA). The appropriate fractions were collected and concentrated. The TFA salt of the desired product was then dissolved in EtOAc (30 mL), and washed with aq. sat. NaHCO₃ (1×5 mL) and brine (1×5 mL). The organic layer was then dried over Na₂SO₄, filtered and concentrated to give the desired biphenyl spiro-nicotinamide. MS (ESI+): cal'd [M+H]⁺ 694.3, exp. 694.3.

EXAMPLE 10

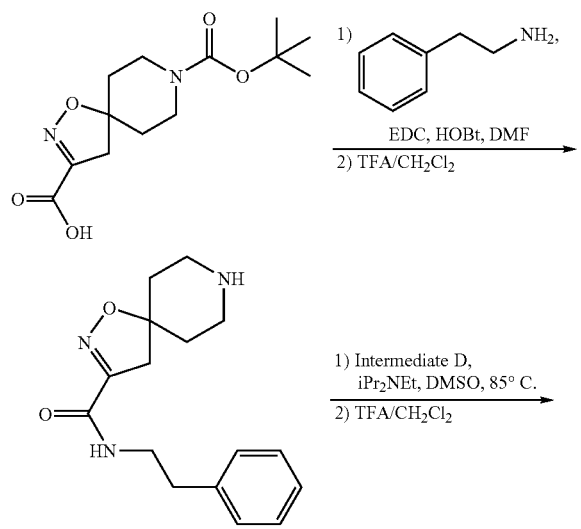

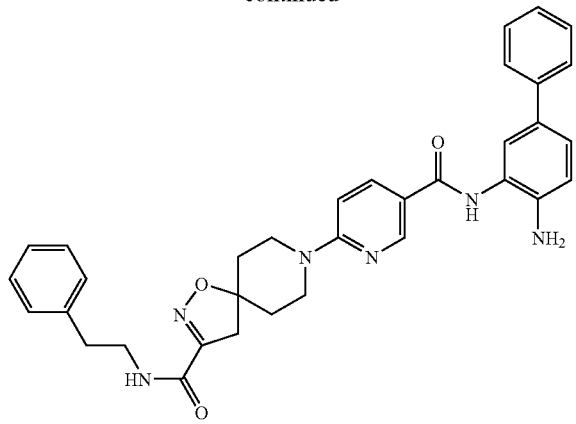

8-(5-{[(4-Aminobiphenyl-3-yl)amino]carbonyl}pyridin-2-yl)-N-(2-phenylethyl)-1-oxa-2,8-diazaspiro[4.5]dec-2-ene-3-carboxamide To a solution of 8-(tert-butoxycarbonyl)-1-oxa-2,8-diazaspiro[4.5]dec-2-ene-3-carboxylic acid (300 mg, 1.06 mmol), EDC (242 mg, 1.26 mmol), HOBt (171 mg, 1.26 mmol) in DMF (4 mL) was added phenethylamine (159 μL, 1.26 mmol). After 4 h at room temperature, the reaction mixture was diluted with EtOAc (10 mL) and washed with H₂O (1×5 mL) and brine (1×5 mL). The organic layer was dried over Na₂SO₄, filtered, and concentrated. The crude oil was taken up in CH₂Cl₂ (4 mL) and treated with TFA (2 mL). The reaction mixture was concentrated and the crude oil purified by reverse-phase chromatography (10-75% MeCN/H₂O with 0.05% TFA) to give the N-(2-phenylethyl)-1-oxa-2,8-diazaspiro[4.5]dec-2-ene-3-carboxamide confirmed by MS (ESI+): cal'd [M+H]⁺ 288.2, obs'd 288.2.

To a solution of N-(2-phenylethyl)-1-oxa-2,8-diazaspiro[4.5]dec-2-ene-3-carboxamide (127 mg, 0.442 mmol) in DMSO (1 mL) and i-Pr₂NEt (250 μL) was added tert-butyl (3-{[(6-chloropyridin-3-yl)carbonyl]amino}biphenyl-4-yl)carbamate (75 mg, 0.18 mmol). The reaction mixture was heated at 85° C. for 8 h, cooled to room temperature, diluted with EtOAc (10 mL), and then washed with NaHCO₃ (1×10 mL) and brine (1×5 mL). The organic layer was dried over Na₂SO₄, filtered, and concentrated. The crude oil was purified by flash chromatography (10-100% EtOAc/hexanes) and the biphenyl Boc-protected nicotinamide treated with TFA (2 mL) in CH₂Cl₂ (4 mL) for 20 minutes. The reaction mixture was concentrated, and the crude residue purified by reverse-phase chromatography (10-100% MeCN/H₂O with 0.05% TFA) to give the desired biphenyl benzamide after the standard NaHCO₃ (sat.'d aq.) wash of the TFA salt confirmed by MS (ESI+): cal'd [M+H]⁺ 575.3, obs'd 575.3.

EXAMPLE 11

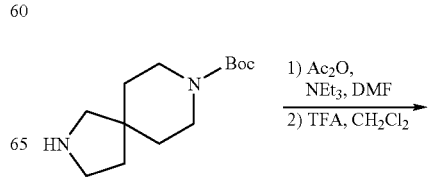

6-(2-acetyl-2,8-diazaspiro[4.5]dec-8-yl)-N-(2-amino-5-(2-thienyl)phenyl]-nicotinamide A mixture of tert-butyl 2,8-diazaspiro[4.5]decane-8-carboxylate (500 mg, 1.81 mmol) and NEt$_3$ (1.00 mL, 7.19 mmol) in 5 mL of CH$_2$Cl$_2$ was treated with Ac$_2$O and stirred for 5 h. The reaction mixture was diluted with EtOAc and washed with sat'd NaHCO$_3$, dried (Na$_2$SO$_4$), filtered and concentrated. The oily residue was dissolved in 1 mL of TFA and 3 mL of CH$_2$Cl$_2$, stirred for 1 h and concentrated. Excess TFA was azeotropically removed with methanol. The oily was dissolved in 2 mL DMSO, treated with NEt$_3$ (0.500 mL, 3.59 mmol) and chloronicotinamide F (200 mg, 0.466 mmol), stirred at 90 C for 18 h and partitioned between EtOAc and sat'd NaHCO$_3$. The organic layer was dried (Na$_2$SO$_4$), concentrated and the residue purified by chromatography on SiO$_2$ (MeOH/EtOAc, 0% to 50%). The intermediate was next stirred in 1 mL of TFA and 3 mL of CH$_2$Cl$_2$ for 2 h, concentrated, poured into CH$_2$Cl$_2$/methanol and washed with 2 N NaOH, dried (Na$_2$SO$_4$) and concentrated providing the title compound: $^1$H NMR (600 MHz, DMSO-d$_6$) δ 9.47 (s, 1H), 8.72 (s, 1H), 8.05 (m, 1H), 7.43 (s, 1H), 7.33 (d, J=4.7 Hz, 1H) 7.26 (d, J=8.2 Hz, 1H), 7.22 (d, J=2.9Hz, 1H), 7.02 (t, J=4.1 Hz, 1 H), 6.90 (dd, J=8.8, 4.7 Hz, 1H), 6.78 (d, J=8.2 Hz, 1H), 5.11 (s, 2H), 3.72 (m, 2H), 3.62 (m, 1H), 3.57 (m, 1H), 3.48 (t, J=7.0 Hz, 1H), 3.33 (m, 2H), 3.20 (s, 1H), 1.91 (s, 3H), 1.82 (t, J=7.0 Hz, 1 H), 1.73 (t, J=7.0 Hz, 1H), 1.50 (m, 4H); MS (EI) [M+H]$^+$ cal'd 476.1, obs'd 476.1.

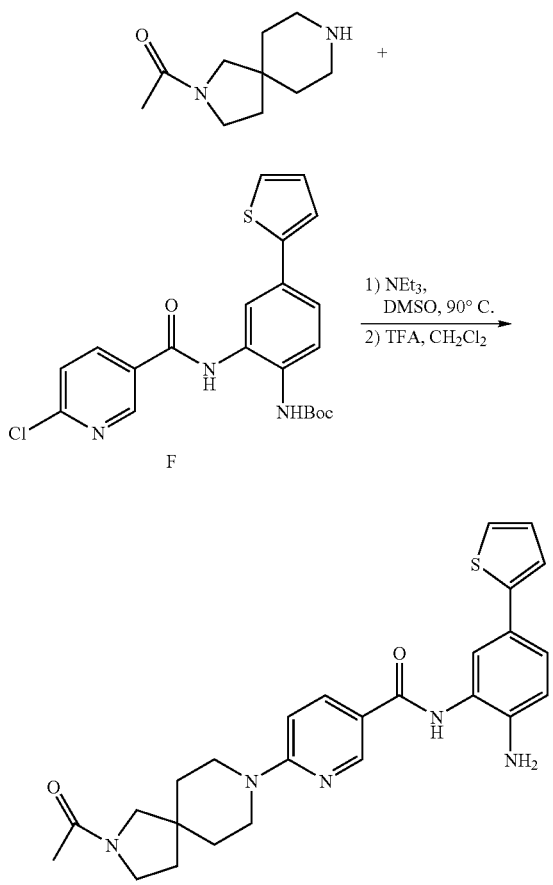

The compounds described in the following table were prepared by methods analogous to those synthetic methods described above, but using the appropriate starting materials.

TABLE 9

| Compound | Forms Prepared | Chemical Name | MS Data |
|---|---|---|---|
|  | neutral | N-(4-amino biphenyl-3-yl)-6-(2-benzyl-2,8-diazaspiro[4.5]dec-8-yl)nicotinamide | Cal'd [M$^+$ + 1] 518.3, Obs'd 518.3 |

TABLE 9-continued

| Compound | Forms Prepared | Chemical Name | MS Data |
|---|---|---|---|
| | neutral | N-(4-amino biphenyl-3-yl)-6-{2-[(2,4-dimethyl-1,3-thiazol-5-yl)sulfonyl]-2,8-diazaspiro[4.5]dec-8-yl}nicotinamide | Cal'd [M$^+$ + 1] 603.2, Obs'd 603.2 |
| | neutral, TFA, HCl | 8-[5-({[2-amino-5-(2-thienyl)phenyl]amino}carbonyl)pyridin-2-yl]-N-(2-phenylethyl)-2,8-diazaspiro[4.5]decane-2-carboxamide | Cal'd [M$^+$ + 1] 581.3, Obs'd 581.3 |
| | neutral, TFA | 8-[5-({[2-amino-5-(2-thienyl)phenyl]amino}carbonyl)pyridin-2-yl]-N-ethyl-2,8-diazaspiro[4.5]decane-2-carboxamide | Cal'd [M$^+$ + 1] 505.2, Obs'd 505.2 |
| | TFA | 8-(5-{[(4-amino biphenyl-3-yl)amino]carbonyl}pyridin-2-yl)-N-ethyl-2,8-diazaspiro[4.5]decane-2-carboxamide | Cal'd [M$^+$ + 1] 499.3, Obs'd 499.3 |

TABLE 9-continued

| Compound | Forms Prepared | Chemical Name | MS Data |
|---|---|---|---|
| | neutral, HCl | 6-(2-acetyl-2,8-diazaspiro[4.5]dec-8-yl)-N-(4-amino biphenyl-3-yl) nicotinamide | Cal'd [M+ + 1] 470.3, Obs'd 470.3 |
| | neutral, HCl | 6-(2-acetyl-2,8-diazaspiro[4.5]dec-8-yl)-N-[2-amino-5-(2-thienyl)phenyl] nicotinamide | Cal'd [M+ + 1] 476.2, Obs'd 476.1 |
| | neutral, HCl | 6-(2-acetyl-2,8-diazaspiro[4.5]dec-8-yl)-N-[2-amino-5-(3-thienyl)phenyl] nicotinamide | Cal'd [M+ + 1] 476.2, Obs'd 476.2 |
| | neutral | 8-[5-({[2-amino-5-(3-thienyl)phenyl] amino}carbonyl)pyridin-2-yl]-N-ethyl-2,8-diazaspiro[4.5]decane-2-carboxamide | Cal'd [M+ + 1] 505.2, Obs'd 505.2 |

EXAMPLE 12

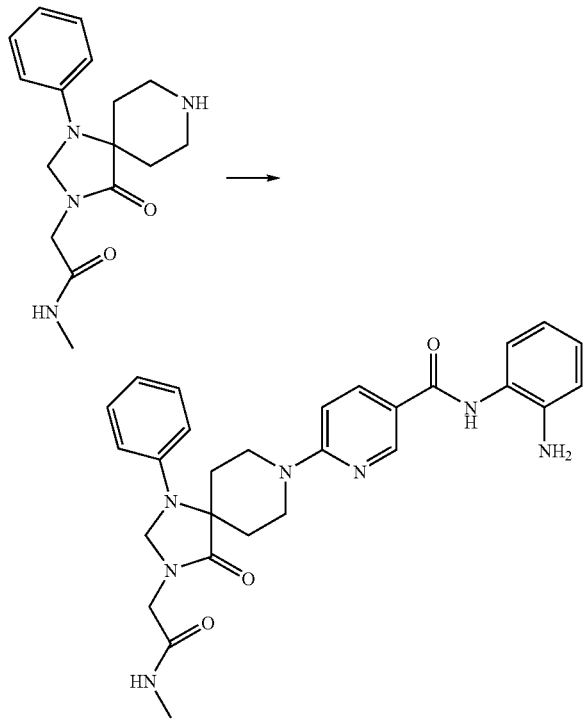

N-(2-aminophenyl)-6-{3-[2-(methylamino)-2-oxoethyl]-4-oxo-1-phenyl-1,3,8-triazaspiro[4.5]dec-8-yl}nicotinamide The title compound was prepared from N-methyl-2-(4-oxo-1-phenyl-1,3,8-triazaspiro[4.5]dec-3-yl)acetamide following the procedure outlined for example 1. MS (ESI+): cal'd [M+H]+ 514.3, Obs'd 514.3.

This spirocycle and related spirocycles were prepared via the methods described in (1) Poulain, R.; Horvath, D.; Bonnet, B.; Eckhoff, C.; Chapelain, B.; Bodinier, M.-C.; Deprez, B. From Hit to Lead. Combining Two Complementary Methods for Focused Library Design. Application to Opiate Ligands. *J. Med. Chem.* 2001, 44, 3378 and (2) Mach, R. H.; Jackson, J. R.; Luedtke, R. R.; Ivins, K. J.; Molinoff, P. B.; Ehrenkaufer, R. L. Effect of N-alkylation on the affinities of analogs of spiperone for dopamine D2 and serotonin 5-HT2 receptors. *J. Med. Chem.* 1992, 35, 423.

The compounds described in the following table were prepared by methods analogous to those synthetic methods described above, but using the appropriate starting materials.

TABLE 10

| Compound | Forms Prepared | Chemical Name | MS Data |
|---|---|---|---|
| | neutral | N-(2-aminophenyl)-6-{3-[3,5-bis(trifluoromethyl)benzyl]-4-oxo-1-phenyl-1,3,8-triazaspiro[4.5]dec-8-yl}nicotinamide | Cal'd [M+ + 1] 669.2, Obs'd 669.2 |
| | neutral | N-(2-aminophenyl)-6-[3-(2-anilino-2-oxoethyl)-4-oxo-1-phenyl-1,3,8-triazaspiro[4.5]dec-8-yl]nicotinamide | Cal'd [M+ + 1] 576.3, Obs'd 576.3 |

TABLE 10-continued

| Compound | Forms Prepared | Chemical Name | MS Data |
|---|---|---|---|
| | neutral | N-(2-aminophenyl)-6-[3-(1H-benzimidazol-2-ylmethyl)-4-oxo-1-phenyl-1,3,8-triazaspiro[4.5]dec-8-yl]nicotinamide | Cal'd [M$^+$ + 1] 572.3, Obs'd 572.3 |
| | neutral | N-(2-aminophenyl)-6-(3-methyl-4-oxo-1-phenyl-1,3,8-triazaspiro[4.5]dec-8-yl)nicotinamide | Cal'd [M$^+$ + 1] 457.2, Obs'd 457.2 |

EXAMPLE 13

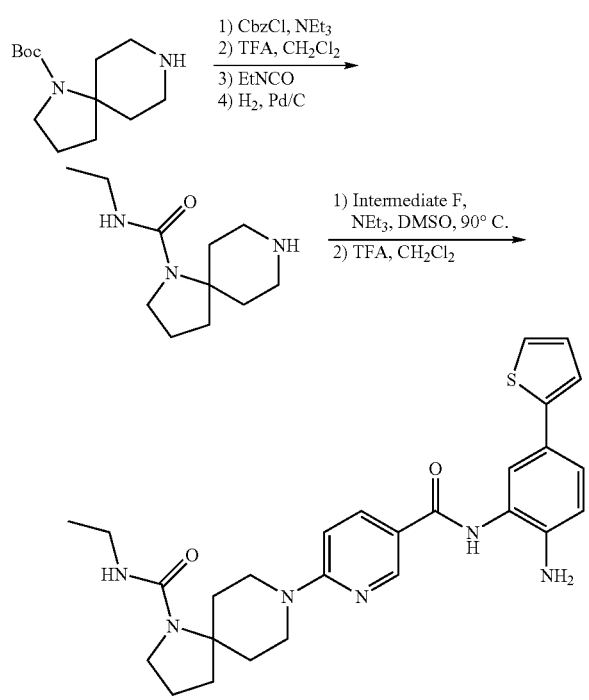

8-[5-({[2-Amino-5-(2-thienyl)phenyl]amino}carbonyl)pyridin-2-yl]-N-ethyl-1,8-diazaspiro[4.5]decane-1-carboxamide A solution of tert-butyl 1,8-diazaspiro[4.5]-decane-1-carboxylate (600 mg, 2.5 mmol) in 5 mL of CH$_2$Cl$_2$ was treated with CbzCl (528 μL, 3.75 mmol) and NEt$_3$ (697 μL, 5.0 mmol) and stirred for 1 h at room temperature. The reaction mixture was partitioned between EtOAc and saturated NaHCO$_3$, the organic layer was dried (MgSO$_4$), filtered and concentrated. The crude residue was purified by SiO$_2$ gel chromatography (0-100% EtOAc/CH$_2$Cl$_2$). The residue was stirred in 2 mL of TFA and 2 mL of CH$_2$Cl$_2$ for 1 h at room temperature and concentrated. The reaction mixture was neutralized with EtOAc/sat'd NaHCO$_3$ extraction, dried (MgSO$_4$), filtered and concentrated. Formation of the Cbz-protected spirocycle was confirmed by MS (ESI+): cal'd [M+H]$^+$ 275.2, exp. 275.2.

To a solution of the Cbz-protected spirocycle in CH$_2$Cl$_2$ (5 mL) was added Et$_3$N (509 μL, 3.65 mmol) and ethyl isocyanate (115 μL, 1.46 mmol) and stirred at room temperature for 12 h. The reaction mixture was partitioned between EtOAc and saturated NaHCO$_3$, the organic layer was dried (MgSO$_4$), filtered and concentrated. A suspension of the spiroamine (200 mg, 0.73 mmol) and 5 mol % Pd/C (40 mg, 0.037 mmol) in 5 mL of MeOH was deoxygenated by hydrogen/vacuum exchange. The mixture was treated with 1 atm of hydrogen for 3 days, filtered through Celite and concentrated giving N-ethyl-1,8-diazaspiro[4.5]decane-1-carboxamide.

A solution of intermediate F (82 mg, 0.19 mmol), N-ethyl-1,8-diazaspiro[4.5]-decane-1-carboxamide (73 mg, 0.35 mmol), and NEt$_3$ (43 μL, 0.31 mmol) in 5 mL of DMSO was stirred at 90° C. for 12 h. The reaction mixture was partitioned between EtOAc and saturated NaHCO$_3$, the organic layer was dried (MgSO$_4$), filtered and concentrated. The residue was stirred in 2 mL of TFA and 2 mL of CH$_2$Cl$_2$ for 1 h at room temperature and concentrated. Reverse-phase chromatography (10 to 100% MeCN/water with 0.05% TFA) followed by neutralization with EtOAc/saturated NaHCO$_3$ extraction and drying with MgSO$_4$ gave the title compound: MS (ESI+): cal'd [M+H]$^+$ 505.2, obs'd 505.2.

The compounds described in the following table were prepared by methods analogous to those synthetic methods described above, but using the appropriate starting materials.

TABLE 11

| Compound | Forms Prepared | Chemical Name | MS Data |
|---|---|---|---|
|  | neutral | 6-(1-acetyl-1,8-diazaspiro[4.5]dec-8-yl)-N-(4-aminobiphenyl-3-yl)nicotinamide | Cal'd [M$^+$ + 1] 470.3, Obs'd 470.3 |
|  | neutral | 6-(1-acetyl-1,8-diazaspiro[4.5]dec-8-yl)-N-[2-amino-5-(2-thienyl)phenyl] nicotinamide | Cal'd [M$^+$ + 1] 476.2, Obs'd 476.2 |

EXAMPLE 14

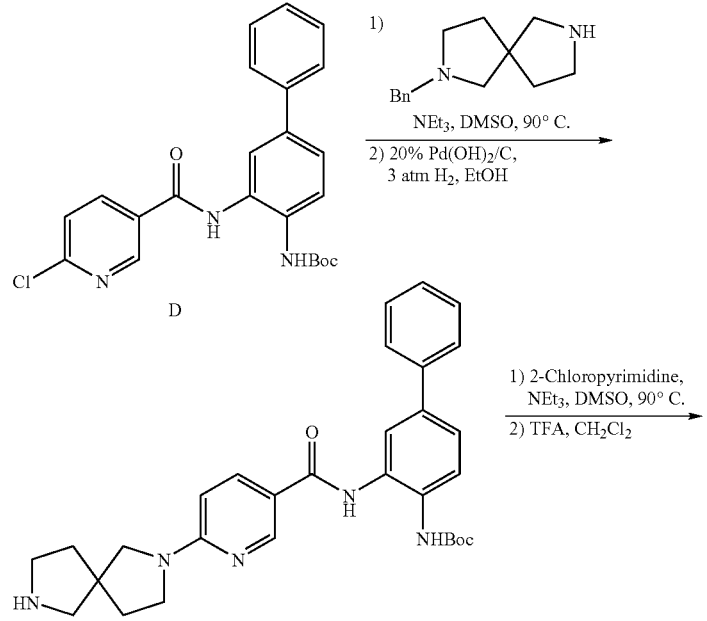

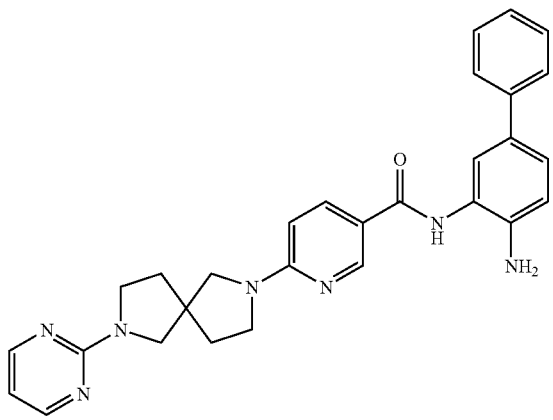

N-(4-Aminobiphenyl-3-yl)-6-(7-pyrimidin-2-yl-2,7-diazaspiro[4.4]non-2-yl)nicotinamide A solution of the 6-chloronicotinamide D (580 mg, 1.37 mmol) in 5 mL of DMSO was treated with NEt$_3$ (0.50 mL, 3.59 mmol) and 2-benzyl-2,7-diazaspiro[4.4]nonane (500 mg, 2.31 mmol) and heated to 90° C. for 15 h. The mixture was cooled and partitioned between EtOAc and saturated NaHCO$_3$, dried (Na$_2$SO$_4$), filtered and concentrated. Chromatography on SiO$_2$ (0 to 30% MeOH/EtOAc) gave the adduct. A suspension of this benzyl amine (700 mg, 1.16 mmol) and 20% Pd(OH)$_2$/C (200 mg, 0.28 mmol) in 10 mL of EtOH was deoxygenated by hydrogen/vacuum exchange. The mixture was treated with 55 psi of hydrogen for 2 days (Parr hydrogenation apparatus), filtered through Celite and concentrated giving the debenzylated spirocyclic amine. A portion of this secondary amine (40 mg, 0.078 mmol) in 2 mL of DMSO was treated with NEt$_3$ (0.050 mL) and 2-chloropyrimidine (20 mg, 0.18 mmol), then heated to 90° C. for 15 h. The crude mixture was partitioned between EtOAc and saturated NaHCO$_3$, dried (Na$_2$SO$_4$) and concentrated. The resulting residue was dissolved in 1:1 TFA/CH$_2$Cl$_2$ (2 mL) and stirred for 2 h then concentrated. Reverse-phase chromatography (20 to 100% MeCN/water with 0.05% TFA) followed by neutralization with EtOAc/saturated NaHCO$_3$ extraction and drying with Na$_2$SO$_4$ gave the target pyrimidine: $^1$H NMR (600 MHz, CD$_3$OD) δ 8.73 (s, 1H), 8.30 (d, J=5.0 Hz, 2 H), 8.10 (dd, J=8.80, 2.1 Hz, 1H), 7.54 (d, J=7.3 Hz, 2H), 7.45 (d, J=2.1 Hz, 1H), 7.35 (m, 3H), 7.23 (t, J=1.2 Hz, 1H), 6.95 (d, J=8.5Hz, 1H), 6.59 (t, J=5.0Hz, 1H), 6.57 (d, J=9.1 Hz, 1H), 3.60-3.70 (m, 4H), 3.50-3.60 (m, 4H), 2.08-2.15 (m, 4H); MS (EI) [M+H]$^+$ cal'd 492.3, obs'd 492.3.

The compounds described in the following table were prepared by methods analogous to those synthetic methods described above, but using the appropriate starting materials.

TABLE 12

| Compound | Forms Prepared | Chemical Name | MS Data |
|---|---|---|---|
|  | neutral | N-(4-aminobiphenyl-3-yl)-6-[7-(phenylsulfonyl)-2,7-diazaspiro[4.4]non-2-yl]nicotinamide | Cal'd [M$^+$ + 1] 554.2, Obs'd 554.2 |

TABLE 12-continued

| Compound | Forms Prepared | Chemical Name | MS Data |
|---|---|---|---|
| | neutral | N-(4-aminobiphenyl-3-yl)-6-(7-benzoyl-2,7-diazaspiro[4.4]non-2-yl) nicotinamide | Cal'd [M$^+$ + 1] 518.3, Obs'd 518.3 |
| | neutral | 7-(5-[{(4-amino biphenyl-3-yl)amino] carbonyl}pyridin-2-yl)-N-[(1S)-1-phenylethyl]-2,7-diazaspiro[4.4]nonane-2-carboxamide | Cal'd [M$^+$ + 1] 561.3, Obs'd 561.3 |
| | neutral | 7-(5-{[(4-amino biphenyl-3-yl)amino] carbonyl}pyridin-2-yl)-N-[(1R)-1-phenylethyl]-2,7-diazaspiro[4.4]nonane-2-carboxamide | Cal'd [M$^+$ + 1] 561.3, Obs'd 561.3 |
| | neutral | 7-(5-{[(4-amino biphenyl-3-yl)amino] carbonyl}pyridin-2-yl)-N-ethyl-2,7-diazaspiro[4.4]nonane-2-carboxamide | Cal'd [M$^+$ + 1] 485.3, Obs'd 485.3 |

TABLE 12-continued

| Compound | Forms Prepared | Chemical Name | MS Data |
|---|---|---|---|
| | neutral | 7-(5-{[(4-amino biphenyl-3-yl)amino]carbonyl}pyridin-2-yl)-N-(2-phenylethyl)-2,7-diazaspiro[4.4]nonane-2-carboxamide | Cal'd [M+ + 1] 561.3, Obs'd 561.3 |
| | neutral | ethyl 7-(5-{[(4-aminobiphenyl-3-yl)amino]carbonyl}-pyridin-2-yl)-2,7-diazaspiro[4.4]nonane-2-carboxylate | Cal'd [M+ + 1] 486.2, Obs'd 485.3 |
| | neutral | N-(4-aminobiphenyl-3-yl)-6-(2,7-diazaspiro[4.5]dec-7-yl)nicotinamide | Cal'd [M+ + 1] 428.2, Obs'd 428.3 |
| | neutral | benzyl 7-(5-{[(4-aminobiphenyl-3-yl)amino]carbonyl}pyridin-2-yl)-2,7-diazaspiro[4.4]nonane-2-carboxylate | Cal'd [M+ + 1] 548.3, Obs'd 548.3 |

EXAMPLE 15

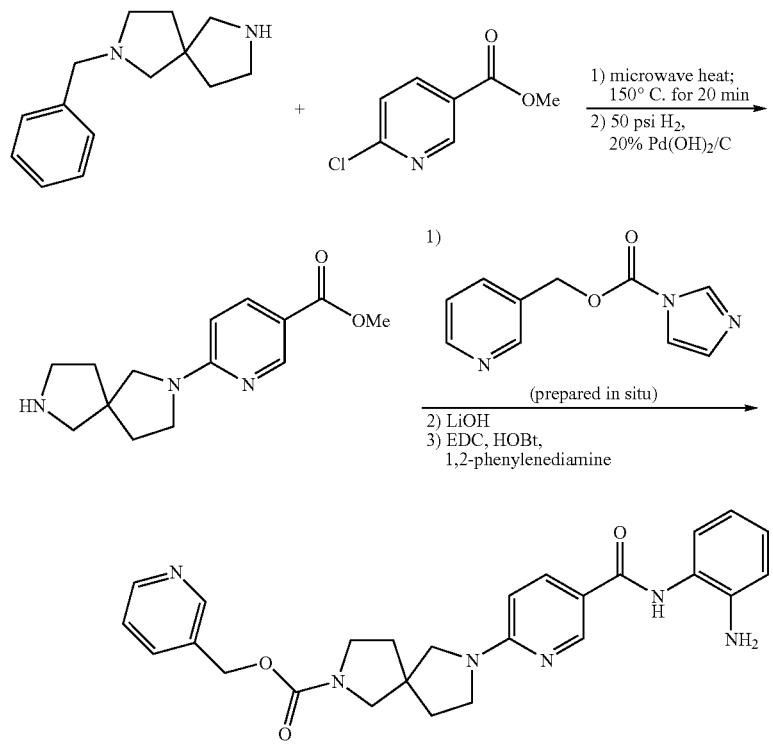

Pyridin-3-ylmethyl 7-(5-{[(2-Aminophenyl)amino]carbonyl}pyridin-2-yl)-2,7-diazaspiro[4.4]nonane-2-carboxylate 2-Benzyl-2,7-diazaspiro[4.4]nonane was purchased from Clariant Ltd. For synthesis and manipulation of this spirocycle, see Culbertson, T. P. et al., Quinolone antibacterial agents substituted at the 7-position with spiroamines. Synthesis and structure-activity relationships. *J. Med. Chem.* 1990, 33, 2270.

A mixture of 2-benzyl-2,7-diazaspiro[4.4]nonane (1.00 g, 4.68 mmol), methyl 6-chloronicotinate (800 mg, 4.68 mmol) and $K_2CO_3$ (700 mg, 5.07 mmol) in 5 mL of DMSO was stirred under microwave irradiation for 20 min at a temperature of 150° C. The mixture was poured into EtOAc and washed with sat'd $NaHCO_3$, dried ($Na_2SO_4$), filtered and concentrated, giving methyl 6-(7-benzyl-2,7-diazaspiro[4.4]non-2-yl)nicotinate. A bottle containing a suspension of the benzyl amine and 20% $Pd(OH)_2$/C (600 mg, 0.857 mmol) in 20 mL of EtOH was evacuated and purged with $H_2$ gas three times. Using a Parr shaker apparatus, the suspension was agitated under 50 psi of $H_2$ for 20 h. The pressure was released and the mixture filtered through a pad of Celite and concentrated, giving methyl 6-(2,7-diazaspiro[4.4]non-2-yl)nicotinate: $^1$H NMR (600 MHz, DMSO-$d_6$) δ 8.59 (d, J=2.1 Hz, 1H), 7.89 (dd, J=9.1, 2.3 Hz, 1H), 7.27 (d, J=4.4 Hz, 1H), 6.44 (d, J=8.8 Hz, 1H), 3.74 (s, 3H), 3.13 (br s, 4H), 2.89 (t, J=7.3 Hz, 2H), 2.72 (AB, J=7.6 Hz, 2H), 1.92 (br m, 2H), 1.69 (AB, J=7.3 Hz, 2H).

A mixture of pyridin-3-ylmethanol (0.050 mL, 0.51 mmol) and carbonyl diimidazole (80 mg, 0.49 mmol) in 3 mL of THF was stirred for 4 h. Next, methyl 6-(2,7-diazaspiro[4.4]non-2-yl)nicotinate (150 mg, 0.575 mmol) and DMAP (1 crystal) were added and the mixture stirred for 15 h, then concentrated to dryness. Chromatography on $SiO_2$ (0-20% MeOH/EtOAc) gave the intermediate methyl ester. The methyl ester was dissolved in 2 mL of 1:1 THF/water, treated with LiOH.$H_2O$ (25 mg, 0.60 mmol) and stirred for 20 hours, after which the mixture was concentrated, azeotropically dried with MeOH and placed under vacuum for 3 h. A mixture of the residue in 2 mL of DMF was treated with EDC (200 mg, 1.05 mmol), HOBt (100 mg, 0.74 mmol) and phenylenediamine (100 mg, 0.93 mmol), stirred for 15 h and concentrated to dryness. Reverse-phase chromatography (5-20% water/MeCN with 0.05% TFA) gave pyridin-3-ylmethyl 7-(5-{[(2-aminophenyl)amino]carbonyl}pyridin-2-yl)-2,7-diazaspiro[4.4]nonane-2-carboxylate as the tris-TFA salt: $^1$H NMR (600 MHz, DMSO-$d_6$) δ 9.95 (d, J=4.1 Hz, 1H), 8.73 (d, J=12.9 Hz, 1H), 8.65-8.67 (m, 2H), 8.17 (d, J=9.1 Hz, 1H), 8.10 (dd, J=21.0, 7.9 Hz, 1H), 7.66 (m, 1H), 7.25 (d, J=7.9 Hz, 1H), 7.13 (t, J=7.6 Hz, 1H), 7.05 (d, J=7.9 Hz, 1H), 6.96 (m, 1H), 6.74 (dd, J=9.1, 3.8 Hz, 1H), 5.15 (m, 2H), 3.60 (br m, 2H), 3.30-3.55 (m, 6H), 2.01 (m, 2H), 1.91 (m, 2H); MS (EI) [M+H]$^+$ cal'd 473.3, obs'd 473.4.

The compounds described in the following table were prepared by methods analogous to those synthetic methods described above, but using the appropriate starting materials.

TABLE 13

| Compound | Forms Prepared | Chemical Name | MS Data |
|---|---|---|---|
| | TFA | benzyl 7-(5-{[(2-aminophenyl)amino]-carbonyl}pyridin-2-yl)-2,7-diazaspiro[4.4]nonane-2-carboxylate | Cal'd [M+ + 1] 472.2, Obs'd 472.2 |
| | TFA | N-(2-aminophenyl)-6-(7-benzoyl-2,7-diazaspiro[4.4]non-2-yl)nicotinamide | Cal'd [M+ + 1] 442.2, Obs'd 442.3 |
| | TFA | N-(2-aminophenyl)-6-(7-(2-phenylethanoyl)-2,7-diazaspiro[4.4]non-2-yl)nicotinamide | Cal'd [M+ + 1] 456.2, Obs'd 456.2 |
| | TFA | N-(2-aminophenyl)-6-[7-(3-phenyl propanoyl)-2,7-diazaspiro[4.4]non-2-yl]nicotinamide | Cal'd [M+ + 1] 470.3, Obs'd 470.3 |
| | Neutral | N-(2-aminophenyl)-6-[7-(phenylsulfonyl)-2,7-diazaspiro[4.4]non-2-yl]nicotinamide | Cal'd [M+ + 1] 478.2, Obs'd 478.2 |

TABLE 13-continued

| Compound | Forms Prepared | Chemical Name | MS Data |
|---|---|---|---|
| | Neutral | N-(2-aminophenyl)-6-[7-(4-methoxybenzyl)-2,7-diazaspiro[4.4]non-2-yl]nicotinamide | Cal'd [M⁺ + 1] 458.3, Obs'd 458.3 |
| | Neutral | tert-butyl 7-(5-{[(2-aminophenyl)amino]-carbonyl}pyridin-2-yl)-2,7-diazaspiro[4.4]nonane-2-carboxylate | Cal'd [M⁺ + 1] 438.2, Obs'd 438.3 |
| | TFA | pyridin-3-ylmethyl 7-(5-{[(2-aminophenyl)amino]carbonyl}pyridin-2-yl)-2,7-diazaspiro[4.4]nonane-2-carboxylate | Cal'd [M⁺ + 1] 473.2, Obs'd 473.4 |
| | Neutral | tert-butyl 8-(5-{[(2-aminophenyl)amino]-carbonyl}pyridin-2-yl)-2,8-diazaspiro[4.5]decane-2-carboxylate | Cal'd [M⁺ + 1] 452.3, Obs'd 452.3 |
| | Neutral | tert-butyl 8-(5-{[(2-aminophenyl)amino]-carbonyl}pyridin-2-yl)-1,8-diazaspiro[4.5]decane-1-carboxylate | Cal'd [M⁺ + 1] 452.3, Obs'd 452.3 |
| | Neutral | benzyl 8-(5-{[(2-aminophenyl)amino]-carbonyl}pyridin-2-yl)-1,8-diazaspiro[4.5]decane-1-carboxylate | Cal'd [M⁺ + 1] 486.2, Obs'd 486.2 |

TABLE 13-continued

| Compound | Forms Prepared | Chemical Name | MS Data |
|---|---|---|---|
| 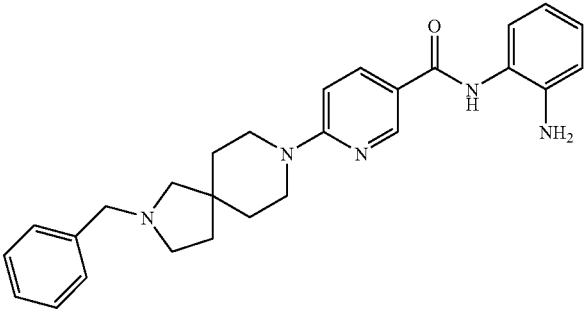 | TFA | N-(2-aminophenyl)-6-(2-benzyl-2,8-diazaspiro[4.5]dec-8-yl)nicotinamide | Cal'd [M$^+$ + 1] 442.3, Obs'd 442.2 |
| 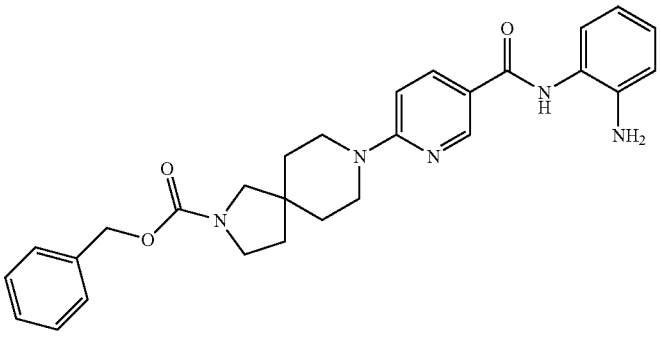 | Neutral | benzyl 8-(5-{[(2-aminophenyl)amino]-carbonyl}pyridin-2-yl)-2,8-diazaspiro[4.5]decane-2-carboxylate | Cal'd [M$^+$ + 1] 486.2, Obs'd 486.2 |
| 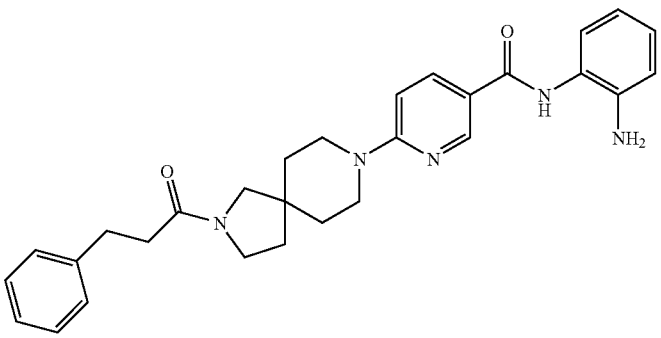 | Neutral | N-(2-aminophenyl)-6-[2-(3-phenylpropanoyl)-2,8-diazaspiro[4.5]dec-8-yl]nicotinamide | Cal'd [M$^+$ + 1] 484.3, Obs'd 484.2 |
| 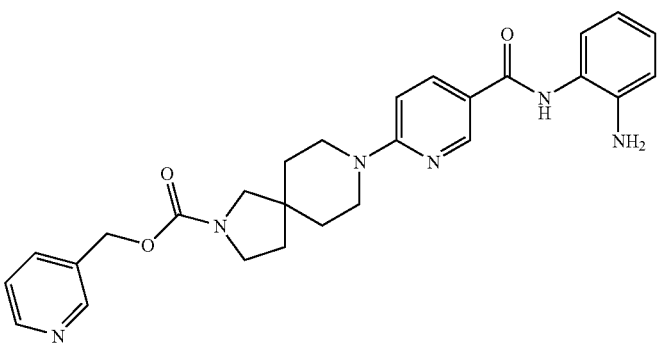 | Neutral | pyridin-3-ylmethyl 8-(5-{[(2-aminophenyl)amino]carbonyl}pyridin-2-yl)-2,8-diazaspiro[4.5]decane-2-carboxylate | Cal'd [M$^+$ + 1] 487.2, Obs'd 487.2 |

TABLE 13-continued

| Compound | Forms Prepared | Chemical Name | MS Data |
|---|---|---|---|
| | TFA | 8-(5-{[(2-aminophenyl)amino]carbonyl}pyridin-2-yl)-N-[(1R)-1-phenylethyl]-2,8-diazaspiro[4.5]decane-2-carboxamide | Cal'd [M+ + 1] 499.3, Obs'd 499.3 |
| | TFA | 8-(5-{[(2-aminophenyl)amino]carbonyl}pyridin-2-yl)-N-[(1S)-1-phenylethyl]-2,8-diazaspiro[4.5]decane-2-carboxamide | Cal'd [M+ + 1] 499.3, Obs'd 499.3 |
| | TFA | 8-(5-{[(2-aminophenyl)amino]carbonyl}pyridin-2-yl)-N-(4-fluorophenyl)-2,8-diazaspiro[4.5]decane-2-carboxamide | Cal'd [M+ + 1] 489.2, Obs'd 489.2 |
| | Neutral | N-(2-aminophenyl)-6-[7-(quinolin-8-ylsulfonyl)-2,7-diazaspiro[4.4]non-2-yl]nicotinamide | Cal'd [M+ + 1] 529.2, Obs'd 529.2 |
| | Neutral | N-(2-aminophenyl)-6-{7-[(2,4-dimethyl-1,3-thiazol-5-yl)sulfonyl]-2,7-diazaspiro[4.4]non-2-yl}nicotinamide | Cal'd [M+ + 1] 513.2, Obs'd 513.2 |

TABLE 13-continued
| Compound | Forms Prepared | Chemical Name | MS Data |
|---|---|---|---|
| | Neutral | N-(2-aminophenyl)-6-[7-(benzylsulfonyl)-2,7-diazaspiro[4.4]non-2-yl]nicotinamide | Cal'd [M+ + 1] 492.2, Obs'd 492.2 |
| | Neutral | N-(2-aminophenyl)-6-[7-(1-naphthylsulfonyl)-2,7-diazaspiro[4.4]non-2-yl]nicotinamide | Cal'd [M+ + 1] 528.2, Obs'd 528.2 |
| | Neutral | N-(2-aminophenyl)-6-[7-(2-naphthylsulfonyl)-2,7-diazaspiro[4.4]non-2-yl]nicotinamide | Cal'd [M+ + 1] 528.2, Obs'd 528.2 |
EXAMPLE 16
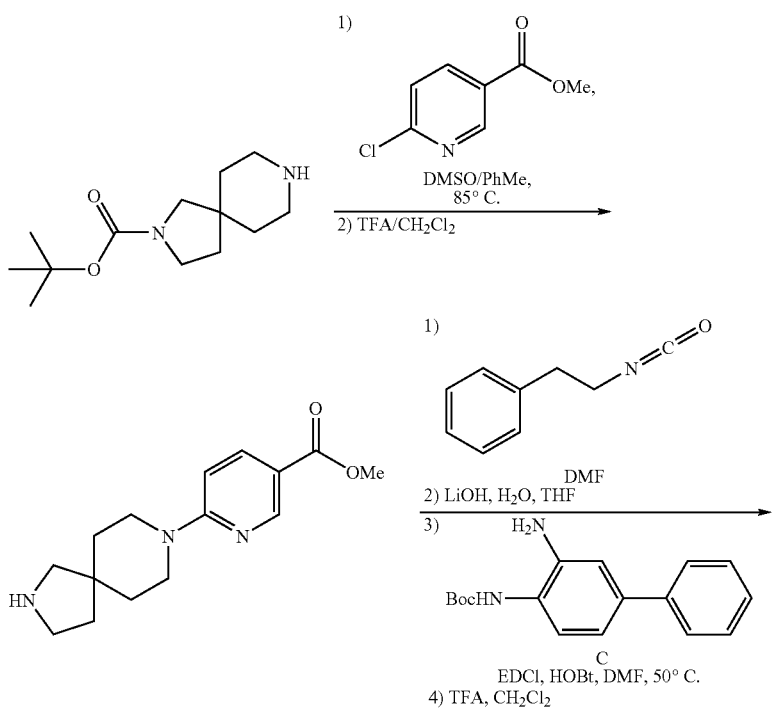

-continued

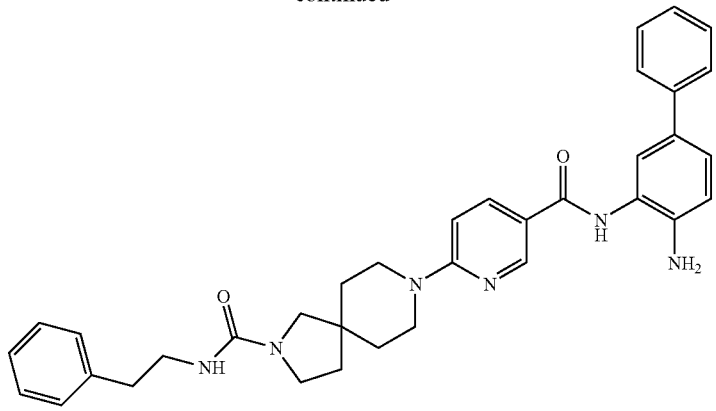

8-(5-{[(4-Aminobiphenyl-3-yl)amino]carbonyl}pyridin-2-yl)-N-(2-phenylethyl)-2,8-diazaspiro[4.5]decane-2-carboxamide To a solution of methyl 6-chloronicotinate (200 mg, 1.16 mmol) in DMSO/PhMe (2 mL of a 1:1 solution) was added t-butyl-2,8-diazaspiro[4.5]decane-2-carboxylate (700 mg, 2.91 mmol). The reaction mixture was heated at 85° C. for 6 hours and then diluted with EtOAc (10 mL). The organic layer was washed with NaHCO$_3$ (1×5 mL) and brine (1×5 mL), dried over Na$_2$SO$_4$, and then concentrated. The crude residue was purified by reverse-phase flash chromatography (10-100% MeCN/H$_2$O with 0.05% TFA) to give t-butyl 8-[5-(methoxycarbonyl)pyridin-2-yl]-2,8-diazaspiro[4.5]decane-2-carboxylate: MS (ESI+): cal'd [M+H]$^+$ 376.2, obs'd 376.2. This intermediate was then treated with TFA (3 mL) in CH$_2$Cl$_2$ (6 mL). The reaction mixture was concentrated after 30 minutes of stirring at room temperature and the crude residue was purified by reverse-phase flash chromatography (10-75% MeCN/H$_2$O with 0.05% TFA) to give the methyl 6-(2,8-diazaspiro[4.5]dec-8-yl)nicotinate: MS (ESI+): cal'd [M+H]$^+$ 276.2, obs'd 276.2.

To a solution of methyl 6-(2,8-diazaspiro[4.5]dec-8-yl)nicotinate (245.2 mg, 0.891 mmol) in DMF (3.0 mL) was added phenethyl isocyanate (393.3 mg, 2.672 mmol). After 23 h of stirring at room temperature the reaction mixture was diluted with EtOAc (15 mL) and washed with saturated aqueous NaHCO$_3$ (1×4 mL) and brine (1×4 mL). The organic layer was then dried over Na$_2$SO$_4$, filtered, concentrated, and the crude residue was purified by reverse-phase chromatography (15-85% MeCN/H$_2$O with 0.05% TFA). Formation of the methyl 6-(2-{[(2-phenylethyl)amino]carbonyl}-2,8-diazaspiro[4.5]dec-8-yl)nicotinate was confirmed by MS (ESI+): cal'd [M+H]$^+$ 423.2, obs'd 423.3.

To a solution of LiOH (63.7 mg, 2.672 mmol) in H$_2$O (750 µL) was added dropwise a solution of methyl 6-(2-{[(2-phenylethyl)amino]carbonyl}-2,8-diazaspiro[4.5]dec-8-yl)nicotinate in THF (1 mL). The reaction mixture was then heated to reflux and cooled to room temperature. After 22 h of stirring at room temperature the reaction was concentrated, taken up in MeOH (5 mL), and purified by reverse-phase chromatography (15-85% MeCN/H$_2$O with 0.05% TFA). Formation of the 6-(2-{[(2-phenylethyl)amino]carbonyl}-2,8-diazaspiro[4.5]dec-8-yl)nicotinic acid was confirmed by MS (ESI+): cal'd [M+H]$^+$ 409.2, obs'd 409.2.

To a solution of the 6-(2-{[(2-phenylethyl)amino]carbonyl}-2,8-diazaspiro[4.5]dec-8-yl)nicotinic acid in DMF (2.5 mL) was added EDCI (512.3 mg, 2.672 mmol) and HOBt (300.8 mg, 2.227 mmol). The reaction mixture was allowed to stir for 10 min. at room temperature. t-butyl (3-aminobiphenyl-4-yl)carbamate (759.8 mg, 2.672 mmol) was then added at room temperature. The reaction was heated to 50° C. and was allowed to stir for 90 h. The reaction mixture was then cooled to room temperature, diluted with EtOAc (15 mL) and washed with H$_2$O (5 mL). The organic layer was then dried over Na$_2$SO$_4$, filtered, concentrated, and purified by reverse-phase chromatography (15-100% MeCN/H$_2$O with 0.05% TFA). Formation of the Boc-protected biphenyl spiro-nicotinamide was confirmed by MS (ESI+): cal'd 675.3, obs'd 675.3.

To a solution of the Boc-protected biphenyl spiro-nicotinamide in CH$_2$Cl$_2$ (4 mL) was added TFA (1.5 mL). After stirring at room temperature for 30 min. the reaction mixture was concentrated and the crude residue was purified by reverse-phase chromatography (15-85% MeCN/H$_2$O with 0.05% TFA). The appropriate fractions were combined, diluted with EtOAc (50 mL) and washed with saturated aqueous NaHCO$_3$ (1×5 mL) and brine (1×5 mL). The organic layer was dried over Na$_2$SO$_4$, filtered, and concentrated to give the desired biphenyl spiro-nicotinamide: $^1$H NMR (600 MHz, DMSO-d$_6$) δ 9.49 (s, 1H), 8.73 (d, J=2.3 Hz, 1H), 8.06 (dd, J=11.4 Hz, 2.4 Hz, 1H), 7.52 (dd, J=9.5 Hz, 1.1 Hz, 2H), 7.47 (d, J=2.1 Hz, 1H), 7.36 (t, J=7.9, 2H), 7.29-7.24 (m, 3H), 7.21 (t, J=7.3 Hz, 1H), 7.17-7.15 (m, 3H), 6.90 (d, J=9.1 Hz, 1H), 6.83 (d, J=8.2 Hz, 1H), 3.76-3.72 (m, 2H), 3.56-3.52 (m, 2H), 3.30-3.25 (m, 3H), 3.21-3.17 (m, 2H), 3.13 (br s, 2H), 2.69 (t, J=7.5 Hz, 2H), 1.74 (t, J=7.04 Hz, 2H), 1.50-1.47 (m, 4H); MS (ESI+): cal'd [M+H]$^+$ 575.3, obs'd 575.3.

The compounds described in the following table were prepared by methods analogous to those synthetic methods described above, but using the appropriate starting materials.

TABLE 14
| Compound | Forms Prepared | Chemical Name | MS Data |
|---|---|---|---|
| 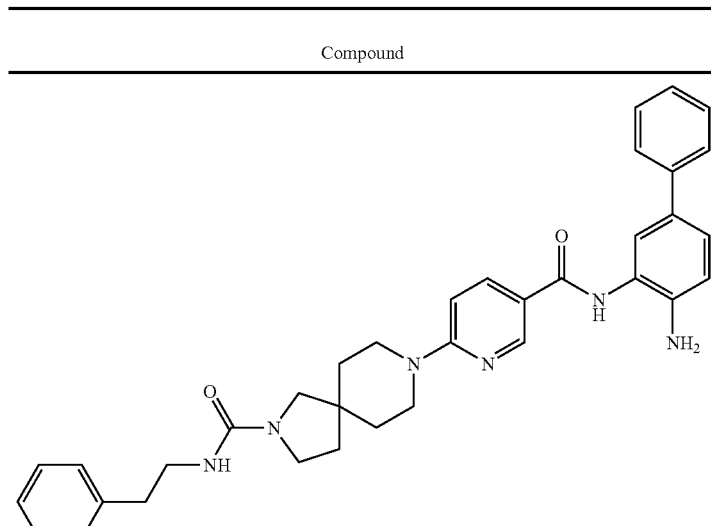 | neutral, TFA | 8-(5-{[(4-aminobiphenyl-3-yl)amino]carbonyl}pyridin-2-yl)-N-(2-phenylethyl)-2,8-diazaspiro[4.5]decane-2-carboxamide | Cal'd [M⁺ + 1] 575.3, Obs'd 575.3 |
| 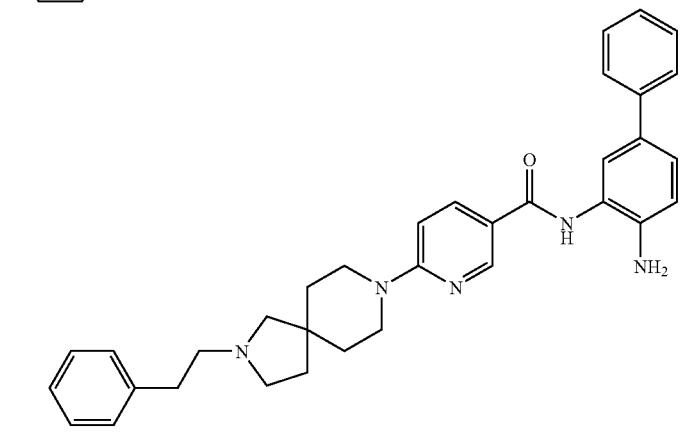 | neutral | N-(4-aminobiphenyl-3-yl)-6-[2-(2-phenylethyl)-2,8-diazaspiro[4.5]dec-8-yl]nicotinamide | Cal'd [M⁺ + 1] 532.3, Obs'd 532.3 |
EXAMPLE 17
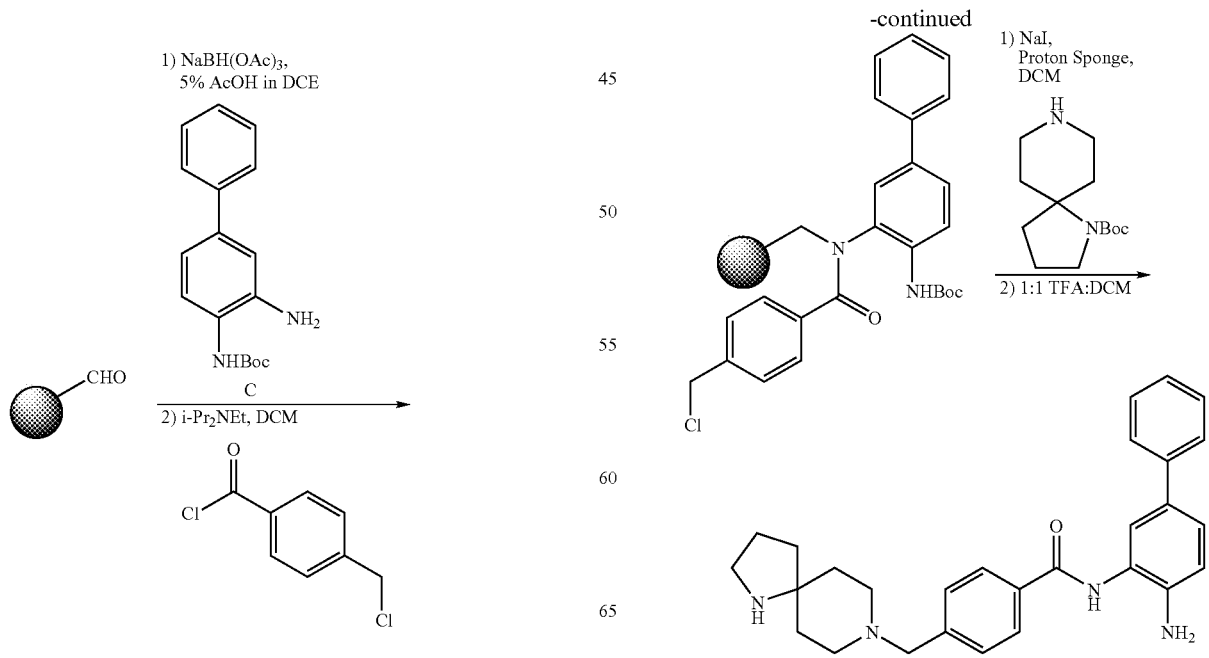

N-(4-Aminobiphenyl-3-yl)-4-(1,8-diazaspiro[4.5]dec-8-ylmethyl)benzamide

The FDMP stratospheres resin (loading 1.5 mmol/g) (67 mg, 0.10 mmol), 137 mg (0.5 mmol) of tert-butyl (3-amino-1-phenyl-1H-pyrazol-4-yl)carbamate, and 1 ml of 5% AcOH in DCE was added to a scintillation vial and allowed to shake overnight at room temperature. 106 mg (0.5 mmol) of NaBH(OAc)$_3$ was added to the vial in 1 ml of 5% AcOH in DCE. The vial was capped and vented, and allowed to react for 3 days at room temperature. The resin was washed with each of the following solvents 3× each and dried in vacuo: DMF, MeOH, H$_2$O, MeOH, and DCM.

The resin from the previous step (0.1 mmol) was added to a scintillation vial along with 2 ml of DCM and 51 mg (0.4 mmol) of DIEA. The vial was shaken for 1 minute and 38 mg (0.2 mmol) of 4-chloromethyl benzoyl chloride was added. The vial was capped and vented, and allowed to react overnight at room temperature. The resin was washed with each of the following solvents 3× each and dried in vacuo: DCM, DMF, H$_2$O, MeOH, and DCM.

The resin from the previous step (0.1 mmol) was added to a scintillation vial along with 214 mg (1.0 mmol) of proton sponge, 45 mg (0.3 mmol) of NaI, 120 mg (0.5 mmol) of tert-butyl 1,8-diazaspiro[4.5]decane-1-carboxylate, and 2 ml of DMF. The resin was washed with each of the following solvents three times each and dried in vacuo: DMF, H$_2$O, MeOH, and DCM.

The resin from the previous step (0.1 mmol) was cleaved with 3 ml of 1:1 DCM:TFA for 2 hours at room temperature. The filtrate was collected and purified by HPLC to yield the product, N-(4-aminobiphenyl-3-yl)-4-(1,8-diazaspiro[4.5]dec-8-ylmethyl)benzamide, as a white solid: MS (ESI+): cal'd [M+H]$^+$ 441.3, obs'd 441.3.

The compounds described in the following table were prepared by methods analogous to those synthetic methods described above, but using the appropriate starting materials.

TABLE 15

| Compound | Forms Prepared | Chemical Name | MS Data |
|---|---|---|---|
| 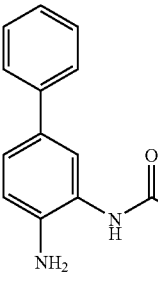 | neutral | N-(4-aminobiphenyl-3-yl)-4-(2,8-diazaspiro[4.5]dec-8-ylmethyl)benzamide | Cal'd [M$^+$ + 1] 441.3, Obs'd 441.3 |
| 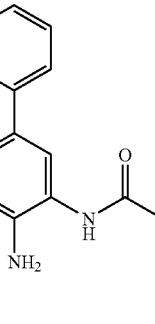 | neutral | N-(4-aminobiphenyl-3-yl)-4-[(4-oxo-1-phenyl-1,3,8-triazaspiro[4.5]dec-8-yl)methyl]benzamide | Cal'd [M$^+$ + 1] 532.3, Obs'd 532.2 |
| 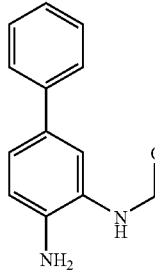 | neutral | N-(4-aminobiphenyl-3-yl)-4-(1,8-diazaspiro[4.5]dec-8-ylmethyl)benzamide | Cal'd [M$^+$ + 1] 441.3, Obs'd 441.3 |

TABLE 15-continued

| Compound | Forms Prepared | Chemical Name | MS Data |
|---|---|---|---|
| (structure with 2-thienyl) | neutral | N-[2-amino-5-(2-thienyl)phenyl]-4-(1,8-diazaspiro[4.5]dec-8-ylmethyl)benzamide | Cal'd [M$^+$ + 1] 447.2, Obs'd 447.3 |
| (structure with 3-thienyl) | neutral | N-[2-amino-5-(3-thienyl)phenyl]-4-(1,8-diazaspiro[4.5]dec-8-ylmethyl)benzamide | Cal'd [M$^+$ + 1] 447.2, Obs'd 447.3 |

EXAMPLE 18

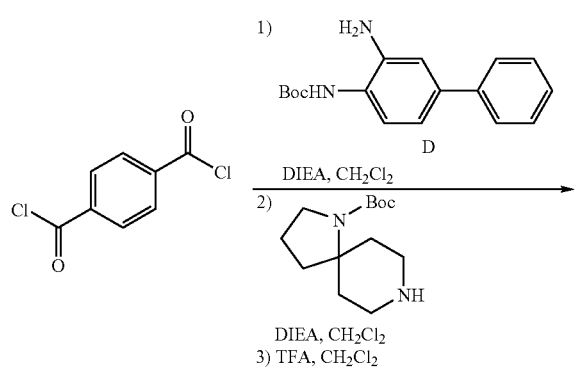

N-(4-aminobiphenyl-3-yl)-4-(1,8-diazaspiro[4.5]dec-8-ylcarbonyl)benzamide

To a solution of stirring terephthaloyl chloride (50 mg, 0.246 mmol) in 3 mL dichloromethane was added tert-butyl (3-aminobiphenyl-4-yl)carbamate (70 mg, 0.246 mmol) slowly over a period of 10 minutes, followed by the addition of diisopropylethylamine (43 µL, 0.246 mmol). The reaction mixture was allowed to stir for 30 min. at room temperature. Tert-butyl 1,8-diazaspiro[4,5]decane-1-carboxylate (59 mg, 0.246 mmol) was then added, followed by the addition of diisopropylethylamine (43 µL, 0.246 mmol). The reaction mixture was allowed to stir for 1 hour at room temperature. The reaction mixture became cloudy. Argonaut MP-Carbonate scavenging resin (255 mg, 0.738 mmol) was then added and stirred overnight at room temperature. The mixture was then fully dissolved by adding 3 mL dimethylformamide, filtered from scavenging resin, and concentrated. Added dichloromethane (1 mL) and stirred to form suspension, then treated with trifluoroacetic acid (1 mL). The reaction mixture was concentrated after 2 hours of stirring at room temperature and the crude residue was purified by reverse-phase chromatography (5-75-95% acetonitrile/water with 0.1% formic acid). The appropriate fractions were combined and lyophilized. MS (ESI+): cal'd [M+H]+ 455.2, obs'd 455.1.

The compounds described in the following table were prepared by methods analogous to those synthetic methods described above, but using the appropriate starting materials.

TABLE 16

| Compound | Forms Prepared | Chemical Name | MS Data |
|---|---|---|---|
| 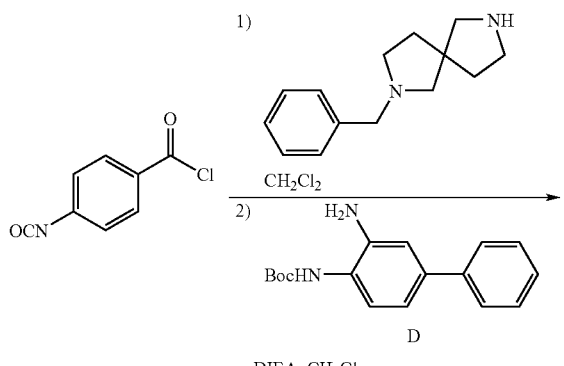 | Neutral | N-(4-aminobiphenyl-3-yl)-4-(2,7-diazaspiro[3.5]non-7-ylcarbonyl)benzamide | Cal'd [M⁺ + 1] 441.2, Obs'd 441.3 |

EXAMPLE 19

N-(4-{[(4-aminobiphenyl-3-yl)amino]carbonyl}phenyl)-7-benzyl-2,7-diazaspiro[4.4]nonane-2-carboxamide

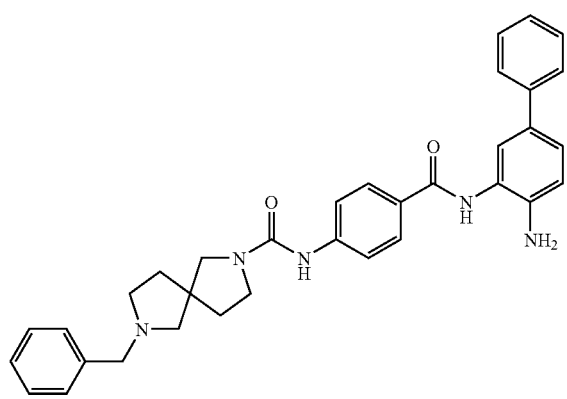

To a solution of stirring 4-isocyanatobenzoyl chloride (50 mg, 0.275 mmol) in 3 mL of dichloromethane was added 2-benzyl-2,7-diazaspiro[4,4]nonane (60 mg, 0.275 mmol) slowly over a period of 10 minutes. The reaction mixture was allowed to stir for 30 min. at room temperature. Tert-butyl (3-aminobiphenyl-4-yl)carbamate (78.2 mg, 0.275 mmol) was then added, followed by the addition of diisopropylethylamine (48 µL, 0.275 mmol). The reaction mixture was allowed to stir for 1 hour at room temperature. Argonaut MP-Carbonate scavenging resin (285 mg, 0.825 mmol) was then added and stirred overnight at room temperature. The mixture was then filtered from scavenging resin and concentrated. Added dichloromethane (1 mL) and stirred, then treated with trifluoroacetic acid (1 mL). The reaction mixture was concentrated after 2 hours of stirring at room temperature and the crude residue was purified by reverse-phase chromatography (5-50-95% acetonitrile/water with 0.1% formic acid). The appropriate fractions were combined and lyophilized. MS (ESI+): cal'd [M+H]+546.3, obs'd 546.2.

The compounds described in the following table were prepared by methods analogous to those synthetic methods described above, but using the appropriate starting materials.

TABLE 17

| Compound | Forms Prepared | Chemical Name | MS Data |
|---|---|---|---|
| 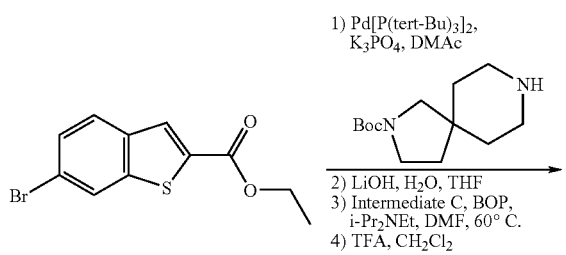 | Neutral | N-(4-{[(4-aminobiphenyl-3-yl)amino]carbonyl}phenyl)-2,7-diazaspiro[3.5]nonane-7-carboxamide | Cal'd [M+ + 1] 456.2, Obs'd 456.3 |

EXAMPLE 20

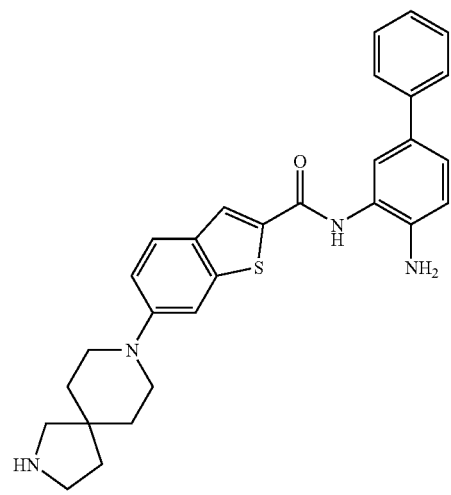

N-(4-Aminobiphenyl-3-yl)-6-(2,8-diazaspiro[4.5]dec-8-yl)-1-benzothiophene-2-carboxamide Ethyl 6-bromo-1-benzothiophene-2-carboxylate was prepared by the following procedure: Sodium hydride (60% dispersion in mineral oil, 0.73 g, 18.3 mmol) was suspended in DMSO (10 mL) and ethyl mercaptoacetate (1.11 mL, 10.1 mmol) was added potionwise using a water bath to moderate the exotherm. On complete addition, the water bath was removed and stirring continued for 15 minutes. A solution of 4-bromo-2-fluorobenzaldehyde (1.86 g, 9.16 mmol) in DMSO (2 mL) was added in one portion. The dark solution was stirred for 15 minutes before pouring into cold water (300 mL). The products were extracted into $Et_2O$ (2×200 mL). The combined organic extracts were washed with brine, dried over $MgSO_4$ and concentrated in vacuo. Purification of the residue by MPLC gave the desired product (pale yellow solid). $^1$H NMR (DMSO-$d_6$) δ 8.37 (d, J=1.8 Hz, 1H), 8.17 (s, 1H), 7.94 (d, J=8.4 Hz, 1H), 7.60 (dd, J=8.4, 1.8 Hz, 1H), 4.32 (q, J=7.2 Hz, 2H), 1.30 (t, J=7.2 Hz, 3H).

A mixture of ethyl 6-bromo-1-benzothiophene-2-carboxylate (250 mg, 0.88 mmol), tert-butyl 2,8-diazaspiro[4.5]decane-2-carboxylate (200 mg, 0.83 mmol), and $K_3PO_4$ (1.00 g, 4.72 mmol) in 2 mL of DMAc was deoxygenated by the freeze-pump-thaw method. The mixture was treated with Pd[P(tert-Bu)$_3$]$_2$ (130 mg, 0.250 mmol) and stirred at 90° C. overnight. The reaction mixture was partitioned between EtOAc and sat'd $NaHCO_3$, the organic layer dried ($Na_2SO_4$), filtered and concentrated. The residue was dissolved in 1 mL of MeOH, 1 mL of THF and 1 mL of $H_2O$, treated with LiOH monohydrate (100 mg, 2.40 mmol) and stirred for 12 h. The mixture was poured into EtOAc and washed with 2 N HCl, water, dried ($Na_2SO_4$), filtered and concentrated. The oily residue was dissolved in 2 mL of DMF, treated with intermediate C (200 mg, 0.980 mmol), BOP (300 mg, 0.679 mmol), i-Pr$_2$NEt (0.250 mL, 1.41 mmol) and stirred for 1 day at ambient temperature followed by 5 days at 60° C. The mixture was partitioned between EtOAc and sat'd $NaHCO_3$, the organic layer was dried ($Na_2SO_4$) and concentrated. Chromatography on $SiO_2$ (0 to 100% EtOAc/$CH_2Cl_2$) gave pure intermediate. The oil was stirred in 2 mL of 1:1 TFA/$CH_2Cl_2$ for 1 h and concentrated. The oil was dissolved in EtOAc, washed with sat'd $NaHCO_3$, dried ($Na_2SO_4$) and concentrated, providing the title compound: MS (ESI+): cal'd [M+H]$^+$ 483.2, obs'd 483.3.

EXAMPLE 21

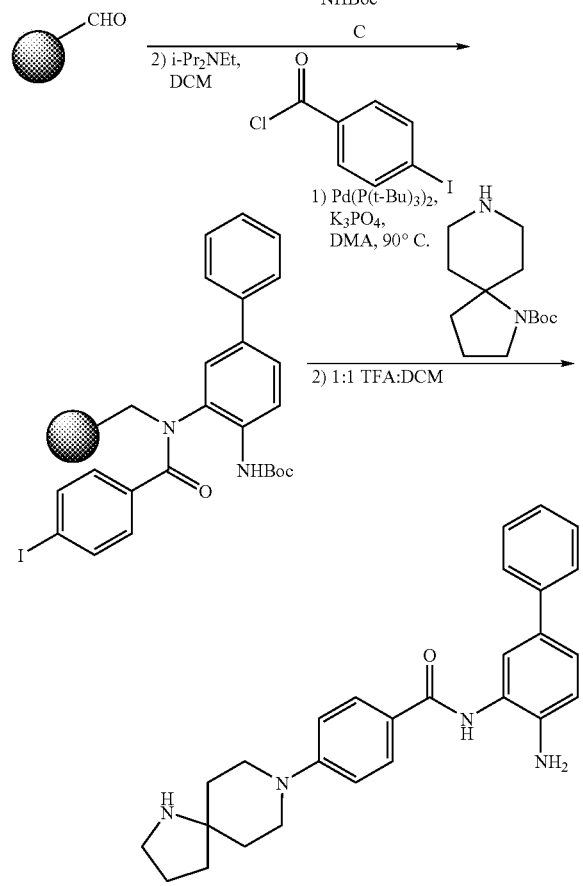

N-(4-Aminobiphenyl-3-yl)-4-(1,8-diazaspiro[4.5]dec-8-yl)benzamide

FDMP stratospheres resin (loading 1.5 mmol/g) (67 mg, 0.10 mmol), 137 mg (0.5 mmol) of tert-butyl (3-amino-1-phenyl-1H-pyrazol-4-yl)carbamate, and 1 ml of 5% AcOH in DCE was added to a scintillation vial and allowed to shake overnight at room temperature. 106 mg (0.5 mmol) of NaBH(OAc)$_3$ was added to the vial in 1 ml of 5% AcOH in DCE. The vial was capped and vented, and allowed to react for 3 days at room temperature. The resin was washed with each of the following solvents 3× each and dried in vacuo: DMF, MeOH, H$_2$O, MeOH, and DCM.

The resin from the previous step (0.1 mmol) was added to a scintillation vial along with 2 ml of DCM and 51 mg (0.4 mmol) of DIEA. The vial was shaken for 1 minute and 53 mg (0.2 mmol) of 4-iodobenzoyl chloride was added. The vial was capped and vented, and allowed to react overnight at room temperature. The resin was washed with each of the following solvents 3× each and dried in vacuo: DCM, DMF, H$_2$O, MeOH, and DCM Resin from the previous step (0.1 mmol) was added to a scintillation vial along with 120 mg (0.5 mmol) of tert-Butyl 1,8-diazaspiro[4.5]decane-1-carboxylate, 85 mg (0.4 mmol) of K$_3$PO$_4$, 26 mg (0.05 mmol) Pd(P(t-Bu)$_3$)$_2$, and 2 ml of DMA. The vial was flushed with Argon and heated to 90° C. The reaction was allowed to proceed overnight at 90° C. The resin was washed with each of the following solvents three times each and dried in vacuo: DMF, H$_2$O, MeOH, and DCM.

Resin (0.1 mmol) from the previous step was cleaved with 3 ml of 1:1 DCM:TFA for 2 hours at room temperature. The filtrate was collected and purified by HPLC to yield the product, N-(4-aminobiphenyl-3-yl)-4-(1,8-diazaspiro[4.5]dec-8-yl)benzamide, as a white solid: MS (ESI+): cal'd [M+H]$^+$ 427.2, obs'd 427.2.

The compounds described in the following table were prepared by methods analogous to those synthetic methods described above, but using the appropriate starting materials.

TABLE 18

| Compound | Forms Prepared | Chemical Name | MS Data |
|---|---|---|---|
| 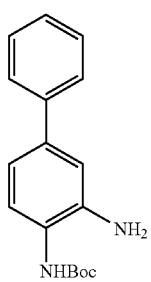 | Neutral | N-(4-aminobiphenyl-3-yl)-4-(2,8-diazaspiro[4.5]dec-8-yl)benzamide | Cal'd [M$^+$ + 1] 427.2, Obs'd 427.2 |

TABLE 18-continued

| Compound | Forms Prepared | Chemical Name | MS Data |
|---|---|---|---|
| (structure shown) | Neutral | N-[2-amino-5-(2-thienyl)phenyl]-4-(1,8-diazaspiro[4.5]dec-8-yl)benzamide | Cal'd [M+ + 1] 432.2, Obs'd 432.2 |

EXAMPLE 22

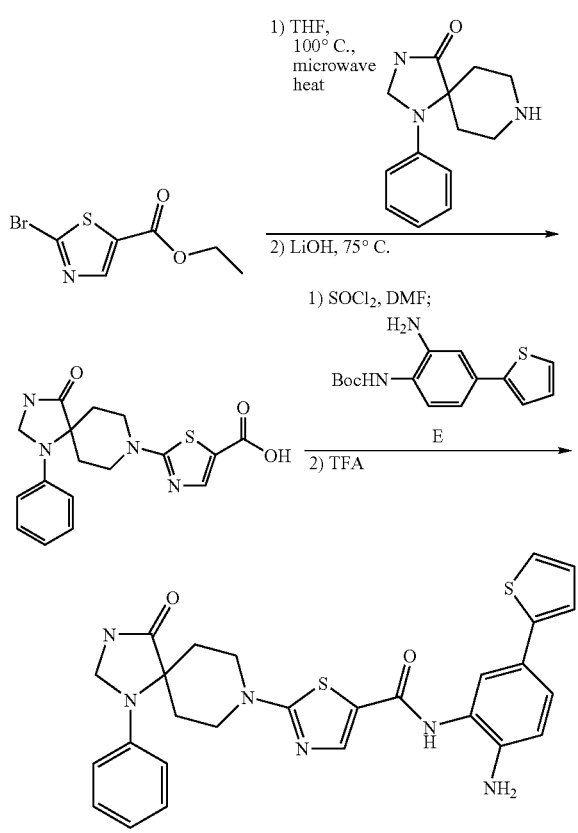

N-(2-Amino-5-thien-2-ylphenyl)-2-(4-oxo-1-phenyl-1,3,8-triazaspiro[4.5]dec-8-yl)-1,3-thiazole-5-carboxamide Ethyl 2-bromo-1,3-thiazole-5-carboxylate (1.0 g, 4.2 mmol) was made 2M in THF and to this stirring solution was added 3 equivalents 1-phenyl-1,3,8-triazaspiro[4.5]decan-4-one (2.94 g, 12.7 mmol). The resulting mixture was heated to 100° C. for 30 mins in the microwave. The reaction mixture was partitioned between ethyl acetate and water. The organic layer was washed with saturated aqueous sodium bicarbonate, brine, then dried over anhydrous magnesium sulfate and concentrated in vacuo to give an oily residue. The residue was purified by MPLC (50-100% EtOAc:Hex): MS (ESI+): cal'd [M+H]+ 387.1, obs'd 387.1.

Ethyl 2-(4-oxo-1-phenyl-1,3,8-triazaspiro[4.5]dec-8-yl)-1,3-thiazole-5-carboxylate (0.75 g, 1.9 mmol) was made 0.25 M in 1,4-dioxane and to this stirring solution was added 3 equivalents 3M Lithium hydroxide (1.9 mL, 5.8 mmol). The resulting mixture was microwaved at 75° C. for 1 hour. The reaction mixture was then neutralized to pH=6 with 1N aqueous HCl and a white precipitate came out of solution. The precipitate was filtered off and dried in vacuo to give 2-(4-oxo-1-phenyl-1,3,8-triazaspiro[4.5]dec-8-yl)-1,3-thiazole-5-carboxylic acid. The material was carried on without further purification: MS (ESI+): cal'd [M+H]+ 359.1, obs'd 359.1.

2-(4-oxo-1-phenyl-1,3,8-triazaspiro[4.5]dec-8-yl)-1,3-thiazole-5-carboxylic acid (60 mg, 0.16 mmol) was made 0.25 M in anhydrous DCM and to this stirring solution was added catalytic DMF followed by 3 equivalents thionyl chloride (179 mg, 1.5 mmol). The resulting solution was stirred at ambient temperature under nitrogen for 1 hour. The reaction mixture was then concentrated in vacuo and azeotroped once with toluene to remove excess thionyl chloride. The residue was made 0.5M in anhydrous DCM and to this stirring solution was added 3 equivalents triethylamine (48 mg, 0.48 mmol) followed by 1 equivalent tert-butyl 2-amino-4-thien-2-ylphenylcarbamate (30 mg, 0.16 mmol). The resulting mixture was stirred at ambient temperature for 14 hours. The reaction mixture was then diluted with 4M TFA in DCM and allowed to stir at ambient temperature. After one hour the reaction mixture was concentrated in vacuo and purified by reverse phase chromatography: MS (ESI+): cal'd [M+H]+ 531.1, obs'd 531.1.

The compounds described in the following table were prepared by methods analogous to those synthetic methods described above, but using the appropriate starting materials.

TABLE 19

| Compound | Forms Prepared | Chemical Name | MS Data |
|---|---|---|---|
|  | TFA | N-(4-amino-1-phenyl-1H-pyrazol-3-yl)-2-(4-oxo-1-phenyl-1,3,8-triazaspiro[4.5]dec-8-yl)-1,3-thiazole-5-carboxamide | Cal'd [M$^+$ + 1] 515.2, Obs'd 515.1 |

EXAMPLE 23

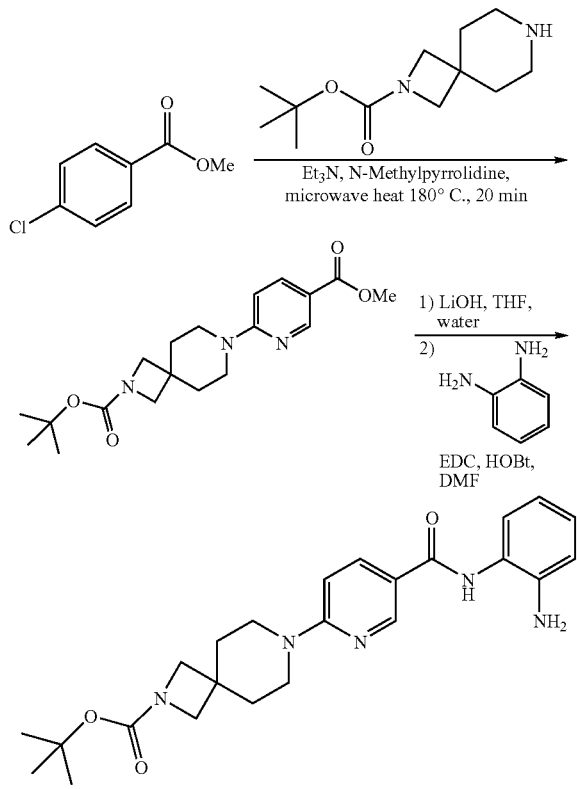

tert-Butyl 7-(5-{[(2-Aminophenyl)amino]carbonyl}pyridine-2-yl)-2,7-diaza-spiro[3.5]nonane-2-carboxylate A mixture of tert-butyl 2,7-diazaspiro[3.5]nonane (660 mg, 2.91 mmol), methyl 6-chloronicotinate (500 mg, 2.91 mmol) and Et$_3$N (0.487 mL, 3.50 mmol) in 2 mL of N-methylpyrrolidine was stirred under microwave irradiation for 20 min at a temperature of 180° C. The mixture was poured into EtOAc and washed with sat'd NaHCO$_3$, dried (MgSO$_4$), filtered and concentrated, giving tert-butyl 7-[5-(methoxycarbonyl)pyridine-2-yl]-2,7-diazaspiro[3.5]nonane-2-carboxylate. The methyl ester was dissolved in 2 mL of 1:1 THF/water, treated with LiOH.H$_2$O (26 mg, 0.62 mmol) and stirred for 20 hours. The mixture was poured into EtOAc and washed with 1M HCl followed by brine, dried (MgSO$_4$), filtered and concentrated, providing 6-[2-(tert-butoxycarbonyl)-2,7-diazaspiro[3.5]non-7-yl]nicotinic acid. A mixture of the carboxylic acid in 2 mL of DMF was treated with EDC (132 mg, 0.69 mmol), HOBt (93 mg, 0.69 mmol) and phenylenediamine (125 mg, 1.15 mmol), stirred for 15 h at room temperature. The reaction mixture was then diluted with EtOAc and washed with sat.'d NaHCO$_3$, dried (MgSO$_4$), filtered and concentrated. The crude oil was purified by reverse phase flash chromatography (10-100% MeCN/H$_2$O with 0.05% TFA) and formation of the desired product, tert-butyl 7-(5-{[(2-aminophenyl)amino]carbonyl}pyridine-2-yl)-2,7-diazaspiro[3.5]nonane-2-carboxylate, which was confirmed by MS (ESI+): cal'd [M+H]$^+$ 438.2, obs'd 438.3.

EXAMPLE 24

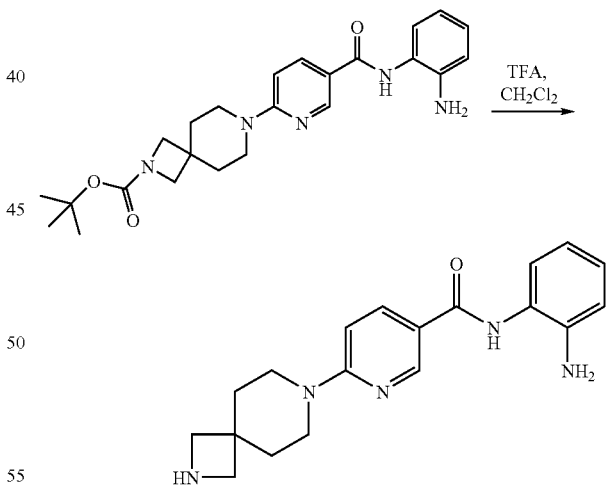

N-(2-Aminophenyl)-6-(2,7-diazaspiro[3.5]non-7-yl)nicotinamide tert-Butyl 7-(5-{[(2-aminophenyl)amino]carbonyl}pyridine-2-yl)-2,7-diazaspiro[3.5]nonane-2-carboxylate (10 mg, 0.023 mmol) was treated with with 1:1 TFA/CH$_2$Cl$_2$, stirred for 1 h and concentrated. Neutralization with EtOAc/sat'd NaHCO$_3$ extraction and drying (MgSO$_4$) gave the target spirocyclic compound: MS (ESI+): cal'd [M+H]$^+$ 338.2, obs'd 338.2.

EXAMPLE 25

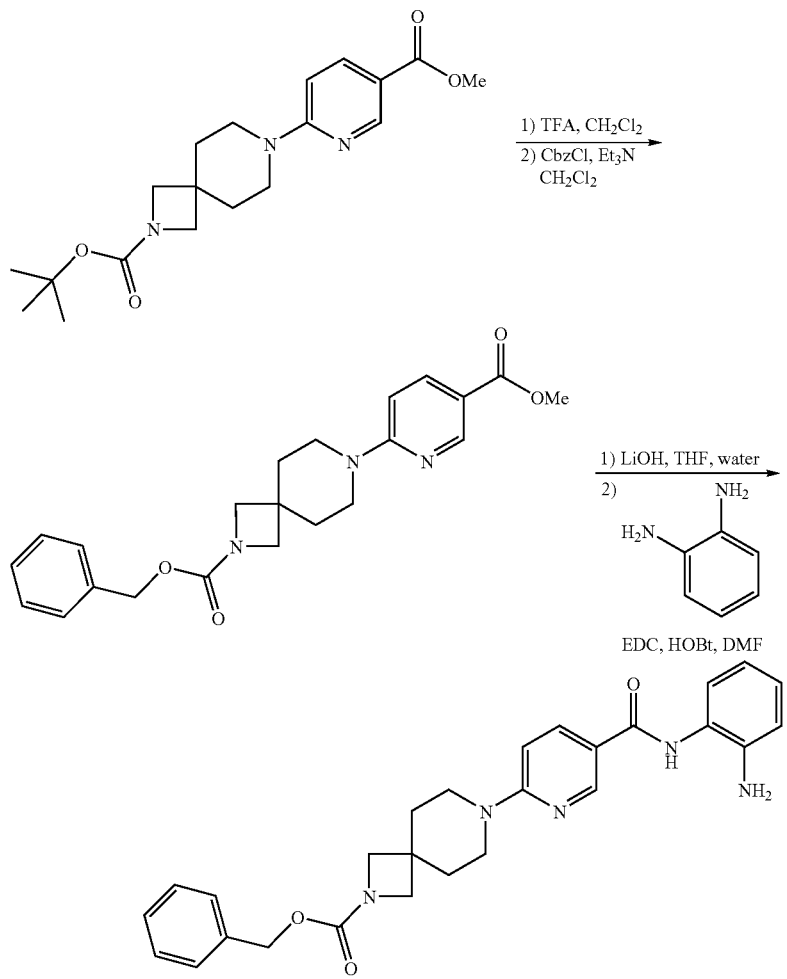

Benzyl 7-(5-{[(2-Aminophenyl)amino]carbonyl}pyridine-2-yl)-2,7-diazaspiro-[3.5]nonane-2-carboxylate tert-Butyl 7-[5-(methoxycarbonyl)pyridine-2-yl]-2,7-diazaspiro[3.5]nonane-2-carboxylate (100 mg, 0.28 mmol) was treated with with 1:1 TFA/CH$_2$Cl$_2$, stirred for 1 h and concentrated. Neutralization with EtOAc/sat'd NaHCO$_3$ extraction and drying (MgSO$_4$) gave the intermediate spiroamine. A solution of the spiroamine (100 mg, 0.28 mmol) in 5 mL of CH$_2$Cl$_2$ was treated with CbzCl (0.058 mL, 0.42 mmol) and Et$_3$N (0.193 mL, 1.38 mmol) and stirred for 1 h at room temperature. The reaction mixture was partitioned between EtOAc and saturated NaHCO$_3$, the organic layer was dried (MgSO$_4$), filtered and concentrated. Formation of the Cbz-protected spirocycle was confirmed by MS (ESI+): cal'd [M+H]$^+$ 396.2, exp. 396.2. Benzyl 7-[5-(methoxycarbonyl)pyridine-2-yl]-2,7-diazaspiro[3.5]nonane-2-carboxylate was dissolved in 2 mL of 1:1 THF/water, treated with LiOH.H$_2$O (26 mg, 0.62 mmol) and stirred for 20 hours, after which the mixture was concentrated, azeotropically dried with MeOH and placed under vacuum for 3 h. A mixture of the residue in 2 mL of DMF was treated with EDC (752 mg, 3.9 mmol), HOBt (532 mg, 3.9 mmol) and phenylenediamine (709 mg, 6.6 mmol), stirred for 15 h and concentrated to dryness. Reverse-phase chromatography (10-100% water/MeCN with 0.05% TFA) gave the desired product, benzyl 7-(5-{[(2-aminophenyl)amino]carbonyl}pyridine-2-yl)-2,7-diazaspiro[3.5]nonane-2-carboxylate, which was confirmed by MS (ESI+): cal'd [M+H]$^+$ 472.2, obs'd 472.2.

EXAMPLE 26

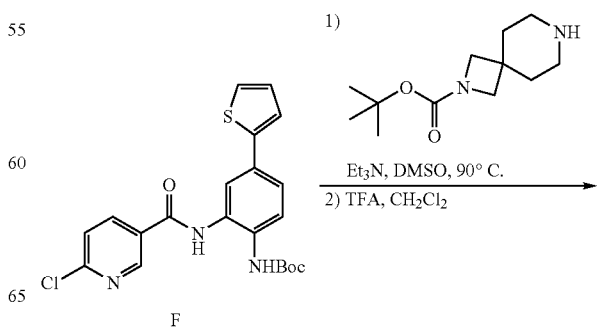

-continued

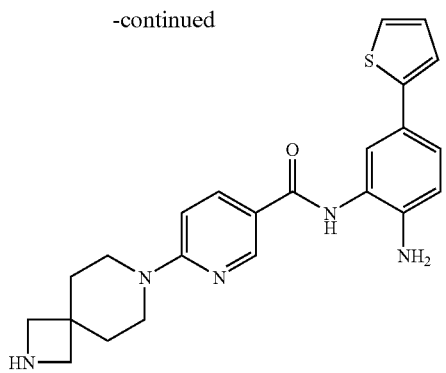

N-[2-Amino-5-(2-thienyl)phenyl]-6-(2,7-diazaspiro[3.5]non-7-yl)nicotinamide tert-Butyl [2-{[(6-chloropyridin-3-yl)carbonyl]amino}-4-(2-thienyl)phenyl]carbamate F (20 mg, 0.088 mmol) was dissolved in 1 mL of DMSO and treated with Et$_3$N(0.010 mL) and tert-butyl 2,7-diazaspiro[3.5]nonane-2-carboxylate (20 mg, 0.047 mmol). The mixture was stirred at 90° C. for 18 h, partitioned between EtOAc and saturated NaHCO$_3$, dried (MgSO$_4$), filtered and concentrated), concentrated and the residue was purified by chromatography on SiO$_2$ (EtOAc/CH$_2$Cl$_2$, 0% to 100%). The residue was dissolved in 1 mL of 1:1 TFA/CH$_2$Cl$_2$, stirred for 1 h and concentrated. Neutralization with EtOAc/sat'd NaHCO$_3$ extraction and drying (MgSO$_4$) gave desired product, N-[2-amino-5-(2-thienyl)phenyl]-6-(2,7-diazaspiro[3.5]non-7-yl)nicotinamide, which was confirmed by MS (ESI+): cal'd [M+H]$^+$ 420.2, obs'd 420.1.

The compounds described in the following table were prepared by methods analogous to those synthetic methods described above, but with intermediates tert-butyl [2-{[(6-chloropyridin-3-yl)carbonyl]amino}-4-(3-thienyl)phenyl]carbamate D or tert-butyl [3-{[(6-chloropyridin-3-yl)carbonyl]amino}biphenyl-4-yl)carbamate H.

TABLE 20

| Compound | Forms Prepared | Chemical Name | MS Data |
| --- | --- | --- | --- |
|  | Neutral | N-[2-amino-5-(3-thienyl)phenyl]-6-(2,7-diazaspiro[3.5]non-7-yl)nicotinamide | Cal'd [M$^+$ + 1] 420.2, Obs'd 420.1 |
|  | Neutral | N-[2-amino-5-(2-thienyl)phenyl]-6-(2,7-diazaspiro[3.5]non-7-yl)nicotinamide | Cal'd [M$^+$ + 1] 420.2, Obs'd 420.2 |
|  | Neutral | N-(4-aminobiphenyl-3-yl)-6-(2,7-diazaspiro[3.5]non-7-yl)nicotinamide | Cal'd [M$^+$ + 1] 414.2, Obs'd 414.2 |

EXAMPLE 27

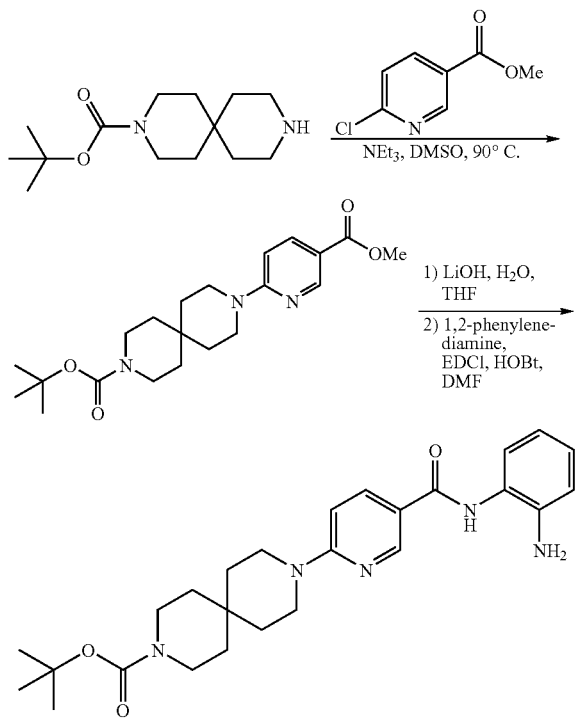

tert-butyl 9-(5-{[(2-aminophenyl)amino]carbonyl}pyridin-2-yl)-3,9-diazaspiro[5.5]-undecane-3-carboxylate A mixture of methyl 6-chloronicotinate (800 mg, 3.15 mmol), NEt₃ (1.00 mL, 7.19 mmol) and tert-butyl 3,9-diazaspiro[5.5]undecane-3-carboxylate (1.00 g, 3.94 mmol) in 5 mL of DMSO was heated to 100° C. for 1 h with microwave irradiation. The reaction mixture was poured into EtOAc and washed with 2 N NaOH, 2 H HCl, brine and dried (Na₂SO₄), filtered and concentrated giving tert-butyl 9-[5-(methoxycarbonyl)pyridin-2-yl]-3,9-diazaspiro[5.5]undecane-3-carboxylate.

A solution of the above compound (100 mg) was stirred with LiOH.H₂O (30 mg, 0.71 mmol) in 1 mL of THF and 1 mL of water for 12 h, then concentrated to dryness. The residue was dissolved in 3 mL of DMF and treated with EDC (250 mg, 1.31 mmol), HOBt (100 mg, 0.74 mmol) and phenylenediamine (100 mg, 0.93 mmol). The mixture was stirred for 15 h, poured into EtOAc, washed with sat'd NaHCO₃, dried (Na₂SO₄), filtered and concentrated. Trituration with ether gave the title compound; MS (ESI+): cal'd [M+1]⁺ 465.3, obs'd 465.3.

The compounds described in the following table were prepared by methods analogous to those synthetic methods described above, but using the appropriate starting materials.

TABLE 21

| Compound | Forms Prepared | Chemical Name | MS Data |
|---|---|---|---|
|  | neutral | tert-butyl 2-(5-{[(2-aminophenyl)amino]carbonyl}pyridin-2-yl)-2,8-diazaspiro[4.5]decane-8-carboxylate | Cal'd [M⁺ + 1] 452.3, Obs'd 452.3 |
|  | neutral | tert-butyl 2-(5-{[(2-aminophenyl)amino]carbonyl}pyridin-2-yl)-2,7-diazaspiro[4.5]decane-7-carboxylate | Cal'd [M⁺ + 1] 452.3, Obs'd 452.3 |

TABLE 21-continued

| Compound | Forms Prepared | Chemical Name | MS Data |
|---|---|---|---|
| | neutral | tert-butyl 9-(5-{[(2-aminophenyl)amino]carbonyl}pyridin-2-yl)-3,9-diazaspiro[5.5]undecane-3-carboxylate | Cal'd [M⁺ + 1] 466.3, Obs'd 466.3 |
| | neutral | N-(2-aminophenyl)-6-(8-benzyl-2,8-diazaspiro[5.5]undec-2-yl)nicotinamide | Cal'd [M⁺ + 1] 456.3, Obs'd 456.3 |

EXAMPLE 28

N-(2-aminophenyl)-6-(3,9-diazaspiro[5.5]undec-3-yl)nicotinamide

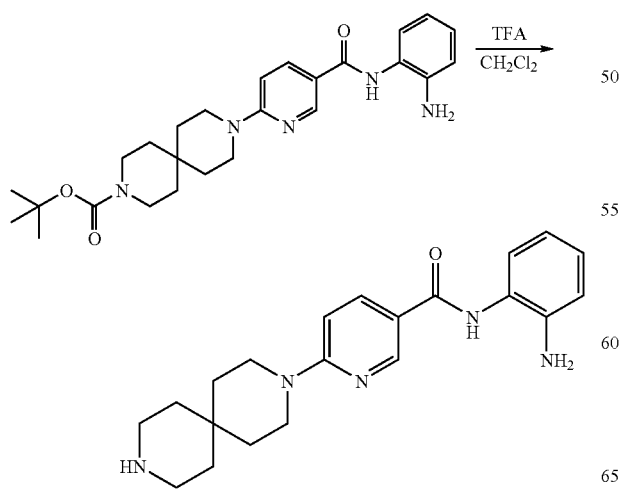

A solution of N-(2-aminophenyl)-6-(3,9-diazaspiro[5.5]undec-3-yl)nicotinamide (10 mg, 0.022 mmol) in 2 mL of 1:1 TFA/CH$_2$Cl$_2$ was stirred for 1 h and concentrated, giving the title compound as a TFA salt; MS (ESI+): cal'd [M+1]⁺ 365.2, obs'd 365.2.

The compounds described in the following table were prepared by methods analogous to those synthetic methods described above, but using the appropriate starting materials.

TABLE 22

| Compound | Forms Prepared | Chemical Name | MS Data |
|---|---|---|---|
| 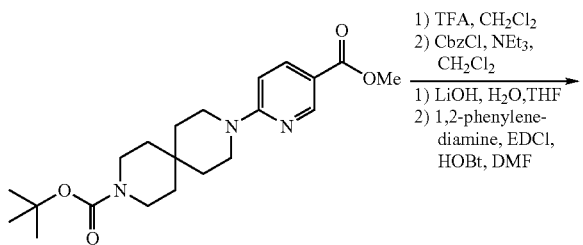 | TFA | N-(2-aminophenyl)-6-(2,7-diazaspiro[3.5]non-2-yl)nicotinamide | Cal'd [M+ + 1] 338.2, Obs'd 338.2 |
| 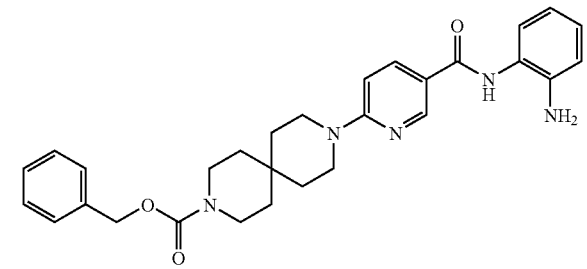 | Neutral | N-(2-aminophenyl)-6-(2,8-diazaspiro[4.5]dec-2-yl)nicotinamide | Cal'd [M+ + 1] 352.2, Obs'd 352.2 |

EXAMPLE 29

Benzyl 9-(5-{[(2-aminophenyl)amino]carbonyl}pyridin-2-yl)-3,9-diazaspiro[5.5]-undecane-3-carboxylate A solution of tert-butyl 9-[5-(methoxycarbonyl)pyridin-2-yl]-3,9-diazaspiro[5.5]undecane-3-carboxylate (100 mg, 0.257 mmol) in 1 mL of $CH_2Cl_2$ and 1 mL of TFA was stirred for 1 h and concentrated. The oil was redissolved in 2 mL of $CH_2Cl_2$ and treated with $NEt_3$ (0.15 mL, 1.08 mmol) and CbzCl (0.060 mL, 0.42 mmol), then stirred for 8 h. The mixture was partitioned between EtOAc and sat'd $NaHCO_3$, dried ($Na_2SO_4$), filtered and concentrated. The residue was stirred in 3 mL of 1:1:1 MeOH/THF/water with $LiOH \cdot H_2O$ (30 mg, 0.71 mmol) for 10 h, concentrated to dryness, dissolved in 2 mL of DMF, treated with EDC (150 mg, 0.79 mmol), HOBt (100 mg, 0.74 mmol), and phenylenediamine (100 mg, 0.93 mmol). The mixture was stirred for 18 h, concentrated, and triturated with methanol giving the title compound; MS (ESI+): cal'd [M+1]+ 500.3, obs'd 500.3.

The compounds described in the following table were prepared by methods analogous to those synthetic methods described above, but using the appropriate starting materials.

TABLE 23

| Compound | Forms Prepared | Chemical Name | MS Data |
|---|---|---|---|
| 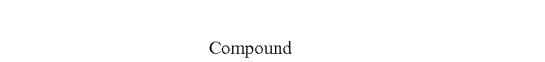 | neutral | benzyl 2-(5-{[(2-aminophenyl)amino]carbonyl}pyridin-2-yl)-2,7-diazaspiro[3.5]nonane-7-carboxylate | Cal'd [M+ + 1] 472.2, Obs'd 472.2 |

TABLE 23-continued

| Compound | Forms Prepared | Chemical Name | MS Data |
|---|---|---|---|
| | neutral | benzyl 2-(5-{[(2-aminophenyl)amino]carbonyl}pyridin-2-yl)-2,7-diazaspiro[4.5]decane-7-carboxylate | Cal'd [M⁺ + 1] 486.2, Obs'd 486.2 |
| | neutral | benzyl 2-(5-{[(2-aminophenyl)amino]carbonyl}pyridin-2-yl)-2,8-diazaspiro[4.5]decane-8-carboxylate | Cal'd [M⁺ + 1] 486.2, Obs'd 486.2 |
| | neutral | N-(2-aminophenyl)-6-[8-(3-phenylpropanoyl)-2,8-diazaspiro[4.5]dec-2-yl]nicotinamide | Cal'd [M⁺ + 1] 484.3, Obs'd 484.2 |

EXAMPLE 30

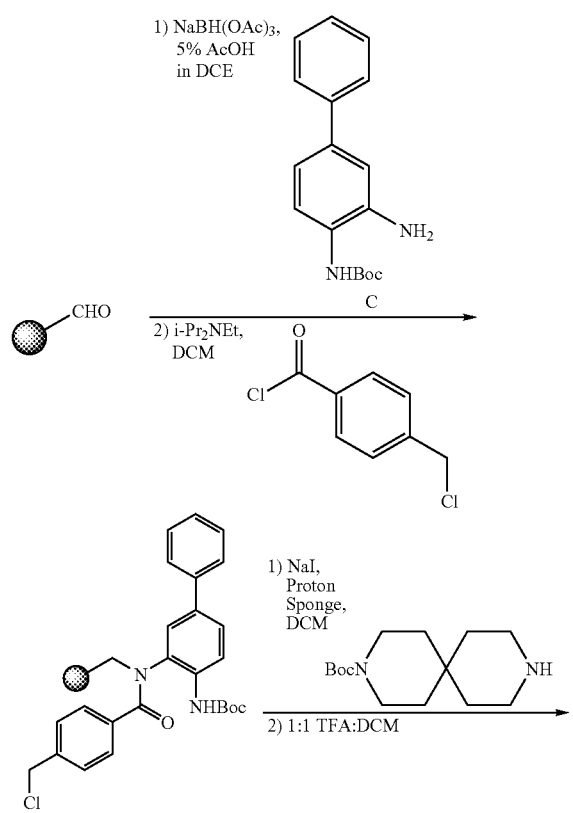

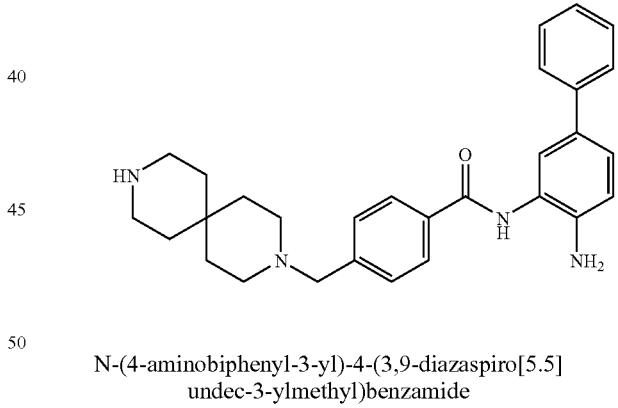

N-(4-aminobiphenyl-3-yl)-4-(3,9-diazaspiro[5.5]undec-3-ylmethyl)benzamide

The FDMP stratospheres resin (loading 1.5 mmol/g) (67 mg, 0.10 mmol), 137 mg (0.5 mmol) of tert-butyl (3-aminobiphenyl-4-yl)carbamate (intermediate C), and 1 ml of 5% AcOH in DCE was added to a scintillation vial and allowed to shake overnight at room temperature. 106 mg (0.5 mmol) of NaBH(OAc)$_3$ was added to the vial in 1 ml of 5% AcOH in DCE. The vial was capped and vented, and allowed to react for 3 days at room temperature. The resin was washed with each of the following solvents 3× each and dried in vacuo: DMF, MeOH, H$_2$O, MeOH, and DCM.

The resin from the previous step (0.1 mmol) was added to a scintillation vial along with 2 ml of DCM and 51 mg (0.4 mmol) of DIEA. The vial was shaken for 1 minute and 38 mg (0.2 mmol) of 4-chloromethyl benzoyl chloride was added.

The vial was capped and vented, and allowed to react overnight at room temperature. The resin was washed with each of the following solvents 3× each and dried in vacuo: DCM, DMF, H₂O, MeOH, and DCM.

The resin from the previous step (0.1 mmol) was added to a scintillation vial along with 214 mg (1.0 mmol) of proton sponge, 45 mg (0.3 mmol) of NaI, 77 mg (0.5 mmol) of tert-butyl 3,9-diazaspiro[5.5]undecane-3-carboxylate, and 2 ml of DMF. The resin was washed with each of the following solvents three times each and dried in vacuo: DMF, H₂O, MeOH, and DCM.

The resin from the previous step (0.1 mmol) was cleaved with 3 ml of 1:1 DCM:TFA for 2 hours at room temperature. The filtrate was collected and purified by HPLC to yield the product, N-(4-aminobiphenyl-3-yl)-4-(3,9-diazaspiro[5.5]undec-3-ylmethyl)benzamide, as a white solid: MS (ESI+): cal'd [M+H]⁺ 455.3, obs'd 455.3.

The compounds described in the following table were prepared by methods analogous to those synthetic methods described above, but using the appropriate starting materials.

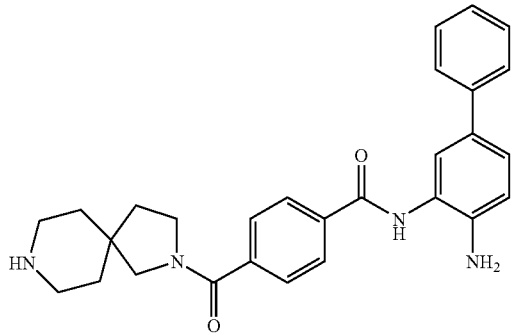

N-(4-Aminobiphenyl-3-yl)-4-(2,8-diazaspiro[4,5]dec-2-ylcarbonyl)benzamide

To a solution of stirring terephthaloyl chloride (338 mg, 1.664 mmol) in 20 mL dichloromethane was added tert-butyl (3-aminobiphenyl-4-yl)carbamate (473 mg, 1.664 mmol) slowly over a period of 10 minutes, followed by the addition of diisopropylethylamine (290 μL, 1.664 mmol). The reaction mixture was allowed to stir for 30 min. at room temperature. Tert-butyl 1,8-diazaspiro[4,5]decane-1-carboxylate (400 mg, 1.664 mmol) was then added, followed by the addition of diisopropylethylamine (290 μL, 1.664 mmol). The reaction mixture was allowed to stir for 1 hour at room temperature. The reaction mixture became cloudy. Argonaut MP-Carbonate scavenging resin (1.72 g, 4.992 mmol) was then added and stirred overnight at room temperature. The mixture was then fully dissolved by adding 20 mL dimethylformamide, filtered from scavenging resin, and concentrated. Added dichloromethane (4 mL) and stirred to form suspension, then treated with trifluoroacetic acid (4 mL). The reaction mixture was concentrated after 2 hours of stirring at room temperature and the crude residue was purified by reverse-phase chromatography (5-70-95% acetonitrile/water with 0.1% formic acid). The appropriate fractions were combined and lyophilized. MS (ESI+): cal'd [M+H]⁺ 455.2, obs'd 455.1.

The compounds described in the following table were prepared by methods analogous to those synthetic methods described above, but using the appropriate starting materials.

TABLE 24

| Compound | Forms Prepared | Chemical Name | MS Data |
|---|---|---|---|
|  | neutral | N-(4-aminobiphenyl-3-yl)-4-(2,7-diazaspiro[4.5]dec-2-ylmethyl)benzamide | Cal'd [M⁺ + 1] 441.3, Obs'd 441.3 |

EXAMPLE 31

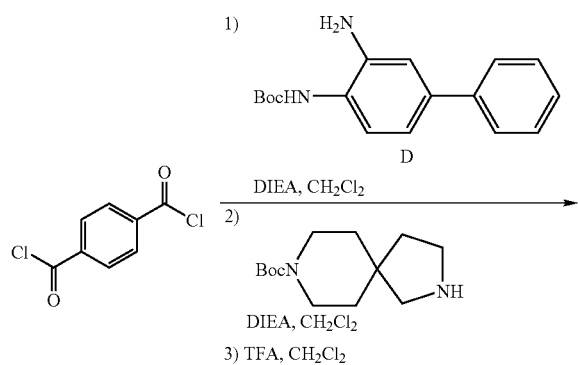

TABLE 25
| Compound | Forms Prepared | Chemical Name | MS Data |
|---|---|---|---|
| | neutral | N-(4-aminobiphenyl-3-yl)-4-(2,7-diazaspiro[4.5]dec-2-ylcarbonyl)benzamide | Cal'd [M⁺ + 1] 455.2, Obs'd 455.1 |
| | neutral | N-(4-aminobiphenyl-3-yl)-4-[(9-benzyl-2,9-diazaspiro[5.5]undec-2-yl)carbonyl]benzamide | Cal'd [M⁺ + 1] 559.3, Obs'd 559.2 |
EXAMPLE 32
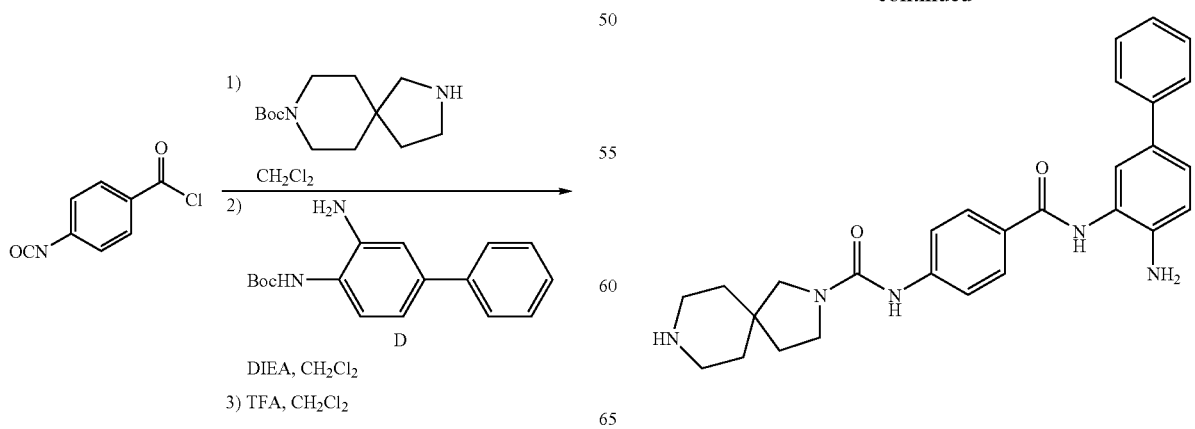

N-(4-{[(4-Aminobiphenyl-3-yl)amino]carbonyl}phenyl)-2,8-diazaspiro[4.5]decane-2-carboxamide To a solution of stirring 4-isocyanatobenzoyl chloride (50 mg, 0.275 mmol) in 3 mL dichloromethane was added tert-butyl 2,8-diazaspiro[4.5]decane-8-carboxylate (60 mg, 0.275 mmol) slowly over a period of 10 minutes. The reaction mixture was allowed to stir for 30 min. at room temperature. Tert-butyl (3-aminobiphenyl-4-yl)carbamate (78.2 mg, 0.275 mmol) was then added, followed by the addition of diisopropylethylamine (48 µL, 0.275 mmol). The reaction mixture was allowed to stir for 1 hour at room temperature. Argonaut MP-Carbonate scavenging resin (285 mg, 0.825 mmol) was then added and stirred overnight at room temperature. The mixture was then filtered from scavenging resin and concentrated. Added dichloromethane (1 mL) and stirred, then treated with trifluoroacetic acid (1 mL). The reaction mixture was concentrated after 2 hours of stirring at room temperature and the crude residue was purified by reverse-phase chromatography (5-50-95% acetonitrile/water with 0.1% formic acid). The appropriate fractions were combined and lyophilized. MS (ESI+): cal'd [M+H]+470.2, obs'd 470.1

The compounds described in the following table were prepared by methods analogous to those synthetic methods described above, but using the appropriate starting materials.

deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, PA). Upon deacetylation of the substrate by incubation with the purified HDAC1 complex, a fluorophore is produced that is directly proportional to the level of deacetylation. Using a substrate concentration at the Km for the enzyme preparation, the deacetylation assay was performed in the presence of increasing concentrations of novel compounds to semi-quantitatively determine the concentration of compound required for 50% inhibition (IC50) of the deacetylation reaction. The compounds of the instant invention described in the Examples and Tables above exhibit histone deacetylase inhibitory activity at concentrations of less than about 1 µM.

EXAMPLE 34

HDAC Inhibition in Cell Lines—ATP Assay

The novel compounds of the present invention were tested for their ability to inhibit proliferation of the human cervical cancer (HeLa) and colon carcinoma (HCT116) cells.

In this assay, also referred to as the Vialight Assay, cellular ATP levels are measured as a means of quantifying cellular

TABLE 26

| Compound | Forms Prepared | Chemical Name | MS Data |
|---|---|---|---|
|  | neutral | N-(4-{[(4-aminobiphenyl-3-yl)amino]carbonyl}-phenyl)-9-benzyl-2,9-diazaspiro[5.5]undecane-2-carboxamide | Cal'd [M+ + 1] 574.3, Obs'd 574.2 |
|  | neutral | N-(4-{[(4-aminobiphenyl-3-yl)amino]carbonyl}-phenyl)-2,7-diazaspiro[4.5]decane-2-carboxamide | Cal'd [M+ + 1] 470.2 Obs'd 470.1 |

EXAMPLE 33

HDAC Inhibition by Novel Compounds—HDAC1-Flag Assay:

Novel compounds were tested for their ability to inhibit histone deacetylase, subtype 1 (HDAC1) using an in vitro proliferation. This assay makes use of a bioluminescent method from Cambrex (ViaLight PLUS, cat. #LT07-121). In the presence of ATP, luciferase converts luciferin to oxyluciferin and light. The amount of light produced (emission at 565 nM) is measured and correlates with a relative amount of proliferation. Human cervical cancer (HeLa) or colon carcinoma (HCT116) cells were incubated with vehicle or increasing concentrations of compound for 48, 72 or 96 hours. Cell proliferation was quantified by adding the cell lysis reagent (provided in the Vialight assay kit) directly to culture wells, followed by addition of the ATP-monitoring reagent (containing luciferase/luciferin). The amount of light produced is then measured (emission at 565 nM). The quantity of light produced, as measured by 565 nM absorbance, is directly proportional to the number of living cells in culture.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:

1. A compound represented by the following structural Formula:

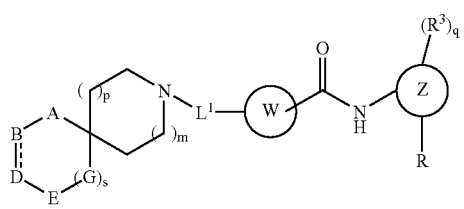

I wherein
A is O, B is $CR^1_2$ or C(O) and D is $NR^{1a}$;
E is a bond;
G is $CR^1_2$;
R is selected from $NH_2$ and OH;
- - - - is an optional double bond;

is an aryl or heteroaryl, optionally substituted with from 1 to 3 substituents selected from $R^7$;

is an aryl or heteroaryl;

$R^1$ is independently selected from
1) hydrogen,
2) $C_1$-$C_6$ alkyl,
3) $(CR^6_2)_nR^{10}$,
4) $(CR^6_2)_nC(O)R^4$,
5) $(CR^6_2)_nC(O)OR^4$,
6) $(CR^6_2)_nC(O)NR^5_2$,
7) $(CR^6_2)_nS(O)_2R^4$,
8) $(CR^6_2)_nOH$, and
9) halo;

$R^{1a}$ is independently selected from
1) hydrogen,
2) $C_1$-$C_6$ alkyl,
3) $(CR^6_2)_nR^{10}$,
4) $(CR^6_2)_nC(O)R^4$,
5) $(CR^6_2)_nC(O)OR^4$,
6) $(CR^6_2)_nC(O)NR^5_2$, and
7) $(CR^6_2)_nS(O)_2R^4$;

$L^1$ is a bond;
$R^3$ is selected from
H,
unsubstituted or substituted $C_1$-$C_6$ alkyl,
unsubstituted or substituted aryl,
unsubstituted or substituted heteroaryl
halo,
CN,
amide,
carboxyl,
$C_1$-$C_7$ alkoxy,
$C_1$-$C_7$ haloalkyl,
$C_1$-$C_7$ haloalkyloxy,
$C_1$-$C_7$ hydroxyalkyl,
$C_1$-$C_7$ alkenyl,
$C_1$-$C_7$ alkynyl,
$C_1$-$C_7$ alkyl-C(=O)O—,
$C_1$-$C_7$ alkyl-C(=O)—,
hydroxyalkoxy,
$C_1$-$C_7$ alkyl-$NHSO_2$—,
$C_1$-$C_7$ alkyl-$SO_2NH$—,
$C_1$-$C_7$ alkylsulfonyl,
$C_1$-$C_7$ alkylamino,
di($C_1$-$C_7$)alkylamino, and
-$L^2$-$R^{12}$;

$R^4$ is independently selected from
1) H,
2) $C_1$-$C_6$alkyl,
3) aryl, and
3) heterocyclyl,
wherein alkyl, aryl or heterocyclyl may be optionally substituted;

$R^5$ is independently selected from
1) hydrogen,
2) $C_1$-$C_6$ alkyl, and
3) aryl,
which may be optionally substituted with 1 to 3 substituents selected from $C_1$-$C_6$ alkyl, aryl, heteroaryl and halo;

$R^6$ is independently selected from
1) hydrogen,
2) $C_1$-$C_6$ alkyl,
3) aryl,
4) $OR^{11}$,
5) halo, and
6) $NR^{11}_2$;
wherein the alkyl or aryl may be optionally substituted with 1 to 3 substituents selected from $C_1$-$C_6$ alkyl, aryl, heteroaryl and halo;

$R^7$ is independently selected from hydrogen, OH, $NR^{11}_2$, nitro, CN, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O) O—, $C_1$-$C_7$ alkyl-C (=O)—, $C_1$-$C_7$ alkynyl, halo group, amide, hydroxyalkoxy, $C_1$-$C_7$ alkyl-$NR^{11}SO_2$—, $C_1$-$C_7$ alkyl-$SO_2NR^{11}$—, $C_1$-$C_7$ alkylsulfonyl, $C_1$-$C_7$ alkylamino and di($C_1$-$C_7$)alkylamino;

$R^{10}$ is independently selected from
1) aryl, and
2) heterocyclyl,
which may be optionally substituted;

$R^{11}$ is independently selected from hydrogen, unsubstituted or substituted $C_1$-$C_6$ alkyl, and unsubstituted or substituted aryl;

$L^2$ is selected from
1) a bond,
2) $C_1$-$C_4$ alkylene,
3) $C_1$-$C_4$ alkynyl,
4) $C_1$-$C_4$ alkenyl,
5) —O—,
6) —S—,
7) —NH—,
8) —C(=O)NH—,
9) —NHC(=O)—,
10) —NHC(=O)NH—,
11) —SO$_2$NH—,
12) —NHSO$_2$—,
13) —SO$_2$—,
14) —C(=O)— and
15) —C(=O)O—;

$R^{12}$ is selected from:
1) substituted or unsubstituted heteroaryl,
2) substituted or unsubstituted heterocyclyl,
3) substituted or unsubstituted aryl, and
4) substituted or unsubstituted $C_3$-$C_8$ cycloalkyl;

m is 1;
n is independently selected from 0, 1, 2, 3 and 4;
p is 1;
q is 1, 2, 3, or 4;
s is 0 or 1;
or a stereoisomer or a pharmaceutically acceptable salt thereof.

2. The compound according to claim 1, represented by Formula II:

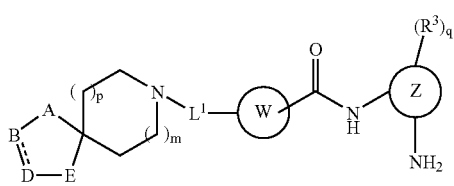

II wherein
A is O, B is $CR^1_2$ or C(O) and D is $NR^{1a}$;
E is a bond;
- - - - is an optional double bond;

is an aryl or heteroaryl, optionally substituted with from 1 to 3 substituents selected from $R^7$;

is an aryl or heteroaryl;

$R^1$ is independently selected from
1) hydrogen,
2) $C_1$-$C_6$alkyl,
3) $(CR^6_2)_nR^{10}$,
4) $(CR^6_2)_nC(O)R^4$,
5) $(CR^6_2)_nC(O)OR^4$,
6) $(CR^6_2)_nC(O)NR^5_2$,
7) $(CR^6_2)_nS(O)_2R^4$,
8) $(CR^6_2)_nOH$, and
9) halo;

$R^{1a}$ is independently selected from
1) hydrogen,
2) $C_1$-$C_6$alkyl,
3) $(CR^6_2)_nR^{10}$,
4) $(CR^6_2)_nC(O)R^4$,
5) $(CR^6_2)_nC(O)OR^4$,
6) $(CR^6_2)_nC(O)NR^5_2$, and
7) $(CR^6_2)_nS(O)_2R^4$;

$L^1$ is a bond;

$R^3$ is selected from
H,
unsubstituted or substituted $C_1$-$C_6$ alkyl,
unsubstituted or substituted aryl,
unsubstituted or substituted heteroaryl
halo,
CN,
amide,
carboxyl,
$C_1$-$C_7$ alkoxy,
$C_1$-$C_7$ haloalkyl,
$C_1$-$C_7$ haloalkyloxy,
$C_1$-$C_7$ hydroxyalkyl,
$C_1$-$C_7$ alkenyl,
$C_1$-$C_7$ alkynyl,
$C_1$-$C_7$ alkyl-C(=O)O—,
$C_1$-$C_7$ alkyl-C(=O)—,
hydroxyalkoxy,
$C_1$-$C_7$ alkyl-NHSO$_2$—,
$C_1$-$C_7$ alkyl-SO$_2$NH—,
$C_1$-$C_7$ alkylsulfonyl,
$C_1$-$C_7$ alkylamino,
di($C_1$-$C_7$)alkylamino, and
-$L^2$-$R^{12}$, $R^4$ is independently selected from
1) H,
2) $C_1$-$C_6$ alkyl,
3) aryl, and
3) heterocyclyl,
wherein alkyl, aryl or heterocyclyl may be optionally substituted;

$R^5$ is independently selected from
1) hydrogen,
2) $C_1$-$C_6$ alkyl, and
3) aryl,
which may be optionally substituted with 1 to 3 substituents selected from $C_1$-$C_6$ alkyl, aryl, heteroaryl and halo;

$R^6$ is independently selected from
1) hydrogen,
2) $C_1$-$C_6$ alkyl,
3) aryl,
4) $OR^{11}$,
5) halo, and
6) $NR^{11}_2$;
wherein the alkyl or aryl may be optionally substituted with 1 to 3 substituents selected from $C_1$-$C_6$ alkyl, aryl, heteroaryl and halo;

$R^7$ is independently selected from hydrogen, OH, $NR^{11}_2$, nitro, CN, carboxyl, $C_1$-$C_7$ alkoxy, $C_1$-$C_7$ alkyl, $C_1$-$C_7$ haloalkyl, $C_1$-$C_7$ haloalkyloxy, $C_1$-$C_7$ hydroxyalkyl, $C_1$-$C_7$ alkenyl, $C_1$-$C_7$ alkyl-C(=O)O—, $C_1$-$C_7$ alkyl-C(=O)—, $C_1$-$C_7$ alkynyl, halo group, amide, hydroxyalkoxy, $C_1$-$C_7$ alkyl-$NR^{11}SO_2$—, $C_1$-$C_7$ alkyl-$SO_2NR^{11}$—, $C_1$-$C_7$ alkylsulfonyl, $C_1$-$C_7$ alkylamino and di($C_1$-$C_7$)alkylamino;

$R^{10}$ is independently selected from
1) aryl, and
2) heterocyclyl,
which may be optionally substituted;

$R^{11}$ is independently selected from hydrogen, unsubstituted or substituted $C_1$-$C_6$ alkyl, and unsubstituted or substituted aryl;

$L^2$ is selected from
1) a bond,
2) $C_1$-$C_4$ alkylene,
3) $C_1$-$C_4$ alkynyl,
4) $C_1$-$C_4$ alkenyl,
5) —O—,
6) —S—,
7) —NH—,
8) —C(=O)NH—,
9) —NHC(=O)—,
10) —NHC(=O)NH—,
11) —$SO_2$NH—,
12) —NH$SO_2$—,
13) —$SO_2$—,
14) —C(=O)— and
15) —C(=O)O—;

$R^{12}$ is selected from:
1) substituted or unsubstituted heteroaryl,
2) substituted or unsubstituted heterocyclyl,
3) substituted or unsubstituted aryl, and
4) substituted or unsubstituted $C_3$-$C_8$ cycloalkyl;

m is 1;
n is independently selected from 0, 1, 2, 3 and 4;
p is 1;
q is 1, 2, 3, or 4;

or a stereoisomer or a pharmaceutically acceptable salt thereof.

3. The compound according to claim 2, represented by Formula III:

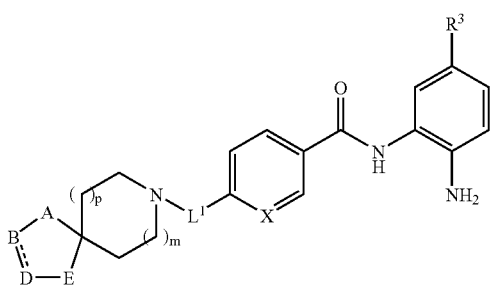

wherein
X is CH or N;
and the remaining substituents are as described in claim 2;

or a stereoisomer or a pharmaceutically acceptable salt thereof.

4. The compound according to claim 3 wherein:
A is O;
B is C(O);
D is $NR^{1a}$;
E is a bond;

or a stereoisomer or a pharmaceutically acceptable salt thereof.

5. The compound of claim 1 selected from
N-[2-Amino-5-(2-thienyl)phenyl]-6-(2-oxo-1-oxa-3,8-diazaspiro[4.5]dec-8-yl)nicotinamide;
N-[2-amino-5-(3-thienyl)phenyl]-6-(2-oxo-1-oxa-3,8-diazaspiro[4.5]dec-8-yl)nicotinamide;
N-[2-amino-5-(2-thienyl)phenyl]-6-(3-methyl-2-oxo-1-oxa-3,8-diazaspiro[4.5]dec-8-yl)nicotinamide;
N-(4-aminobiphenyl-3-yl)-6-(3-methyl-2-oxo-1-oxa-3,8-diazaspiro[4.5]dec-8-yl)nicotinamide; and
N-(4-aminobiphenyl-3-yl)-6-(2-oxo-1-oxa-3,8-diazaspiro[4.5]dec-8-yl)nicotinamide;

or a stereoisomer or a pharmaceutically acceptable salt thereof.

6. A pharmaceutical composition comprising a pharmaceutically effective amount of the compound according to claim 1, and a pharmaceutically acceptable carrier.

7. The compound of claim 1 that is N-[2-amino-5-(2-thienyl)phenyl]-6-(3-methyl-2-oxo-1-oxa-3,8-diazaspiro[4.5]dec-8-yl)nicotinamide or a pharmaceutically acceptable salt thereof.

8. A pharmaceutical composition comprising a pharmaceutically effective amount of the compound according to claim 7, and a pharmaceutically acceptable carrier.

9. The compound of claim 1 that is N-[2-Amino-5-(2-thienyl)phenyl]-6-(2-oxo-1-oxa-3,8-diazaspiro[4.5]dec-8-yl)nicotinamide or a pharmaceutically acceptable salt thereof.

10. The compound of claim 1 that is
N-[2-amino-5-(3-thienyl)phenyl]-6-(2-oxo-1-oxa-3,8-diazaspiro[4.5]dec-8-yl)nicotinamide or a pharmaceutically acceptable salt thereof.

11. A pharmaceutical composition comprising a pharmaceutically effective amount of the compound according to claim 9, and a pharmaceutically acceptable carrier.

12. A pharmaceutical composition comprising a pharmaceutically effective amount of the compound according to claim 10, and a pharmaceutically acceptable carrier.

13. The compound of claim 4, wherein $R^3$ is H, unsubstituted or substituted phenyl or unsubstituted or substituted thienyl;

or a stereoisomer or a pharmaceutically acceptable salt thereof.

14. The compound of claim 4, wherein $R^3$ is phenyl or thienyl optionally substituted with halo;

or a stereoisomer or a pharmaceutically acceptable salt thereof.

* * * * *